(12) United States Patent
Kasina et al.

(10) Patent No.: US 6,534,037 B1
(45) Date of Patent: Mar. 18, 2003

(54) NON-STEROIDAL COMPOUNDS FOR STEROID RECEPTORS AND USES RELATING THERETO

(75) Inventors: Sudhakar Kasina, Mercer Island, WA (US); D. Mark Gleave, Seattle, WA (US)

(73) Assignee: NeoRx Corporation, Seattle, WA (US)

( * ) Notice: Subject to any disclaimer, the term of this patent is extended or adjusted under 35 U.S.C. 154(b) by 0 days.

(21) Appl. No.: 09/644,186

(22) Filed: Aug. 22, 2000

Related U.S. Application Data

(63) Continuation-in-part of application No. 09/234,784, filed on Jan. 20, 1999, now abandoned, which is a continuation of application No. 09/010,352, filed on Jan. 21, 1998, now abandoned.
(60) Provisional application No. 60/072,184, filed on Jan. 21, 1998.

(51) Int. Cl.[7] ............................................. A61K 49/00
(52) U.S. Cl. ....................... 424/9.1; 424/1.11; 424/1.65; 534/14
(58) Field of Search ............................. 424/1.11, 1.65, 424/1.37, 1.45, 9.1; 534/7, 10–16; 552/500; 562/300, 303, 700, 305, 306

(56) References Cited

U.S. PATENT DOCUMENTS

| | | |
|---|---|---|
| 4,064,150 A | 12/1977 | Katzenellenbogen ....... 260/413 |
| 4,438,117 A | 3/1984 | Cherkofsky ................. 424/251 |
| 4,851,402 A | 7/1989 | Jacobs et al. ................ 514/182 |
| 4,897,225 A | 1/1990 | Brehem et al. ............. 260/400 |
| 4,963,688 A | 10/1990 | Bodor ......................... 546/316 |
| 4,965,392 A | 10/1990 | Fritzberg et al. ............ 558/254 |
| 4,988,496 A | 1/1991 | Srinivasan et al. .......... 424/1.1 |
| 5,059,610 A | 10/1991 | Huang et al. ................ 514/314 |
| 5,075,099 A | 12/1991 | Srinivasan et al. .......... 424/1.1 |
| 5,091,514 A | 2/1992 | Fritzberg et al. .............. 534/14 |
| 5,112,953 A | 5/1992 | Gustavson et al. ....... 530/391.5 |
| 5,120,526 A | 6/1992 | Fritzberg et al. ............. 424/1.1 |
| 5,164,176 A | 11/1992 | Gustavson et al. .......... 424/1.1 |
| 5,227,474 A | 7/1993 | Johnson et al. ............. 534/558 |
| 5,247,119 A | 9/1993 | Fowler et al. ............... 558/390 |
| 5,276,147 A | 1/1994 | Thornback et al. ........... 534/14 |
| 5,554,602 A | 9/1996 | Top et al. ................... 424/1.45 |
| 5,554,750 A | 9/1996 | Wettlaufer et al. .......... 544/141 |
| 5,576,309 A | 11/1996 | Tamura et al. .............. 514/178 |
| 5,576,310 A | 11/1996 | Schubert et al. ............ 514/179 |
| 5,610,162 A | 3/1997 | Witzel et al. ................ 514/284 |
| 5,643,931 A | 7/1997 | Niigata et al. ............... 514/364 |

FOREIGN PATENT DOCUMENTS

| | | |
|---|---|---|
| EP | 315 399 B1 | 5/1989 |
| WO | WO 93/06118 | 4/1993 |

OTHER PUBLICATIONS

"Breast Cancer (Screening)," *Cancer Biotechnology Weekly*, Apr. 29, 1996.

Avril et al., "Breast Imaging with Fluorine–18–FDG PET: Quantitative Image Analysis," *The Journal of Nuclear Medicine* 38(8): 1186–1191, 1997.

Bonasera et al., "Preclinical Evaluation of Fluorine–18–Labeled Androgen Receptor Ligands in Baboons," *J. Nucl. Med.* 37(6): 1009–1015, 1996.

Chi and Katzenellenbogen, "Selective Formation of Heterodimeric Bis–Bidentate Aminothiol–Oxometal Complexes of Rhenium(V)," *J. Am. Chem. Soc.* 115: 7045–7046, 1993.

Chi et al., "Homodimeric and Heterodimeric Bis(amino thiol) Oxometal Complexes with Rhenium(V) and Technetium(V). Control of Heterodimeric Complex Formation and an Approach to Metal Complexes that Mimic Steroid Hormones," *J. Med. Chem.* 37: 928–937, 1994.

DiZio et al., "Progestin–Rhenium Complexes: Metal–Labeled Steroids with High Receptor Binding Affinity, Potential Receptor–Directed Agents for Diagnostic Imaging or Therapy," *Bioconjugate Chem.* 2: 353–366, 1991.

DiZio et al., "Technetium– and Rhenium–Labeled Progestins: Synthesis, Receptor Binding and In Vivo Distribution of an 11β–Substituted Progestin Labeled with Technetium–99 and Rhenium–186," *J. Nucl. Med.* 33(4): 558–569. 1992.

Hom and Katzenellenbogen, "Technetium–99m–Labeled Receptor–Specific Small–Molecule Radiopharmaceuticals: Recent Developments and Encouraging Results," *Nuclear Medicine & Biology* 24: 485–498, 1997.

Hom and Katzenellenbogen, "Synthesis of a Tetradentate Oxorhenium(V) Complex Mimic of a Steroidal Estrogen," *J. Org. Chem.* 62: 6290–6297, 1997.

Hom et al., "New Structural Motifs For Oxorhenium(V) Complexes Whose Structures Mimic Those Of Estrogen Receptor Ligands," in *XIIth International Symposium on Radiopharmaceutical Chemistry*, Uppsala, Sweden, Jun. 15–19, 1997, pp. 510–511.

(List continued on next page.)

*Primary Examiner*—Dameron L. Jones
(74) *Attorney, Agent, or Firm*—Seed Intellectual Property Law Group PLLC

(57) ABSTRACT

Steroid receptor analogs having good binding affinity for steroid receptors and "binding arms" for chelation to metal species such as radionuclides are prepared with all carbon backbones. The analogs very closely approximate the geometries present in natural steroids which are important for effective binding to receptor sites. In addition, metal species binding arms are strategically incorporated into the analog structure in a manner that does not disrupt the analog's receptor binding efficacy. Furthermore, the metal species binding arms may be designed to chelate one or more radionuclides, including radionuclides effective in diagnostic or therapeutic applications. With incorporation of an appropriate steroid receptor binding group, these metal species-bound analogs may be used, for example, to bind androgen receptor sites in the diagnosis or treatment of prostate cancer, or estrogen receptor sites in the diagnosis or treatment of breast and ovarian cancers.

11 Claims, 25 Drawing Sheets

OTHER PUBLICATIONS

Katzenellenbogen, "Designing Steroid Receptor–Based Radiotracers to Image Breast and Prostate Tumors," *The Journal of Nuclear Medicine* 36 Supplement(6): 8S–13S, 1995.

Labaree et al., "7α–Iodine–125–Iodo–5α– Dihydrotestosterone: A Radiolabeled Ligands for the Androgen Receptor," *J. Nucl. Med.* 38(3): 402–409, 1997.

O'Neil et al., "Progestin Radiopharmaceuticals Labeled with Technetium and Rhenium: Synthesis, Binding Affinity, and in Vivo Distribution of a New Progestin $N_2S_2$–Metal Conjugate," *Bioconjugate Chem.* 5: 182–193, 1994.

Kirschbaum et al., "[F–18]Progestins: Synthesis And Tissue Distribution Of 21–Fluoroprogestin–16α, 17α–Furan Ketals And Acetals: Potential Breast Tumor Imaging Agents," *The Journal of Nuclear Medicine* 36(5): p. 39P, Abstract No. 152, 1995.

Choe et al., "Bromo–[F–18]Fluorination: A Radiofluorination Method Applied To the Synthsis Of 11β–[F–18]Fluoroandrogens And 6α–[F–18]Fluoro–Progestins," *The Journal of Nuclear Medicine* 36(5): p. 39P, Abstract No. 153, 1995.

Welch et al. ,"[F–18]Fluorodeoxyglucose (FDG) and 16α–[F–18] Fluoroestradiol–17β (FES) Uptake In Estrogen–Receptor (ER)–Rich Tissues Following Tamoxifen Treatment: A Preclinical Study," *The Journal of Nuclear Medicine* 36(5): p. 39P, Abstract No. 155, 1995.

Hom et al., "Bis(Aminothiol) Oxorhenium Complexes Whose Structure Mimic Steroids," *The Journal of Nuclear Medicine* 36(5): p. 68P, Abstract No. 275, 1995.

Kochanny et al., "Fluorine–18–Labeled Progestin Ketals: Synthesis and Target Tissue Uptake Selectivity of Potential Imaging Agents for Receptor–Positive Breast Tumors," *J. Med. Chem.* 36: 1120–1127, 1993.

VanBrocklin et al., "16β–([$^{18}$F]Fluoro)estrogens: Systematic Investigation of a New Series of Fluorine–18–Labeled Estrogens as Potential Imaging Agents for Estrogen–Receptor–Positive Breast Tumors," *J. Med. Chem.* 36: 1619–1629, 1993.

VanBrocklin et al., "The synthesis of 7α–methyl–substituted estrogens labeled with fluorine–18: potential breast tumor imaging agents," *Steroids* 59(1): 34–45, 1994.

VanBrocklin et al., "16β–[$^{18}$F]Fluoromoxestrol: A Potent, Metabolically Stable Positron Emission Tomography Imaging Agent For Estrogen Receptor Positive Human Breast Tumors," *Life Sciences* 53: 811–819, 1993.

36

1. LAH, THF
2. H⁺

38

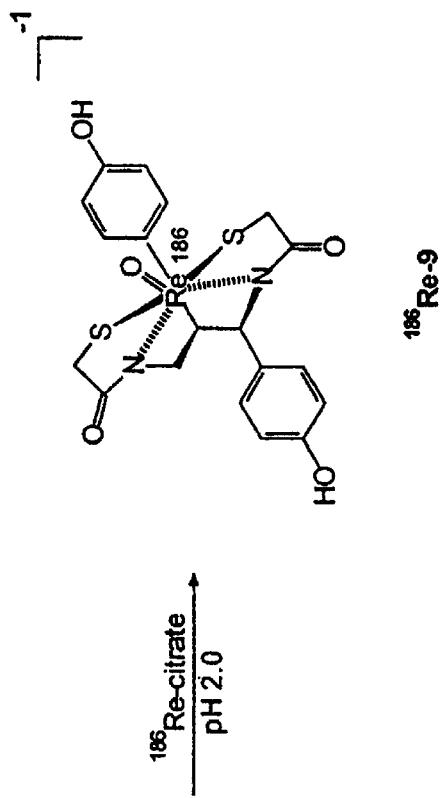
FIG. 21
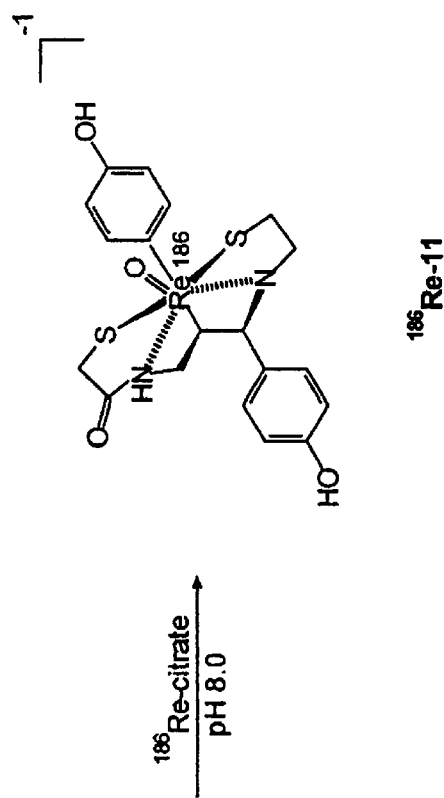
FIG. 22
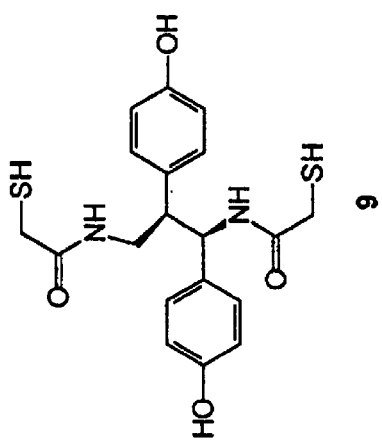
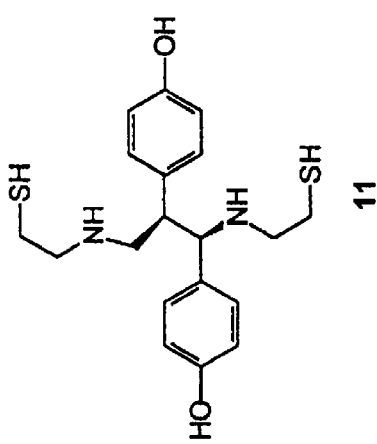

NON-STEROIDAL COMPOUNDS FOR STEROID RECEPTORS AND USES RELATING THERETO

CROSS-REFERENCE TO RELATED APPLICATION

This application is a continuation-in-part of U.S. patent application Ser. No. 09/234,784, filed Jan. 20, 1999, now abandoned, and claims the benefit of U.S. Provisional Application No. 60/072,184, filed Jan. 21, 1998 and is a continuation of U.S. patent application Ser. No. 09/010,352, filed Jan. 21, 1998 (now abandoned), which applications are incorporated herein by reference in their entirety.

TECHNICAL FIELD

The present invention relates to non-steroidal compounds which can bind to steroid receptors, and more particularly to compounds that can bind to both a steroid receptor and a radionuclide for either diagnostic or therapeutic purposes.

BACKGROUND OF THE INVENTION

Steroids are produced by many human tissues and exert significant impacts on the health and activity of humans. For example, progesterone is secreted from the corpus luteum, and in concert with estradiol, acts to maintain the uterine endometrium for egg implantation in females. Testosterone, another so-called sex hormone, is secreted by Leydig cells of testis, and after bioconversion to dihydrotestosterone, effects production of sperm proteins in Sertoli cells and is central to the development of secondary sex characteristics in males. Aldosterone, secreted from glomerulosa cells of the adrenal cortex, causes sodium ion uptake via conductance channels and thereby raises blood pressure and fluid volume during periods of stress.

After secretion, steroids are transported through the blood to receptor sites. Typically, steroids are bound to a protein during transport. Corticosteroid binding globulin protein, sex hormone binding protein, androgen binding protein and albumin are the most common binding proteins. Regardless of their bound form, steroids become unbound near their target cells and then enter the target cells to bind with a receptor. Depending on the cell, steroid receptors appear to be located within either the cell's cytoplasm or nucleus, and possibly at both locations. In structural terms, the receptor is a protein which, upon binding to a steroid, undergoes a change in conformation and activity. For instance, a steroid may induce a receptor protein to bind to a specific region of DNA, where that region then becomes accessible to RNA polymerase with subsequent stimulation of transcription.

The foregoing brief summary of steroids and steroid receptors serves to illustrate the importance of this biological system to humans and, in fact, to most animals. Further discussion of steroids and their action can be found in many texts including, to name a few, Gower, D. B. *Steroid Hormones* Croom Helm Biology in Medicine Series, Year Book Medical Publishers, Chicago, Ill. (1979); Peters, H. et al. *The Ovary* University of California Press, Berkeley, Calif. (1980); Hadley, M. C. *Endocrinology* Prentice-Hall, Inc., Englewood Cliffs, N.J. (1984); Norman, A. W. et al. *Hormones* Academic Press, Inc. New York, N.Y. (1987); Zeelen, F. J. *Pharmacochemistiy Library,* 15: *Medicinal Chemistry of Steroids* Elsevier, Amsterdam, Netherlands (1990); Bohl, M. et al. *Molecular Structure and Biological Activity of Steroids,* CRC Press, Boca Raton, Fla. (1992); and Parker, M. G. *Steroid Hormone Action* IRL Oxford, United Kingdom (1993).

Knowledge about the location and activity of steroid receptors is generally important to understanding the biochemistry of life and disease. Research is pressing forward to supplement current knowledge, which may be applied to diagnostic as well as therapeutic procedures. Diagnostic techniques which afford quantitative information about the population of receptor sites in a tissue are particularly useful in monitoring health of the tissue. Relevant to therapeutic procedures, one goal of medicinal chemists is to provide caregivers with tools to modulate the activity of steroid receptors.

One general approach to identifying biological receptors, whether for steroids or any of a host of other biologically important molecules, has been to design chemicals which may be termed "receptor analogs" that both bind to a receptor and carry with them a "functional agent". For diagnostic purposes, the functional agent may be a "marker", which is an atom or molecular fragment that can be visualized or otherwise detected in some way. For example, the marker may be a radionuclide that emits a radioactive species which can be detected by a molecular nuclear medical technique such as scintigraphic imaging. This approach allows a technician to administer a receptor analog to a subject and, after waiting an appropriate time for binding to occur, make an image of the subject which shows the location(s) where binding has occurred. In some instances, the intensity of the image may be used to develop a quantitative understanding of receptor activity. For example, cancerous cells tend to have a higher density of receptor sites than non-cancerous cells of the same type, due to an increased expression of the receptor gene. Thus, identification of a high density of steroid receptor sites may provide some indication of cancer.

Receptor analogs may be used in therapeutic as well as diagnostic applications. For instance, the functional agent of the receptor analog may be, or can be made toxic to surrounding tissue. Upon administration to a subject, the therapeutic receptor analog will bind to receptors in or on targeted cell types, and if those cell types are cancerous, then the cancer cells may be killed. For instance, the receptor analog may have a structure similar to a steroid, and thus bind to steroid receptors, however the analog has a functional agent that is a radionuclide which is toxic to nearby cells.

The approach of using steroid receptor analogs for diagnostic and therapeutic purposes has been described. However, to date, known steroid receptor analogs have not provided the desired degree of receptor binding properties, including specificity for specific receptor binding sites and strength of binding. See, e.g., Hom R. K. et al. *Nucl. Med. & Biology* 24:485–498 1997; Hom R. K. et al. Presentation from XIIth International Symposium on Radiopharmaceutical Chemistry, Uppsala, Sweden, Jun. 15–19, 1997, pp. 510–511. Hom R. K. et al. *J. Org. Chem.* 62:6290–6297, 1997; Labaree, D. C. *J Nucl. Med.* 38(3):402–409 March 1997; Avril, N. et al. *J Nucl. Med.* 38(8):1186–1191 August 1997; Top, S. et al. U.S. Pat. No. 5,554,602, issued Sep. 10, 1996; Bonasera, T. A. et al. *J. Nucl. Med.* 37(6):1009–1015 June 1996; Katzenellenbogen, J. *J. Nucl. Med.* 36(6, Supp): 8S–13S June, 1995; Choe, Y. S. et al. *J. Nucl. Med.* 36(65, Proceedings):39P, May, 1995; O'Neil, J. P. et al. *Bioconjugate Chem.* 5:182–193 1994; Chi, D. Y. et al. *J. Med. Chem.* 37:928–937 1994; Chi, D. Y. et al. *J.A.C.S.* 115:7045–7046 1993; DiZio, J. P. et al. *J. Nucl. Med.* 33(4):558–569 April 1992; and DiZio, J. P. et al. *Bioconjugate Chem.* 2:353–366 1991.

Therefore, there is a need in the art for effective receptor analogs, which demonstrate specificity to an intended steroid receptor, and can deliver functional agents to the steroid receptor. The present invention fulfills this need and further provides other related advantages as disclosed herein.

SUMMARY OF THE INVENTION

A compound of the formula (I)

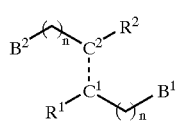
(I)

wherein,
A) $R^1$ and $R^2$ together are a steroid receptor binding group where,
  i) $R^1$ and $R^2$ are independently selected from

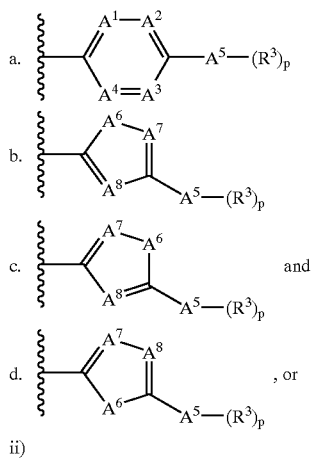

ii)

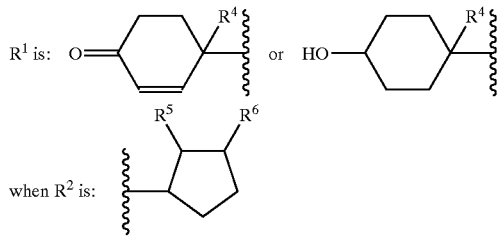

where A1, A2, A3, A4, A7 and A8 are independently selected from —CH—, —CX—, —C(OH)— and N, where X is halide, with the proviso that not more than three of A1, A2, A3 and A4 are simultaneously N, and not more than one of A7 and A8 are simultaneously N;

A5 and p are independently selected from (A5/p): O/1, S/1, Se/1, C(=O)O/1, N/2, P/2, and Si/3, where R3 at each occurrence is independently selected from H, C1–C10hydrocarbyl, and a protecting group for A5, or A5—(R3)p may together form —NO2, hydrogen or halogen;
$A^6$ is selected from S, O and NH;
$R^4$ is selected from H, —OH, halide and $C_1$–$C_3$alkyl;
$R^5$ is selected from H, —OH, halide and $C_1$–$C_3$alkyl; and
$R^6$ is selected from H, —OH, —SH, halide, $C_1$–$C_3$alkyl, C(=O)CH$_3$, thio and oxo;

B) $C^1$ and $C^2$ are joined together by
  i) a double bond, or
  ii) a single bond, where
    a. the single bond may form part of a 3- to 5-membered carbocyclic or heterocyclic ring, the heterocyclic ring containing one heteroatom selected from oxygen, nitrogen and sulfur; or
    b. C1 and C2 are independently substituted with H, halogen, or C1–C3alkyl; or
    c. C1 may join B1 through a C1=N double bond, and/or C2 may join B2 through a C2=N double bond;

C)

represents a number "n" of methylene (CH$_2$) or fluoromethylene (CFH or CF$_2$) groups, where n is independently selected at each occurrence from 0, 1 and 2;

D) at least one of $B^1$ and $B^2$ is a metal species binding group, where
  i) $B^1$ and $B^2$ may together be capable of binding one metal species and each has a structure selected from

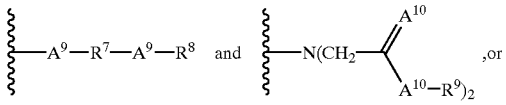

ii) $B^1$ and $B^2$ may together form the cyclic structure

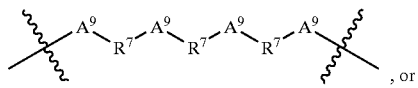

iii) $B^1$ and $B^2$ may each be capable of binding one metal species and each has a structure independently selected from

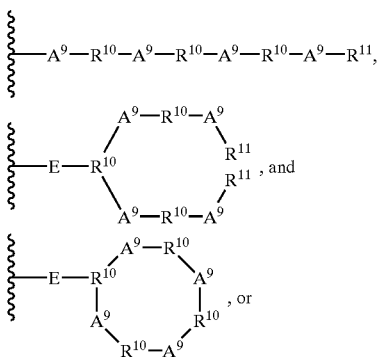

iv) only one of $B^1$ and $B^2$ is capable of binding a metal species, where one of $B^1$ and $B^2$ has a structure selected from D) iii) above, and the other of $B^1$, and $B^2$ is selected from H and groups that affect the in vivo pharmacological behavior of the compound, such as $C_1$–$C_{10}$hydrocarbyl or a polar group which increases the hydrophilicity of the compound, such as carboxylates, sulfonates and secondary alcohols; where,
    a. $A^9$ is an electron-donating moiety independently selected at each occurrence from O, S, C(=O)NH and N($R^{12}$), where $R^{12}$ is selected from hydrogen and pro-drug substituents selected from the group consisting of $C_1$–$C_3$alkyl, —C(=O)(H, $C_1$–$C_3$alkyl or Ar), —C(=O)—($C_1$–$C_3$alkylene)-

N(independently H or $C_1$–$C_3$alkyl)$_2$, —C(=O)
O—(H, $C_1$–$C_3$alkyl or Ar), —C(=O)CH(NH$_2$)
(H, $C_1$–$C_3$alkyl or Ar), —($C_1$–$C_3$alkylene)-C
(=O)O—(H, $C_1$–$C_3$alkyl or Ar),
—($C_1$–$C_3$alkylene)-OC(=O)—(H, $C_1$–$C_3$alkyl or
Ar), —($C_1$–$C_3$alkylene)-N(independently H or
$C_1$–$C_3$alkyl)$_2$, —($C_1$–$C_3$alkylene)-NHC(=O)—
Ar, —($C_1$–$C_3$alkylene)-CN, —($C_1$–$C_3$alkylene)-
NO$_2$, and

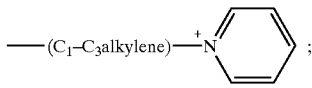

b. $R^7$ and $R^{10}$ each have a structure which at each occurrence is independently selected from

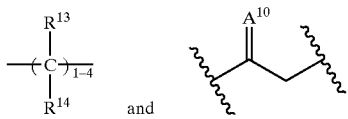

where $R^{13}$ and $R^{14}$ are independently selected from H, $R^{15}$, —CN, —NO$_2$, —NO, —C(O$C_1$–$C_3$alkyl)=NH, —N=C=O, —N=C=S, and —C(=O)O$R^{15}$ where $R^{15}$ is $C_1$–$C_6$hydrocarbyl, such that when $R^{10}$ is bonded to E, then $R^{13}$ is a direct bond to E;

c. $R^8$, $R^9$ and $R^{11}$ are independently selected from H and protecting groups for the $A^9$ or $A^{10}$ moiety to which the $R^8$, $R^9$ or $R^{11}$ is bonded;

d. $A^9$ and $R^{11}$ may together form —N(CH$_2$—COOH)$_2$;

e. $A^{10}$ is independently selected from O and S; and f. E is an "extender arm" which covalently links a metal species binding site to $C^1$ or $C^2$, and has a structure which provides a stable chain of 2–60 atoms selected from carbon, oxygen, nitrogen and sulfur.

In another embodiment, the present invention provides compounds of the formula (I)

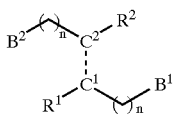

wherein,

A) $R^1$ and $R^2$ together are a steroid receptor binding group where,
  i) $R^1$ and $R^2$ are independently selected from

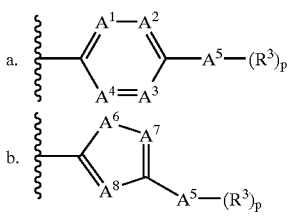

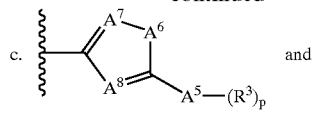

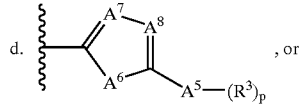

ii)

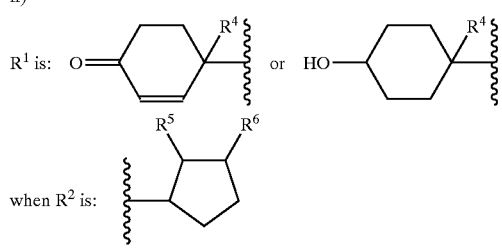

where $A^1$, $A^2$, $A^3$, $A^4$, $A^7$ and $A^8$ are independently selected from —CH—, —CX—, —C(OH)— and N, where X is halide, with the proviso that not more than three of $A^1$, $A^2$, $A^3$ and $A^4$ are simultaneously N, and not more than one of $A^7$ and $A^8$ are simultaneously N;

$A^5$ and p are independently selected from ($A^5$/p): O/1, S/1, Se/1, C(=O)O/1, N/2, P/2, and Si/3, where $R^3$ at each occurrence is independently selected from H, $C_1$–$C_{10}$hydrocarbyl, and a protecting group for $A^5$, or $A^5$—($R^3$)$_p$ may together form —NO$_2$, hydrogen or halogen;

$A^6$ is selected from S, O and NH;

$R^4$ is selected from H, —OH, halide and $C_1$–$C_3$alkyl;

$R^5$ is selected from H, —OH, halide and $C_1$–$C_3$alkyl; and $R^6$ is selected from H, —OH, —SH, halide, $C_1$–$C_3$alkyl, C(=O)CH$_3$, oxo and thio;

B) $C^1$ and $C^2$ are joined together by
  i) a double bond, or
  ii) a single bond, where
    a. the single bond may form part of a 3- to 5-membered carbocyclic or heterocyclic ring, the heterocyclic ring containing one heteroatom selected from oxygen, nitrogen and sulfur; or
    b. $C^1$ and $C^2$ are independently substituted with H, halogen, or $C_1$–$C_3$alkyl; or
    c. $C^1$ may join $B^1$ through a $C^1$=N double bond, and/or $C^2$ may join $B^2$ through a $C^2$=N double bond;

C)

represents a number "n" of methylene (CH$_2$) or fluoromethylene (CFH or CF$_2$) groups, where n is independently selected at each occurrence from 0, 1 and 2;

D) at least one of $B^1$ and $B^2$ is a metal species binding group, where
  i) $B^1$ and $B^2$ may together be capable of binding one metal species and each has a structure selected from

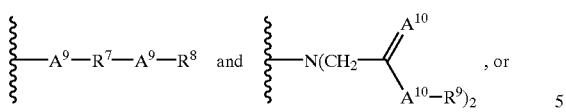

ii) $B^1$ and $B^2$ may together form the cyclic structure

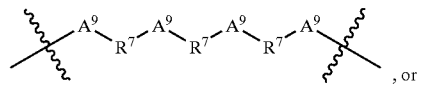

iii) $B^1$ and $B^2$ may each be capable of binding one metal species and each has a structure independently selected from

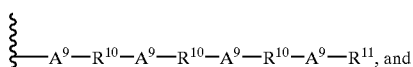

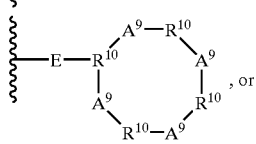

iv) only one of $B^1$ and $B^2$ is capable of binding a metal species, where one of $B^1$ and $B^2$ has a structure selected from D) iii) above, and the other of $B^1$ and $B^2$ is selected from H and groups that affect the in vivo pharmacological behavior of the compound, such as $C_1$–$C_{10}$hydrocarbyl or a polar group which increases the hydrophilicity of the compound, such as carboxylates, sulfonates and secondary alcohols; where, a. $A^9$ is an electron-donating moiety independently selected at each occurrence from O, S, C(=O)NH and N($R^{12}$), where $R^{12}$ is selected from hydrogen and pro-drug substituents selected from the group consisting of $C_1$–$C_3$alkyl, —C(=O)(H, $C_1$–$C_3$alkyl or Ar), —C(=O)—($C_1$–$C_3$alkylene)-N(independently H or $C_1$–$C_3$alkyl)$_2$, —C(=O)O—(H, $C_1$–$C_3$alkyl or Ar), —C(=O)CH(NH$_2$)(H, $C_1$–$C_3$alkyl or Ar), —($C_1$–$C_3$alkylene)-C(=O)O—(H, $C_1$–$C_3$alkyl or Ar), —($C_1$–$C_3$alkylene)-OC(=O)—(H, $C_1$–$C_3$alkyl or Ar), —($C_1$–$C_3$alkylene)-N(independently H or $C_1$–$C_3$alkyl)$_2$, —($C_1$–$C_3$alkylene)-NHC(=O)—Ar, —($C_1$–$C_3$alkylene)-CN, —($C_1$–$C_3$alkylene)-NO$_2$, and

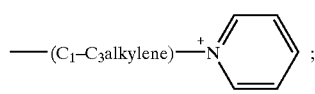

b. $R^7$ and $R^{10}$ each have a structure which at each occurrence is independently selected from

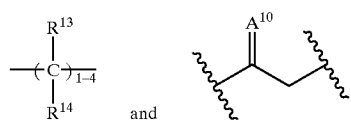

where $R^{13}$ and $R^{14}$ are independently selected from H, $R^{15}$, —CN, —NO$_2$, —NO, —C(OC$_1$–C$_3$alkyl)=NH, —N=C=O, —N=C=S, and —C(=O)OR$^{15}$ where $R^{15}$ is $C_1$–$C_6$hydrocarbyl, such that when $R^{10}$ is bonded to E, then $R^{13}$ is a direct bond to E;

c. $R^8$, $R^9$ and $R^{11}$ are independently selected from H and protecting groups for the $A^9$ or $A^{10}$ moiety to which the $R^8$, $R^9$ or $R^{11}$ is bonded;

d. $A^9$ and $R^{11}$ may together form —N(CH$_2$—COOH)$_2$;

e. $A^{10}$ is independently selected from O and S; and f. E is an "extender arm" which covalently links a metal species binding site to $C^1$ or $C^2$, and has a structure which provides a chain of 2–60 atoms selected from carbon, oxygen, nitrogen and sulfur.

In another aspect, the present invention provides a compound of the formula (II)

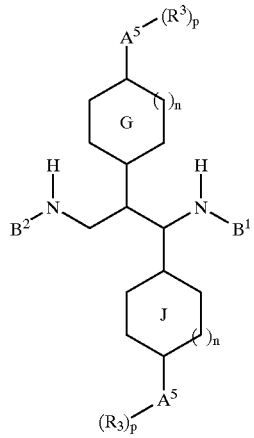

wherein, independently at each occurrence, n is 0 or 1;

the rings surrounded by "G" and "J" are five- or six-membered rings depending on the value of n, and the rings may be saturated or unsaturated;

$A^5$ and p are independently selected from ($A^5$/p): O/1, S/1, Se/1, C(=O)O/1, N/2, P/2, and Si/3, where $R^3$ at each occurrence is independently selected from H, $C_1$–$C_{10}$hydrocarbyl, and a protecting group for $A^5$, or $A^5$—($R^3$)$_p$ may together form —NO$_2$, hydrogen=O or halogen;

at least one of $B^1$ and $B^2$ is a metal species binding group, where i) $B^1$ and $B^2$ may together be capable of binding one metal species and each has a structure selected from

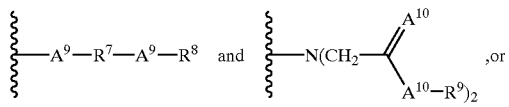

ii) $B^1$ and $B^2$ may together form the cyclic structure

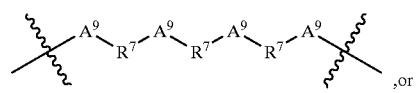

iii) $B^1$ and $B^2$ may each be capable of binding one metal species and each has a structure independently selected from

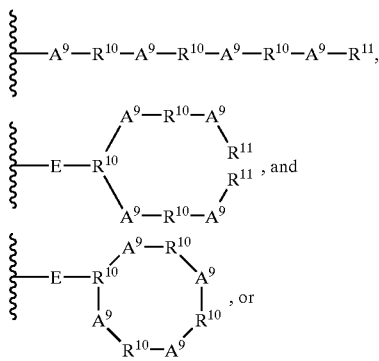

iv) only one of $B^1$ and $B^2$ is capable of binding a metal species, where one of $B^1$ and $B^2$ has a structure selected from D) iii) above, and the other of $B^1$ and $B^2$ is selected from H and groups that affect the in vivo pharmacological behavior of the compound, such as $C_1$–$C_{10}$hydrocarbyl or a polar group which increases the hydrophilicity of the compound;

where, a. $A^9$ is an electron-donating moiety independently selected at each occurrence from O, S, C(=O)NH and N($R^{12}$), where $R^{12}$ is selected from hydrogen and pro-drug substituents selected from the group consisting of $C_1$–$C_3$alkyl, —C(=O)(H, $C_1$–$C_3$alkyl or Ar), —C(=O)—($C_1$–$C_3$alkylene)-N(independently H or $C_1$–$C_3$alkyl)$_2$, —C(=O)O—(H, $C_1$–$C_3$alkyl or Ar), —C(=O)CH(NH$_2$)(H, $C_1$–$C_3$alkyl or Ar), —($C_1$–$C_3$alkylene)-C(=O)O—(H, $C_1$–$C_3$alkyl or Ar), —($C_1$–$C_3$alkylene)-OC(=O)—(H, $C_1$–$C_3$alkyl or Ar), —($C_1$–$C_3$alkylene)-N(independently H or $C_1$–$C_3$alkyl)$_2$, —($C_1$–$C_3$alkylene)-NHC(=O)—Ar, —($C_1$–$C_3$alkylene)-CN, —($C_1$–$C_3$alkylene)-NO$_2$, and

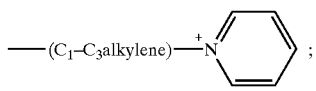

b. $R^7$ and $R^{10}$ each have a structure which at each occurrence is independently selected from

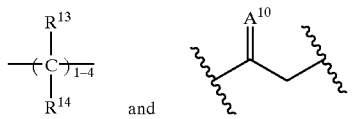

where $R^{13}$ and $R^{14}$ are independently selected from H, $R^{15}$, —CN, —NO$_2$, —NO, —C(O$C_1$–$C_3$alkyl)=NH, —N=C=O, —N=C=S, and —C(=O)O$R^{15}$ where $R^{15}$ is $C_1$–$C_6$hydrocarbyl, such that when $R^{10}$ is bonded to E, then $R^{13}$ is a direct bond to E;

c. $R^8$, $R^9$ and $R^{11}$ are independently selected from H and protecting groups for the $A^9$ or $A^{10}$ moiety to which the $R^8$, $R^9$ or $R^{11}$ is bonded;

d. $A^9$ and $R^{11}$ may together form —N(CH$_2$—COOH)$_2$;

e. $A^{10}$ is independently selected from O and S; and f. E is an "extender arm" which covalently links a metal species binding site to the remainder of the molecules, and has a structure which provides a stable chain of 2–60 atoms selected from carbon, oxygen, nitrogen and sulfur.

In another embodiment, the present invention provides chelation products (chelates) of compounds of formulae (I) and (II). The chelation products are compounds of formula (I) and (II) chelated to at least one metal or metal ion (collective a "metal species"). Radionuclides are preferred metal species of the present invention. The radionuclide may be in the form of an oxide or nitride, as two examples.

The steroid analogs of the above formulae (I) and (II), and chelates thereof, may be in the form of a solvate or a pharmaceutically acceptable salt, e.g., an acid addition or base addition salt. Such salts include hydrochloride, sulfate, phosphate, citrate, fumarate, methanesulfonate, acetate, tartrate, maleate, lactate, mandelate, salicylate, succinate and other salts known in the art.

A steroid receptor analog, and a chelate thereof, of the present invention may be prepared as a composition by combining it with a pharmaceutically acceptable carrier or diluent. Suitable carriers or diluents include physiological saline. It will be evident to those of ordinary skill in the art that a composition of the present invention may contain more than one steroid receptor analog compound.

In another embodiment, the invention provides a method of binding a steroid analog to a steroid receptor for a therapeutic or diagnostic purpose. The method includes the step of administering to a subject in need thereof a therapeutically or diagnostically effective amount of a steroid receptor analog, chelate thereof, or pharmaceutical composition containing a steroid receptor analog or chelate thereof.

In another embodiment, the present invention provides a method of imaging a steroid receptor. The method includes the step of administering to a subject in need thereof a diagnostically effective amount of a steroid receptor analog, chelate thereof, or pharmaceutical composition containing a steroid receptor analog or chelate thereof.

In another embodiment, the present invention provides a method of killing a cell having a steroid receptor. The method includes the step of administering to a subject in need thereof, in an amount effective to kill a cell, of a steroid receptor analog, chelate thereof, or pharmaceutical composition containing a steroid receptor analog or chelate thereof.

BRIEF DESCRIPTION OF THE DRAWINGS

FIG. 21 illustrates the chemistry more fully described in Example 21 which may be used to form an estrogen receptor therapeutic agent of the invention from $^{186}Re$ and an estrogen receptor analog of the invention having four donor atoms forming an $N_2S_2$ binding core, where the N atoms are part of amide groups and the sulfur atoms are in the form of thiols.

FIG. 22 illustrates the chemistry more fully described in Example 22 which may be used to form an estrogen receptor therapeutic agent of the invention from $^{186}Re$ and an estrogen receptor analog of the invention having four donor atoms forming an $N_2S_2$ binding core, where the N atoms are part of amine groups and the sulfur atoms are in the form of thiols.

Figure 1A:
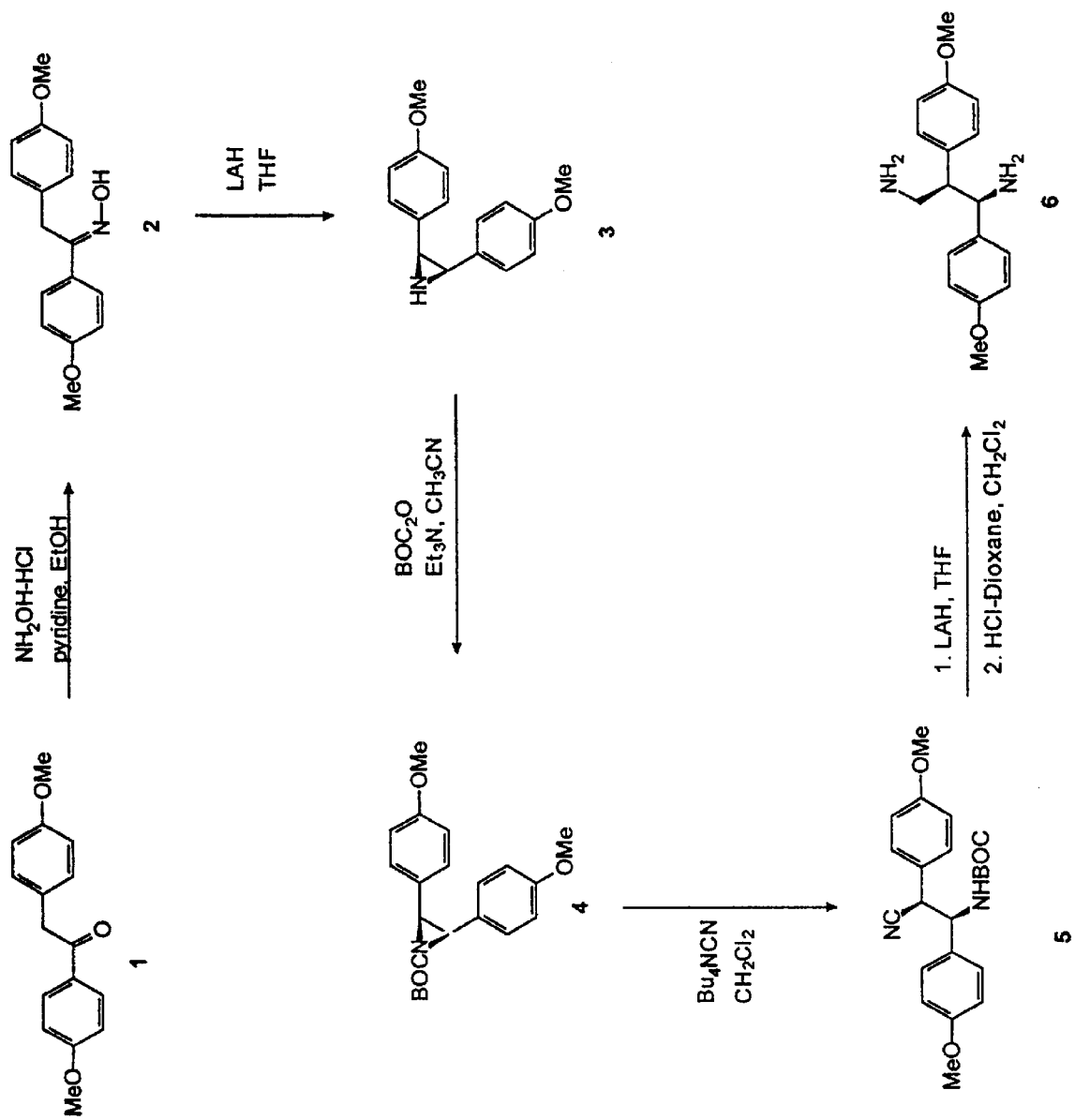
FIG. 1A illustrates a series of chemical reactions more fully described in Example 1 that may be employed to prepare a precursor to steroid receptor analogs of the invention having affinity for estrogen receptors.

These and other embodiments of the present invention will become evident upon reference to the following detailed description and attached drawings.

DETAILED DESCRIPTION OF THE INVENTION

The present inventors have discovered that using steroid analogs with carbon backbones provides analogs having optimal distances for mimicking the binding behavior of natural steroids, including estrogens, progestins and androgens. Furthermore, in a preferred embodiment, the analogs of the present invention have been specifically designed to incorporate chelating sites for metal species in a manner that does not compromise efficient binding to steroid receptor sites. The steroid analogs of the present invention, chelates thereof, compositions containing the same, and the use of the analogs, chelates and compositions in therapeutic and diagnostic applications is described herein.

Steroid Analogs

The present invention provides compounds of the formula (I)

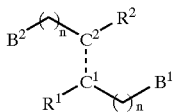

wherein,

A) $R^1$ and $R^2$ together are a steroid receptor binding group where,
  i) $R^1$ and $R^2$ are independently selected from a. 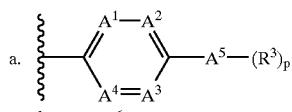

b. 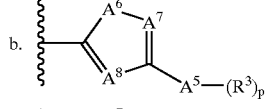

c. 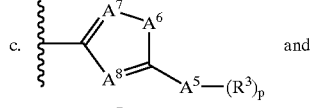 and d. 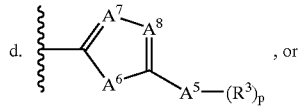, or ii)
  $R^1$ is: 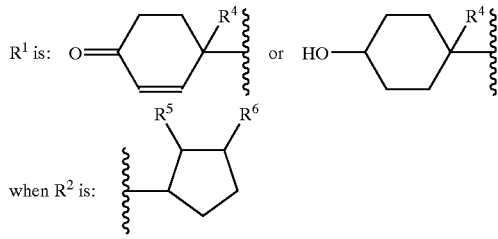

when $R^2$ is:

where $A^1$, $A^2$, $A^3$, $A^4$, $A^7$ and $A^8$ are independently selected from —CH—, —CX—, —C(OH)— and N, where X is halide;
  $A^5$ and p are independently selected from ($A^5$/p): O/1, S/1, Se/1, C(=O)O/1, N/2, P/2, and Si/3, where $R^3$ at each occurrence is independently selected from H, $C_1$-$C_{10}$hydrocarbyl, and a protecting group for $A^5$, or $A^5$—$(R^3)_p$ may together form —$NO_2$, hydrogen or halogen;
  $A^6$ is selected from S, O and NH;
  $R^4$ is selected from H, —OH, halide and $C_1$-$C_3$alkyl;
  $R^5$ is selected from H, —OH, halide and $C_1$-$C_3$alkyl; and
  $R^6$ is selected from H, —OH, —SH, halide, $C_1$-$C_3$alkyl, C(=O)$CH_3$, oxo and thio;

B) $C^1$ and $C^2$ are joined together by
  i) a double bond, or
  ii) a single bond, where
    a. the single bond may form part of a 3- to 5-membered carbocyclic or heterocyclic ring, the heterocyclic ring containing one heteroatom selected from oxygen, nitrogen and sulfur; or
  b. $C^1$ and $C^2$ are independently substituted with H, halogen, or $C_1$-$C_3$alkyl; or
  c. $C^1$ may join $B^1$ through a $C^1$=N double bond, and/or $C^2$ may join $B^2$ through a $C^2$=N double bond.

C)

represents a number "n" of methylene ($CH_2$) or fluoromethylene (CFH or $CF_2$) groups, where n at each occurrence is independently selected from 0, 1 and 2;

D) at least one of $B^1$ and $B^2$ is a metal species binding group, where
  i) $B^1$ and $B^2$ may together be capable of binding one metal species and each has a structure selected from

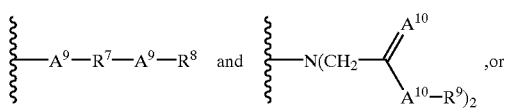

ii) $B^1$ and $B^2$ may together form the cyclic structure

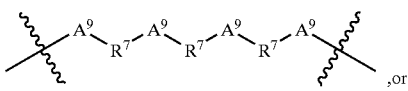, or iii) $B^1$ and $B^2$ may each be capable of binding one metal species and each has a structure independently selected from

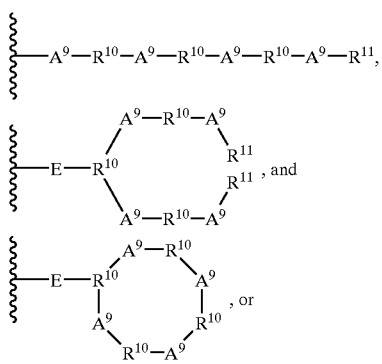

iv) only one of $B^1$ and $B^2$ is capable of binding a metal species, where one of $B^1$ and $B^2$ has a structure selected from D) iii) above, and the other of $B^1$ and $B^2$ is selected from H and groups that affect the in vivo pharmacological behavior of the compound, such as $C_1$-$C_{10}$hydrocarbyl or a polar group which increases the hydrophilicity of the compound, such as carboxylates, sulfonates and secondary alcohols; where,
  a. $A^9$ is an electron-donating moiety independently selected at each occurrence from O, S, C(=O)NH and N($R^{12}$), where $R^{12}$ is selected from hydrogen and pro-drug substituents selected from the group consisting of $C_1$-$C_3$alkyl, —C(=O)(H, $C_1$-$C_3$alkyl or Ar), —C(=O)—($C_1$-$C_3$alkylene)-N(independently H or $C_1$-$C_3$alkyl)$_2$, —C(=O)

O—(H, $C_1$-$C_3$alkyl or Ar), —C(=O)CH(NH$_2$) (H, $C_1$-$C_3$alkyl or Ar), —($C_1$-$C_3$alkylene)-C(=O)O—(H, $C_1$-$C_3$alkyl or Ar), —($C_1$-$C_3$alkylene)-OC(=O)—(H, $C_1$-$C_3$alkyl or Ar), —($C_1$-$C_3$alkylene)-N(independently H or $C_1$-$C_3$alkyl)$_2$, —($C_1$-$C_3$alkylene)-NHC(=O)—Ar, —($C_1$-$C_3$alkylene)-CN, —($C_1$-$C_3$alkylene)-NO$_2$, and

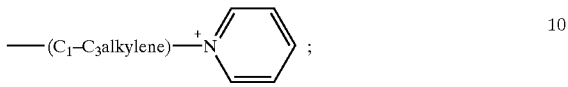

b. $R^7$ and $R^{10}$ each have a structure which at each occurrence is independently selected from

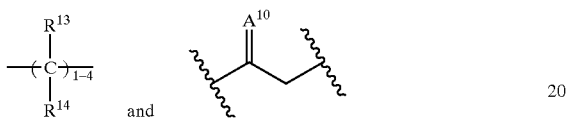

where $R^{13}$ and $R^{14}$ are independently selected from H, $R^{15}$, —CN, —NO$_2$, —NO, —C(OC$_1$-C$_3$alkyl)=NH, —N=C=O, —N=C=S, and —C(=O)OR$^{15}$ where $R^{15}$ is $C_1$-$C_6$hydrocarbyl, such that when $R^{10}$ is bonded to E, then $R^{13}$ is a direct bond to E;
c. $R^8$, $R^9$ and $R^{11}$ are independently selected from H and protecting groups for the $A^9$ or $A^{10}$ moiety to which the $R^8$, $R^9$ or $R^{11}$ is bonded;
d. $A^9$ and $R^{11}$ may together form —N(CH$_2$—COOH)$_2$;
e. $A^{10}$ is independently selected from O and S; and
f. E is an "extender arm" which covalently links a metal species binding site to $C^1$ or $C^2$, and has a structure which provides a stable chain of 2–60 atoms selected from carbon, oxygen, nitrogen and sulfur.

In another aspect, the present invention provides a compound of the formula (II)

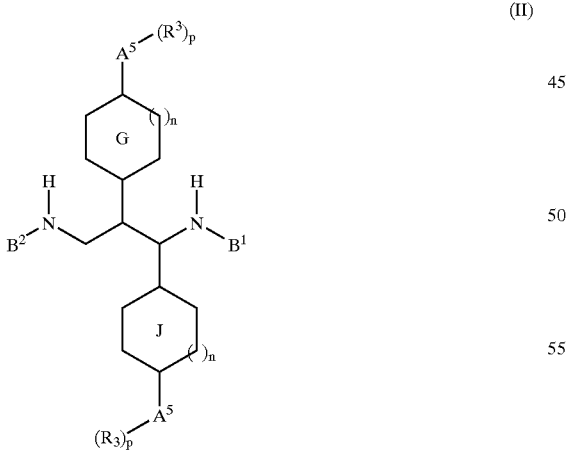

(II)

wherein, independently at each occurrence,
n is 0 or 1;
the rings surrounded by "G" and "J" are five- or six-membered rings depending on the value of n, and the rings may be saturated or unsaturated;
$A^5$ and p are independently selected from ($A^5$/p): O/1, S/1, Se/1, C(=O)O/1, N/2, P/2, and Si/3, where $R^3$ at each occurrence is independently selected from H, $C_1$-$C_{10}$hydrocarbyl, and a protecting group for $A^5$, or $A^5$—(R$^3$)$_p$ may together form —NO$_2$, hydrogen=O or halogen;
at least one of $B^1$ and $B^2$ is a metal species binding group, where
i) $B^1$ and $B^2$ may together be capable of binding one metal species and each has a structure selected from

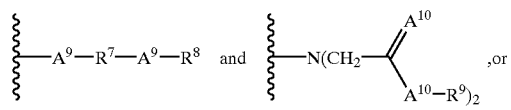

ii) $B^1$ and $B^2$ may together form the cyclic structure

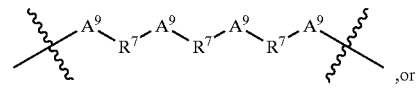

iii) $B^1$ and $B^2$ may each be capable of binding one metal species and each has a structure independently selected from

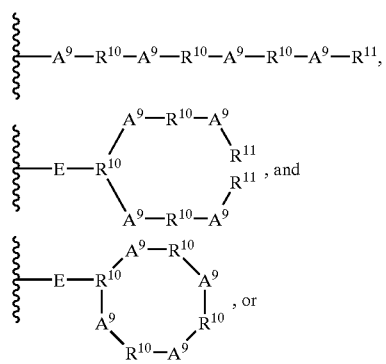

iv) only one of $B^1$ and $B^2$ is capable of binding a metal species, where one of $B^1$ and $B^2$ has a structure selected from D) iii) above, and the other of $B^1$ and $B^2$ is selected from H and groups that affect the in vivo pharmacological behavior of the compound, such as $C_1$-$C_{10}$hydrocarbyl or a polar group which increases the hydrophilicity of the compound;
where,
a. $A^9$ is an electron-donating moiety independently selected at each occurrence from O, S, C(=O)NH and N($R^{12}$), where $R^{12}$ is selected from hydrogen and pro-drug substituents selected from the group consisting of $C_1$-$C_3$alkyl, —C(=O)(H, $C_1$-$C_3$alkyl or Ar), —C(=O)—($C_1$-$C_3$alkylene)-N(independently H or $C_1$-$C_3$alkyl)$_2$, —C(=O)O—(H, $C_1$-$C_3$alkyl or Ar), —C(=O)CH(NH$_2$) (H, $C_1$-$C_3$alkyl or Ar), —($C_1$-$C_3$alkylene)-C(=O)O—(H, $C_1$-$C_3$alkyl or Ar), —($C_1$-$C_3$alkylene)-OC(=O) —(H, $C_{1C3}$alkyl or Ar), —($C_1$-$C_3$alkylene)-N(independently H or $C_1$-$C_3$alkyl)$_2$, —($C_1$-$C_3$alkylene)-NHC(=O)—Ar, —($C_1$-$C_3$alkylene)-CN, —($C_1$-$C_3$alkylene) NO$_2$, and

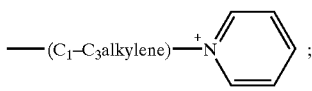

b. $R^7$ and $R^{10}$ each have a structure which at each occurrence is independently selected from

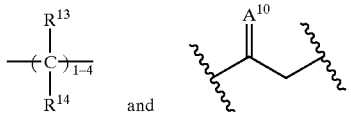

where $R^{13}$ and $R^{14}$ are independently selected from H, $R^{15}$, —CN, —NO$_2$, —NO, —C(OC$_1$–C$_3$alkyl)=NH, —N=C=O, —N=C=S, and —C(=O)OR$^{15}$ where $R^{15}$ is C$_1$–C$_6$hydrocarbyl, such that when $R^{10}$ is bonded to E, then $R^{13}$ is a direct bond to E;

c. $R^8$, $R^9$ and $R^{11}$ are independently selected from H and protecting groups for the $A^9$ or $A^{10}$ moiety to which the $R^8$, $R^9$ or $R^{11}$ is bonded;

d. $A^9$ and $R^{11}$ may together form —N(CH$_2$—COOH)$_2$;

e. $A^{10}$ is independently selected from O and S; and f. E is an "extender arm" which covalently links a metal species binding site to the remainder of the molecules, and has a structure which provides a stable chain of 2–60 atoms selected from carbon, oxygen, nitrogen and sulfur.

The compounds of formulae (I) and (II) are "steroid receptor analogs" in that they contain chemical moieties which mimic certain critical features of natural steroids and thereby meet the geometric demands of steroid receptors. Thus, when the compound of formula (I) has $R^1$ and $R^2$ groups selected from a., b., c., and d. below,

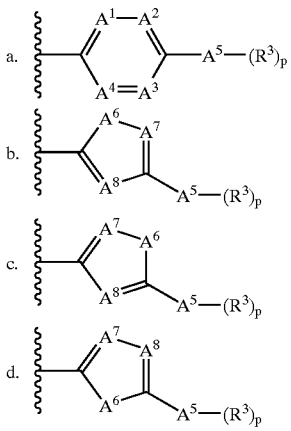

then the steroid receptor analog may bind to estrogen receptors.

In the above $R^1$ and $R^2$ groups, $A^1$, $A^2$, $A^3$, and $A^4$ are independently selected from —CH—, —CX—, —C(OH)— and N, where X is halide. In preferred embodiments, not more than three of $A^1$, $A^2$, $A^3$ and $A^4$ are simultaneously N, and not more than one of $A^7$ and $A^8$ are simultaneously N. In a preferred embodiment of the invention, each of $A^1$, $A^2$, $A^3$ and $A^4$ is —CH—.

When the steroid receptor binding groups $R^1$ and $R^2$ are selected from 5-membered rings (i.e., options "b.", "c." and "d." above), then $A^6$ is selected from S, O and NH, while $A^7$ and $A^8$ are independently selected from —CH—, —CX—, —C(OH)— and N, where X is halide. In a preferred embodiment, not more than one of $A^7$ and $A^8$ are simultaneously N. In a preferred embodiment of the invention, $A^6$ is S and each of $A^7$ and $A^8$ is —CH—.

In the above $R^1$ and $R^2$ groups, $A^5$ and p are independently selected from ($A^5$/p): O/1, S/1, Se/1, C(=O)O/1, N/2, P/2, and Si/3. The designation "O/1" for "$A^5$/p", for example, means that one option is to have $A^5$ be oxygen and p be 1. Regardless of the selection of $A^5$ and p, $R^3$ at each occurrence is independently selected from H, C$_1$–C$_{10}$hydrocarbyl, and a protecting group for $A^5$. In addition, $A^5$—(R$^3$)$_p$ may together form —NO$_2$, hydrogen or halogen. In a preferred embodiment of the invention, $A^5$—(R$^3$)$_p$ represents hydroxyl (i.e., —OH).

However, when the compound of formula (I) has $R^1$ and $R^2$ groups such that,

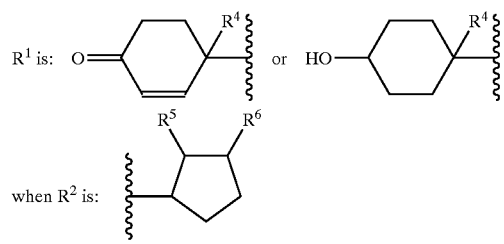

then the compound has groups which mimic androgens, and the compound may function as a androgen receptor analog. In this instance, $R^4$ is selected from H, —OH, halide and C$_1$–C$_3$alkyl; $R^5$ is selected from H, —OH, halide and C$_1$–C$_3$alkyl; and $R^6$ is selected from H, —OH, —SH, halide, C$_1$–C$_3$alkyl, C(=O)CH$_3$, oxo and thio. As used herein, the terms "oxo" and "thio" indicate that either a carbonyl (C=O) or thiocarbonyl (C=S) group, respectively, is bonded to the carbon atom of $R^2$ to which $R^6$ is bonded. Thus, $R^2$ groups of the invention include each of the following:

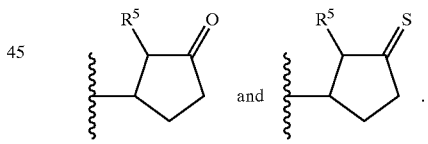

In a preferred embodiment, $R^4$ is methyl, $R^5$ is methyl, and $R^6$ is hydroxyl. In a preferred embodiment, $R^1$ has one of the following stereochemistries (shown relative to $C^1$ and $C^2$ in formula (I)):

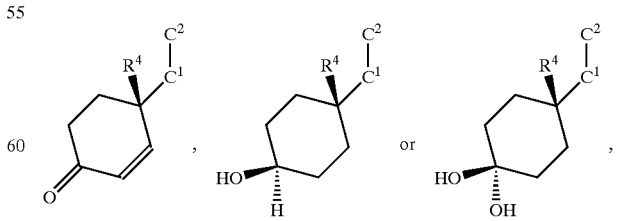

while in another preferred embodiment, $R^2$ has the following stereochemistry (shown relative to $C^1$ and $C^2$ in formula (I)):

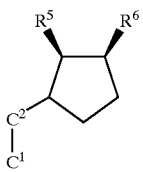

Extender Arms

In compounds of formulae (I) and (II) E is a group that functions as an "extender arm" and may be useful to distance the steroid binding site from the chelating portion (metal species binding arms) of the steroid receptor analog. Extender arms of the invention covalently link a metal species binding site to $C^1$ or $C^2$ through a chain of 2–60 atoms selected from carbon, oxygen, nitrogen and sulfur. The chain is "stable" in that it can exist at room temperature without spontaneously decomposing to constituent atoms or molecular fragments. Stable groups include cleavable linkers such as carboxylate esters, acetate esters, imidate esters and carbamates, among others. Other groups which may be used include methylene (—$CH_2$—), methyleneoxy (—$CH_2O$—), methylenecarbonyl (—$CH_2$—CO—), or combinations thereof. The number, m, of groups such as these would be typically 0 to 30 and preferably 0 to 5. Polyamides, as formed from, for example, condensation of amino acids, are a preferred extender arm.

Sulfur Protecting Groups

The steroid analogs of formulae (I) and (II) may contain one or more protecting groups for one or more atoms. Suitable protecting groups are set forth in Greene, "Protective Groups in Organic Chemistry", John Wiley & Sons, New York N.Y. (1991).

Sulfur atoms may be protected in steroid analogs of the present invention. In one embodiment of the invention, the sulfur protecting group, when taken together with the sulfur atom to be protected, is a hemithioacetal group. Suitable hemithioacetals include, but are not limited to, those having the following formulae, wherein the sulfur atom is the sulfur atom of the steroid analog.

—S—$CH_2$—O—$CH_3$

—S—$CH_2$—O—$(CH_2)_2$—$OCH_3$ and

—S—$CH_2$—O—$CH_2$—$CH(CHC_3)_2$.

Preferred hemithioacetals generally are of the following formula, wherein the sulfur atom is the sulfur atom of the chelating compound.

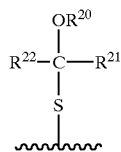

wherein $R^{20}$ is a lower alkyl group, preferably of from 2 to 5 carbon atoms, and $R^{22}$ is H or a lower alkyl group, preferably of from 1 to 3 carbon atoms. Alternatively, $R^{20}$ and $R^{22}$ may be taken together with the carbon atom and the oxygen atom shown in the formula to define a nonaromatic ring, preferably comprising from 3 to 7 carbon atoms in addition to the carbon and oxygen atoms shown in the formula. $R^{21}$ represents hydrogen or a lower alkyl group wherein the alkyl group preferably is of from 1 to 3 carbon atoms.

Examples of such preferred hemithioacetals include, but are not limited to:

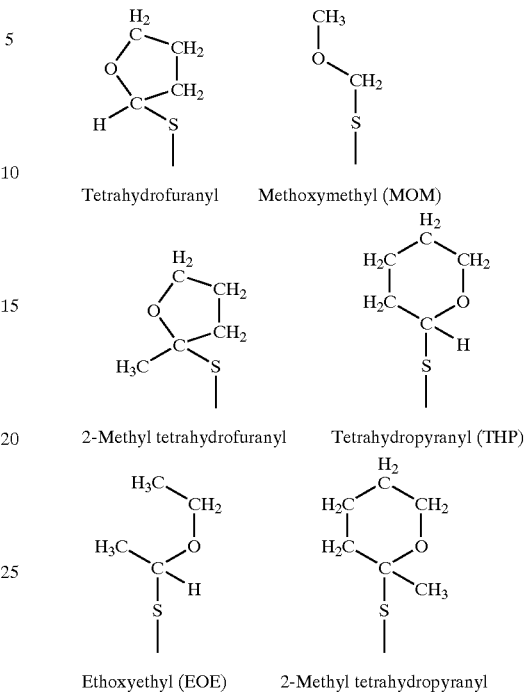

Tetrahydrofuranyl   Methoxymethyl (MOM)

2-Methyl tetrahydrofuranyl   Tetrahydropyranyl (THP)

Ethoxyethyl (EOE)   2-Methyl tetrahydropyranyl

Advantages of using hemithioacetal sulfur protecting groups include the fact that a separate step for removal of the sulfur-protective groups is not necessary. The protecting groups are displaced from the steroid receptor analog during the radiolabeling step, in what is believed to be metal-assisted acid cleavage; i.e., the protective groups are displaced in the presence of the radionuclide at an acidic pH, and the radionuclide is bound by the steroid receptor analog. The radiolabeling procedure thus is simplified, which is especially advantageous when the steroid receptor analogs are to be radiolabeled in a hospital laboratory shortly before use.

In addition, the basic pH conditions and harsh conditions associated with certain known radiolabeling procedures, or procedures for removal of other sulfur protective groups, are avoided. Because basic and/or harsh conditions are avoided, the steroid receptor analogs may incorporate (at sites other than are desirably deprotected) protecting groups and other chemical functionality which should desirably survive the radiolabeling step, but which would decompose under basic and/or harsh conditions. Such base labile groups include any group which may be destroyed, hydrolyzed, or otherwise adversely affected by exposure to basic pH. Certain protein conjugation groups, including activated esters, isothiocyanates, maleimides, and other Michael acceptors, among others, are relatively base labile. Thus, these group may be incorporated into steroid receptor analogs of the invention, and will retain their integrity throughout the radiolabeling procedure of the present invention.

Other preferred sulfur atom protecting groups including ACM and i-PrCO, as defined below:

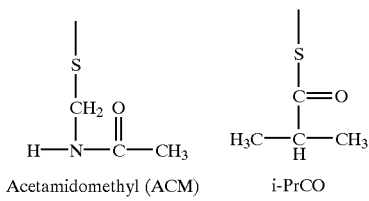

Acetamidomethyl (ACM)    i-PrCO

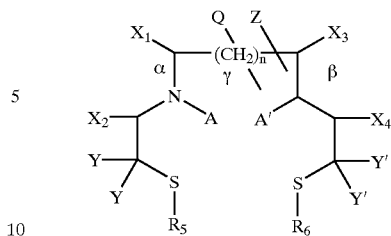

The acetamidomethyl group may be displaced from the steroid receptor analog during radiolabeling conducted at about 50° C. in a reaction mixture having a pH of about 3 to 6. The use of an acetamidomethyl group generally improves the water solubility of the steroid receptor analog, which is desirable in therapeutic and diagnostic applications involving water-based living organisms.

Preferred Steroid Receptor Analogs

In one preferred embodiment, the binding arms of the steroid receptor analog of formulae (I) or (II) may be represented by the following ("$N_3S$" or "$N_2S_2$"):

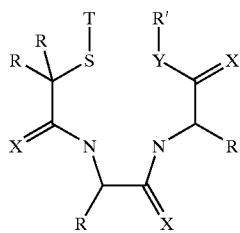

wherein:

T is H or a sulfur protecting group;

each X independently represents $H_2$ or O;

each R independently represents a substituent selected from the group consisting of hydrogen; alkyl; geminal dialkyl; a non-alkyl side chain of an amino acid other than cysteine (alkyl side chains being covered when R is an alkyl group); and —$(CH_2)_r$—Z;

Z represents —COOH or —$NH_2$;

r is an integer of from 1 to about 4; and

R' represents the position at which the metal species binding arm is bonded through

to $C^1$ or $C^2$ in formula (I); and

Y represents N or S.

The sulfur protecting group may be selected from alkyl, aryl, acyl (preferably alkanoyl or benzoyl), thioacyl groups having 1 to about 7 carbons, and organothio groups having 1 to about 10 carbons.

For the R groups, the alkyl groups generally contain from 1 to 7 carbons, preferably from 1 to 4 carbons, and most preferably represent methyl.

In another preferred embodiment, the binding arms have the following structure:

wherein:

$X_1$ and $X_2$ are H or oxo but both are not oxo;

$X_3$ and $X_4$ are H or oxo, but both are not oxo;

One of $X_1$ and $X_3$ is bonded, either directly or indirectly, to $C^1$ or $C^2$ of the compound of formula (I);

A is H, alkyl group of $C_6$ or less, —$CH_2$—$CH_2$—S—$R_1$ or —CO—$CH_2$—S—$R_1$, while in a preferred embodiment, when $X_1$ or $X_2$ is $\square$O, then A is H;

A' is H, alkyl group of $C_6$ or less, —$CH_2$—$CH_2$—S—$R_2$ or —CO——$CH_2$—S—$R_2$, while in a preferred embodiment, when $X_3$ or $X_4$ is $\square$O, then A' is H;

Y is
(a) —$CH_2$—S—$R_3$, or H, when A is H or an alkyl group of $C_6$ or less and A' is H or an alkyl group of $C_6$ or less, or
(b) H;

Y' is
(a) —$CH_2$—S—$R_4$, or H, when A is H or an alkyl group of $C_6$ or less and A' is H or an alkyl group of $C_6$ or less, while in a preferred embodiment, Y and Y' are not both H, or
(b) H;

$R_1$, $R_2$, $R_3$, $R_4$, $R_5$, and $R_6$ are independently selected from sulfur protecting groups;

Q is H or a polar group to increase the hydrophilicity of the compound;

n is 0 to 2; and

Z is —$(W)_m$—R', where W is —$CH_2$—, —$CH_2$—O—, —$CH_2$—CO—, or combination thereof, m is 0 to 5, and R' is a chemically reactive group. In a preferred embodiment, when Z is attached to the carbon designated a there is either no $X_1$ or no Q at α. In another preferred embodiment, when Z is attached to the carbon designated β there is either no $X_3$ or no Q at β. In another preferred embodiment, when $X_1$ is $\square$O there is no Z at α. In another preferred embodiment, when $X_3$ is $\square$O there is no Z at β.

$R_1$, $R_2$, $R_3$, R4, $R_5$ and $R_6$ are independently selected from sulfur protecting groups. Groups which may be used include any of the alkyl, acyl and aryl groups, disulfides and bunte salts known by those skilled in the art. Preferred groups are those that result in the formation of a thioacetal, hemithioacetal, thioester or acetamidomethyl substituent. Particularly preferred groups include p-anisylidine, acetonyl, tetrahydrylfuranyl, ethoxyethyl, tetrahydrylpyranyl, acetamidomethyl and derivatives thereof.

Synthesis of Steroid Analogs

Compounds of formulae (I) and (II) are conveniently prepared by coupling of the "metal species binding arms" $B^1$ and $B^2$ to the core of the molecule which contains the steroid receptor core, including $C^1$, $C^2$ and the $R^1$ and $R^2$ steroid receptor binding groups. The present disclosure, in Examples 1–9, illustrates this synthetic approach to compounds of formulae (I) and/or (II).

Metal Species

The steroid receptor analogs described above may be chelated with one or more metals or metal ions, which are collectively referred to herein as "metal species", to provide useful therapeutic and diagnostic agents.

For diagnostic purposes, preferred metal species which may be chelated according to the invention include gamma emitter isotopes which are useful for diagnostic scintigraphy. Such gamma emitters include, without limitation, gallium[67], gallium[68], indium[111], and technetium[99m] ($^{99m}$Tc). Indium[111] with a half-life of 2.8 days, and technetium[99m] with a half-life of 6 hrs, are particularly useful gamma emitters.

For therapeutic purposes, the steroid analogs according to the invention may be chelated to beta radiation emitters which are useful as cytotoxic agents for radiotherapy. Such emitters include, without limitation, isotopes such as scandium[46], scandium[47], scandium[48], copper[64] ($^{64}$Cu), copper[67] ([67]Cu), gallium[72], gallium[73], yttrium[90] ($^{90}$Y), ruthenium[97] ([97]Ru), palladium[100], rhodium[101m], rhodium[105] ([105]Rh), palladium[109] ([109]Pd), samarium[153], rhenium[186] ([186]Re), rhenium[188] ([188]Re), rhenium[189], gold[198] ([198]Au), gold[199] ([199]Au), radium[212], lead[203] ([203]Pb), and lead[212] ([212]Pb). Of these, [186]Re, [188]Re, and $^{90}$Y are preferred.

The steroid analogs of the invention may also be used to chelate alpha radiation emitting materials such as bismuth212 ([212]Bi) positron emitters such as zirconium[89], fluorescent members of the lanthanide series of elements such as terbium and europium and of the transition series such as ruthenium, and paramagnetic materials such as gadolinium and iron. In addition the analogs of the invention are also suitable for binding numerous other metal ions which may be useful for a variety of purposes, including those in which a catalytic property of the metal ion is of utility. Iron, copper, vanadium, rhodium, platinum, palladium and titanium are examples of metal ions useful in catalyzing a variety of organic reactions, such as the cleavage of nucleic acids by the iron-catalyzed generation of hydroxyl free radicals.

Preferred radionuclides for use in conjunction with a diagnostic kit are $^{99m}$Tc, [97]Ru $^{111}$In and [203]Pb and with a therapeutic kit are [186]Re, [188]Re, $^{90}$Y, [67]Cu, [105]Rh, [198]Au, [199]Au and [212]Bi.

Methods for preparing these isotopes are known. Molybdenum/technetium generators for producing $^{99m}$Tc are commercially available. Procedures for producing [186]Re include the procedures described by Deutsch et al. (*Nucl. Med. Biol.* Vol. 13:4:467–477, 1986) and Vanderheyden et al. (*Inorganic Chem.* Vol. 24:1666–1673, 1985), and methods for production of [188]Re have been described by Blachot et al. (*Int'l J. of Applied Radiation and Isotopes* Vol. 20:467–470, 1969) and by Klofutar et al. (*J. of Radioanalytical Chem.* Vol. 5:3–10, 1970). Production of [109]Pd is described in Fawwaz et al. (*J. Nucl. Med.* 25:796, 1984). Production of [212]Pb and [212]Bi is described in Gansow et al. (*Amer. Chem. Soc. Symp. Ser.* 241:215–217, 1984), and Kozah et al. (*Proc. Nat'l Acad. Sci USA* 83:474–78, 1986).

Steroid Analogs Chelated With Radionuclides

The present invention provides compounds of formulae (I) and (II) in chelation with a radionuclide. The chemical structure of such chelates, which are also referred to herein as radiolabeled analogs, is essentially the same as that of formulae (I) or (II) with the exception that a metal is shown complexing with four electron-donating atoms (i.e., S, O, or N) of the binding arms.

In one embodiment of the invention, the steroid receptor analog is chelated to a radionuclide so as to include the following structure, where any of the "R" groups may be joined, directly or indirectly, to $C^1$ or $C^2$ of the steroid receptor analog.

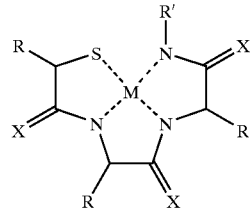

In the above structure, M is a radionuclide ion, to which 1 or 2 oxygen atoms may be bonded (to provide monooxo and dioxo species), or 1 nitrogen atom may be bonded (to provide a nitrido species) especially if the metal is Tc or Re. The radioisotopes $^{99m}$Tc and [186]Re/[188]Re are commercially available as pertechnetate (TcO$_4$) and perrhenate (ReO$_4$) which are in their most stable +7 oxidation state. In order for the donor atoms of the steroid analogs to coordinate with Tc and Re, the pertechnetate and perrhenate have to be reduced to lower oxidation states with reducing agents such as stannous chloride (SnCl$_2$). The donor atom of the steroid analogs of the invention utilizes Tc and Re in their +5 oxidation state.

A variety of metal ions or complex ions may be employed as the radionuclide. These metals include, but are not limited to, copper, e.g., $^{64}$Cu and [67]Cu; technetium, e.g., $^{99m}$Tc; rhenium, e.g., [186]Re and [188]Re; lead, e.g., [203]Pb and [212]Pb; palladium, e.g., [109]Pd; bismuth, e.g., [212]Bi, and gold, e.g., [199]Au. The metal may be present as an ion, e.g., $^{64}Cu^{2+}$ and $^{67}Cu^{2+}$(copper may end up in S-containing ligands as $Cu^+$) or as an oxidized form, e.g., $^{99m}TcO_3^+$, $ReO_3^+$ or $ReO_3^+$ when incorporated in the chelate compounds.

The dashed lines in the formula presented for the chelate compounds of the invention represent four coordinate covalent bonds, between the metal radionuclide M and the sulfur and the three nitrogen atoms shown in the formula. Thus, the metal radionuclide is bound through relatively stable bonds in the chelated compounds of the invention.

Synthesis of Steroid Analogs Chelated with Radionuclides

The steroid receptor analogs of the present invention are radiolabeled, using conventional procedures, with any of a variety of radionuclide metals to form the corresponding radionuclide metal chelates. As set forth above, these radionuclide metals include, but are not limited to, copper (e.g., [67]Cu and $^{64}$Cu); yttrium ($^{90}$Y), technetium (e.g., $^{99m}$Tc); palladium (e.g., [109]Pd), indium (e.g., $^{111}$In), rhenium (e.g., [186]Re and [188]Re); lead (e.g., [212]Pb); and bismuth (e.g., [212]Bi). The selection of suitable chemistry to achieve chelation between a steroid receptor analog and a radionuclide will depend, for example, on the identity of the radionuclide and the presence or absence of protecting groups bound to the atoms which undergo the chelation with the radionuclide. Many aspects of the chemistry of chelation have been described in the prior art, see, e.g., U.S. Pat. Nos. 5,227,474; 5,164,176; 5,120,526; 5,112,953; 5,091,514; 5,075,099; 4,988,496; 4,965,392; and 4,963,688, as well as references cited therein.

In one embodiment of the present invention, steroid receptor analogs of the invention comprising acetamidomethyl and/or hemithioacetal sulfur protective groups are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the steroid receptor analog of the invention.

In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known, see, e.g., U.S. Pat. Nos. 4,440,738; 4,434,151; and 4,652,440. Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}TcO_4^-$ which is in the +7 oxidation level) or sodium perrhenate (i.e., $^{188}ReO_4^-$, $^{186}ReO_4^-$) may be combined simultaneously with a reducing agent and a chelating compound of the invention in accordance with the radiolabeling method of the invention, to form a chelate.

In a preferred embodiment, the radionuclide is treated with a reducing agent and a complexing agent to form an intermediate complex (i.e., an "exchange complex"). Complexing agents are compounds which bind the radionuclide more weakly than do the steroid analogs of the invention, and may be weak chelators. Any of the suitable known complexing agents may be used, including but not limited to gluconic acid, glucoheptonic acid, tartaric acid, methylene disphosphonate, glyceric acid, glycolic acid, mannitol, oxalic acid, malonic acid, succinic acid, bicine, N,N'-bis(2-hydroxy ethyl)ethylene diamine, citric acid, ascorbic acid and gentisic acid. Tartaric acid, gluconic acid or glucoheptonic acid are preferred as the Tc-complexing agent and citric acid for rhenium.

When the radionuclide in the form of an exchange complex is reacted with the steroid analogs of the invention, the radionuclide will transfer to the analog which binds the radionuclide more strongly to form chelates of the invention. Heating may be required to promote transfer of the radionuclide. Radionuclides in the form of such exchange complexes also are considered to be in "chelatable form" for the purposes of the present invention.

Chelates of $^{212}Pb$, $^{212}Bi$, and $^{109}Pd$ may be prepared by combining the appropriate salt of the radionuclide with a steroid analog of the invention, and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation (i.e., in chelatable form). The specific radiolabeling reaction conditions may vary somewhat according to the particular radionuclide and chelating compound involved.

The rhenium chelate may be formed from various routes. For example, reducing perrhenate to rhenium (IV) hexachloride by employing hypophosphorous acid and concentrated HCl at 95° C. yields rhenium hexachloride. The rhenium hexachloride may then be converted to rhenium dioxo diethylenediamine chloride in 90% ethylenediamine at room temperature. At a basic pH in the presence of the steroid receptor analogs of the invention, the rhenium dioxo diethylenediamine chloride exchanges rapidly with, for example, a binding arm having the $N_3S$ configuration of chelating atoms.

$^{99m}Tc$-radiolabeling of steroid analogs with N and/or S atoms in the binding arms may be accompanied by the following Methods A or B.

Method A: Stannous gluconate kits are prepared containing 5.0 mg sodium gluconate, 0.1 mg stannous chloride, 0.1–1.0 mg of steroid analog with N,S-binding arms, and 1.0–5.0 mg of lactose. The pH of the solution is maintained between 5 and 7.5 using hydrochloric acid, acetic acid or sodium hydroxide. To the stannous gluconate kit is added 1.0 mL sodium pertechnetate ($Na^{+99m}TcO_4^-$) in saline with a specific activity of 35–50 mCi/mL. The vial is thoroughly mixed and incubated at 25° C.–100° C. for 15–30 minutes. The percent formation of $^{99m}Tc$-chelate is determined by ITLC and HPLC using a radiometric detection system.

Method B: Stannous tartrate kits are prepared in an evacuator vial under nitrogen to contain 0.5 mL of disodium tartrate (10 mg/mL) and 0.1 mL stannous chloride (1.0 mg/mL in ethanol). The pH of the solution is kept between 5 and 7.5 preferably 6.5. To this stannous tartrate solution is added 1.0 mL of sodium pertechnetate at a specific concentration of 35–50 mCi/mL in saline. The reaction mixture is allowed to stand at room temperature. In another evacuated vial, 200 μL of sodium phosphate (0.5 M, pH 8.0 or 10.0) and 1.0 mL of $N_4$ steroid receptor analog (1.0 mg/mL) are added successively. Then Tc-99m-Tartrate (50 mCi) is added, and the vial is incubated at 25° C.–100° C. for 10–30 min. The percent formation of radiolabeled $N_4$-steroid receptor analog is determined by ITLC and HPLC using a radiometric detection system.

The following general method may be used to radiolabel steroid analogs having protected sulfur atoms in their binding arms with $^{186}Re$: a solution of 11.0 mg of citric acid 370 pg of gentisic acid and 460 pg of stannous chloride dihydrate in 100 μL $H_2O$ is adjusted to a final pH of 2. To this solution, 500 μL of $^{186}ReO_4$ (1–50 mCi) is added and incubated for 1–2 minutes to form $^{186}Re$-citrate. Immediately following, hemithioacetal protected steroid receptor analog (0.1 to 1.0 mg in 600 μL isopropanol) is added. The reaction mixture is incubated at 90–100° C. for 15–30 min and then is brought to room temperature by rapid cooling in an ice bath.

The following general method may be used to radiolabel steroid analogs having unprotected sulfur atoms in their binding arms with $^{186}Re$ (in general, a slightly higher pH is used when the sulfur atoms are in unprotected form vs. when the sulfur atoms are in protected form): a solution of 11.0 mg of citric acid 370 μg of gentisic acid and 460 μg of stannous chloride dihydrate in 100 μL $H_2O$ is adjusted to a final pH of 2. To this solution, 500 μL of $^{186}ReO_4$ (1–50 mCi) is added and incubated for 1–2 minutes to form $^{186}Re$-citrate. In another evacuated vial, 200 μL of sodium phosphate (0.5 M, pH 8.0) and 1.0 mL of the steroid receptor analog (0.5–1.0 mg/mL) are added successively. Then $^{186}Re$-citrate (50 mCi) is added, and the vial is incubated at 25–100° C. for 10–30 min. The percent information of radiolabeled analog is determined by ITLC and a gradient HPLC system using a radiometric detector.

The following general method may be used to radiolabel steroid analogs having protected sulfur atoms in their binding arms with $^{188}Re$: sodium perrhenate (3 mL, 15 mCi, produced from a W-188/Re-188 research scale generator) is added to a vial containing lyophilized mixture comprising citric acid, 75 mg; stannous chloride, 0.75 mg; gentisic acid, 0.25 mg; and lactose, 100 mg. The vial is agitated gently to mix the contents, then incubated at room temperature for 10 minutes to form a $^{188}$Re-citrate intermediate exchange complex. To a separate vial containing 0.50–1.0 mg of the steroid receptor analog comprising a hemithioacetate(ethoxyethyl) sulfur protecting group, 0.5 mL of isopropyl alcohol is added and the vial is agitated for 2 min for complete dissolution of the ligand. Next, 0.3 mL of this solution is transferred to the vial containing the $^{188}$Re-citrate complex prepared above. After gentle mixing, the vial is incubated at 95–100° C. for 15–30 min. Then, immediately transferred to a 0° C. ice bath for two minutes. The yields of $^{188}$Re-analog generally range between 90–95% as measured by reverse phase $C_{18}$ HPLC analysis.

The following general method may be used to radiolabel steroid analogs having unprotected sulfur atoms in their binding arms with $^{186}$Re (in general, a slightly higher pH is used when the sulfur atoms are in unprotected form vs. when the sulfur atoms are in protected form): sodium perrhenate (3 mL, 15 mCi, produced from a W-188/Re-188 research scale generator) is added to a vial containing lyophilized mixture comprising citric acid, 75 mg; stannous chloride, 0.75 mg; gentisic acid, 0.25 mg; and lactose, 100 mg. The vial is agitated gently to mix the contents, then incubated at room temperature for 10 minutes to form a $^{188}$Re-citrate intermediate exchange complex. In another evacuated vial, 200–500 μL of sodium phosphate (0.5 M, pH 8.0) and 1.0 mL of steroid receptor analog (0.5–1.0 mg/mL) are added successively. Then $^{188}$Re-citrate (50 mCi) is added, and the vial is incubated at 25° C.–100° C. for 10–30 min. The percent formation of radiolabeled analog is determined by ITLC and a gradient HPLC system using a radiometric detector.

Compositions Containing Steroid Receptor Analogs and Radionuclide Chelates Thereof The present invention provides a pharmaceutical or veterinary composition (hereinafter, simply referred to as a pharmaceutical composition) containing a steroid receptor analog as described above, in admixture with a pharmaceutically acceptable carrier or diluent. The invention further provides a pharmaceutical composition containing a chelate of a steroid receptor analog as described above, in admixture with a pharmaceutically acceptable carrier or diluent.

The pharmaceutical compositions of the present invention may be in any form which allows for the composition to be administered to a subject. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical composition of the invention are formulated so as to allow the active ingredients contained therein to be bioavailable upon administration of the composition to a subject. Compositions that will be administered to a subject take the form of one or more dosage units, where for example, a tablet may be a single dosage unit, and a container of steroid in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a steroid receptor analog or chelate thereof as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the inventive analog or chelate such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active steroid compound. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the active steroid analog component(s) or chelate thereof and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of asthma, allergy, inflammation (including arthritis) or thrombosis.

The pharmaceutical compositions may be prepared by methodology well known in the pharmaceutical art. Various steroid compounds are, and have been widely used as active ingredients in pharmaceutical composition intended for therapeutic use, and accordingly one of ordinary skill in the art is familiar with preparing such compositions. The steroid analog compounds of the present invention, as well as the chelates thereof may be formulated into pharmaceutical compositions in a like manner.

A composition intended to be administered by injection can be prepared by combining the steroid analog or chelate thereof with water so as to form a solution. A surfactant may be added to facilitate the formation of a homogeneous solution or suspension. Surfactants are compounds that non-covalently interact with the steroid analog/chelate so as to facilitate dissolution or homogeneous suspension of the steroid analog/chelate in the aqueous delivery system.

An effective amount of a compound or composition of the present invention is used to detect, diagnose or treat diseases of cells having steroid receptors. These cells are typically mammalian cells. Methods of administering effective amounts of the analogs or chelates are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multidose inhalation devices. The dosage amount and frequency are selected to create an effective level of the agent without harmful effects. It will generally range from a dosage of about 0.1 to 100 mg/Kg/day, and typically from about 0.1 to 10 mg/Kg/day where administered orally or intravenously. Also, the dosage range will be typically from about 0.01 to 1 mg/Kg/day where administered intranasally or by inhalation.

Therapeutic Applications of Steroid Analogs Chelated with Radionuclides

Yet another embodiment of the invention provides methods for using the steroid analogs chelated with radionuclide as described above for therapeutic purposes. The therapeutic method may be used for delivering a radionuclide to a target site within a mammalian host. The method comprises the step of administering to a mammal a therapeutically effective dose of one of the radiolabeled analogs as described above. A therapeutically effective dose is generally from about 20 mCi to about 300 mCi. Preferred radionuclides are $^{186}$Re, $^{188}$Re, $^{67}$Cu, $^{105}$Rh, $^{198}$Au, $^{199}$Au and $^{212}$Bi. A preferred mammal is man.

The chelates of the present invention may be administered to a mammalian host, normally by injection, intravenously, intraarterially, peritoneally, intratumorally, or the like, depending upon the particular site at which the radionuclide is desired. Generally, from about 0.1 to 2 ml will be injected into a host, depending upon the size of the host, with about 0.001 to 50 $\mu$Ci/Kg of host. For human hosts, the dosage will usually be about 10–50 mCi/70 Kg host, more usually about 25–35 mCi/70 Kg host. For lower mammals, e.g., mice, 1–50 $\mu$Ci will be used for biodistribution studies, while up to or greater than 500 $\mu$Ci will be used for imaging studies. After administration of the radionuclide, depending upon its purpose, the host may be treated in various ways for detection of the radioactive emissions from the site or sites where the radionuclide specifically binds.

Diagnostic Applications of Steroid Analogs Chelated with Radionuclides

Yet another embodiment of the invention provides methods for using the radiolabeled analogs described above for diagnostic purposes. The diagnostic method may be used to detect the presence or absence of a target site within a mammalian host. The method comprises the steps of administering to a mammal a diagnostically effective dose of one of the radiolabeled analogs described above. This step is followed by a step of detecting the biodistribution of the radionuclide in the mammal to determine the presence or absence of the target site in the host.

A diagnostically effective dose of a radiolabeled analog is generally from about 5 to about 35 and typically from about 10 to about 30 mCi per 70 Kg body weight. The precise dose for a radiolabeled analog is dependent upon the particular receptor which is being targeted because the level of uptake of a radiolabeled analog into a tumor is dependent upon the number of receptors for the analog and its affinity for the receptors. The precise dose further depends upon the particular route of administration, e.g., intravenous, intracompartmental, intraarterial or intratumoral. It will be evident to one skilled in the art how to determine the optimal effective dose for a particular radiolabeled analog and a particular route of administration. Preferred radionuclides are $^{97}$Ru, $^{99m}$Tc and $^{203}$Pb. A preferred mammal is man.

The therapeutic method may be used for delivering a radionuclide to a target site within a mammalian host. The method comprises the step of administering to a mammal a therapeutically effective dose of one of the radiolabeled analogs described above. A therapeutically effective dose is generally from about 20 mCi to about 300 mCi. Preferred radionuclides are $^{186}$Re, $^{188}$Re, $^{67}$Cu, $^{105}$Rh, $^{198}$Au, Au and $^{212}$Bi. A preferred mammal is man.

The chelates of the present invention may be administered to a mammalian host, normally by injection, intravenously, intraarterially, peritoneally, intratumorally, or the like, depending upon the particular site at which the radionuclide is desired. Generally, from about 0.1 to 2 ml will be injected into a host, depending upon the size of the host, with about 0.001 to 50 $\mu$Ci/Kg of host. For human hosts, the dosage will usually be about 10–50 mCi/70 Kg host, more usually about 25–35 mCi/70 Kg host. For lower mammals, e.g., mice, 1–50 $\mu$Ci will be used for biodistribution studies, while up to or greater than 500 $\mu$Ci will be used for imaging studies. After administration of the radionuclide, depending upon its purpose, the host may be treated in various ways for detection of the radioactive emissions from the site or sites where the radionuclide specifically binds.

Kits Containing Steroid Analogs, and Preparation and Uses Thereof

In another embodiment of the invention, a steroid receptor analog as described above may be included in a kit for producing a metal species-chelated steroid receptor analog of the invention (a "radiolabeled analog") for radiopharmaceutical use. Reagents useful in reactions to radiolabel the steroid receptor analog with a radionuclide may be included. Such kits also may comprise a means for purifying the radiolabeled analog away from the reaction mixture in which it was formed, as well as specific instructions for producing the radiolabeled analog using the kit components.

Such kits generally will be used in hospitals, clinics or other medical facilities. Since such facilities generally have ready access on a daily basis to radionuclides, including isotopes of technetium, and since isotopes of rhenium, lead, bismuth, palladium, and copper may be prepared as described above, inclusion of the radionuclide in the kit is optional. Exclusion of the radionuclide permits storage of the kit, whereas kits containing the radionuclide (either as a separate component or as the radiolabeled analog) would have to be used within a narrow time frame (depending on the half-life of the particular isotope); otherwise, radioactive decay of the radioisotope would diminish the effectiveness of the diagnostic or therapeutic technique for which the radiolabeled analog is used. For $^{186}$Re, on-site radiolabeling would avoid radiolytic degradation of the labeled analog due to the beta particle emission.

The kits may be diagnostic or therapeutic kits, depending on which radionuclide is used for chelating with the steroid receptor analog. When the radionuclide is to be reduced to a lower oxidation state (e.g., technetium and rhenium, as discussed above), the kits may contain a reducing agent which is effective in reducing a particular metal radionuclide, which is to be chelated by the steroid receptor analog, to an oxidation state at which an exchange complex of the radionuclide may be formed. In addition, a kit may additionally contain a complexing agent with which the reduced radionuclide will form an exchange complex, where this exchange complex is a useful intermediate in forming the radiolabeled analog.

The kit components and instructions will be somewhat different when the steroid receptor analog is to be radiolabeled with a technetium isotope (i.e., a diagnostic kit) than when the chelating agent is to be radiolabeled with a rhenium, lead, bismuth, palladium, or copper isotope (i.e., a therapeutic kit). The different components and procedures are discussed in more detail below. In the following discussion, the term "separate containers" is meant to include not only separate, individual containers (e.g., vials) but also physically separate compartments within the same container.

In accordance with one embodiment of the invention, a diagnostic kit comprises the following reagents (in separate containers unless otherwise noted), presented in the general order of use.

1. A reducing agent effective in reducing pertechnetate ($^{99m}$TcO$_4^-$ which is in the +7 oxidation level) to a lower oxidation state at a neutral to acidic pH so that a technetium exchange complex can be formed. Many suitable reducing agents are known in the art, including but not limited to stannous ion, (e.g., in the form of stannous salts such as stannous chloride or stannous fluoride), metallic tin, formamidine sulfinic acid, ferric chloride, ferrous sulfate, ferrous ascorbate, and alkali salts of borohydride. Preferred reducing agents are stannous salts.

2. A complexing agent with which the reduced $^{99m}$Tc will form an exchange complex, thus protecting the $^{99m}$Tc from hydrolysis. In order to achieve efficient transfer or exchange of the $^{99m}$Tc from this complex to the steroid receptor analog, the complexing agent advantageously binds the radionuclide more weakly than the analog will. Complexing agents which may be used include, but are not limited to, gluconic acid, glucoheptonic acid, methylene diphosphonate, glyceric acid, glycolic acid, mannitol, oxalic acid, malonic acid, succinic acid, bicine, N,N'-bis(2-hydroxyethyl)ethylene diamine, citric acid, ascorbic acid and gentisic acid. Good results are obtained using gluconic acid or glucoheptonic acid as the Tc-complexing agent (or "exchange agent" in these cases), as they efficiently transfer the $^{99m}$Tc to the steroid receptor analog at a pH at which the active ester is stable.

3. A steroid receptor analog as described above.

4. Additional reagents for use in the radiolabeling are optional components of the kits. Examples of such additional reagents include, without limitation, buffers, alcohols, acidifying solutions, and other such reagents as are more fully described herein. Such additional reagents are generally available in medical facilities and thus are optional components of the kit because they can be readily obtained by people using the kits. However, these reagents preferably are included in the kit to ensure that reagents of sufficient purity and sterility are used, since the resulting radiolabeled analogs may be administered to mammals, including humans, for medical purposes.

5. Optionally, a container of steroid receptor analog, which may be administered in non-radiolabeled form to a human or mammal, is included in the kit. This steroid receptor analog is reactive with essentially the same target sites as the radiolabeled analog and reduces binding of the radiolabeled analog to cross-reactive binding sites on non-target tissues. The two analogs may be the same, or the analog to be radiolabeled may, for example, be somewhat different from the analog a which is to be administered in non-radiolabeled form. The latter steroid receptor analog is administered as an unlabeled specific blocker (prior to administration of the radiolabeled analog) in an amount effective in improving diagnostic imaging of the desired target sites (e.g., tumors as described above).

6. Optionally, the kit may also include a container of a steroid receptor analog which does not bind through specific mechanisms to sites within the human or mammal to which the radiolabeled analog is to be administered. This steroid receptor analog is administered as an "irrelevant" analog (prior to administration of the radiolabeled analog) in an amount effective in decreasing nonspecific uptake of certain radiolabeled analogs, as described above.

In one embodiment of the invention, a radiolabeled analog may be produced using a kit as described above, according to the following general procedure. The procedure is preferably conducted under sterile conditions. In this particular embodiment of the invention, the kit includes reagents in amounts suitable for preparation of an amount of radiolabeled analog suitable for injection into one human for diagnostic purposes.

An aqueous solution containing a reducing agent and a complexing agent (each as described above) is prepared. The solution may be prepared, for example, by combining stannous chloride dihydrate (which includes the stannous ion reducing agent) and sodium gluconate (a complexing agent) to form a stannous gluconate complex. This stannous gluconate complex may be provided in a single container in the kit. In one embodiment of the invention, the stannous gluconate complex is provided in the kit in dry solid form.

Optionally, one or more stabilizer compounds may be added to the stannous gluconate complex. Many such stabilizer compounds are known in the art, and some are discussed in connection with the therapeutic kits below. For example, gentisic acid may be added to a container of the stannous gluconate complex to stabilize (minimize oxidation of) the stannous ion reducing agent, and the resulting mixture may be provided in the kit in dry solid form or as a lyophilized preparation. A filler compound advantageously is added prior to lyophilization, as described for the therapeutic kit below. For example, lactose may be added as a filler compound in an amount effective to facilitate lyophilization. The amounts of stannous chloride and sodium gluconate preferably are not so large as to have adverse effects on the desired reactions and product. For example, an excessively large amount of free sodium gluconate may slow the transchelation step and require addition of excessive amounts of buffer necessary to raise the pH in subsequent steps, and the reaction mixtures would then be undesirably dilute. An acceptable ratio of stannous chloride dihydrate to sodium gluconate (by weight) is from about 1:10 to about 1:100, preferably from about 1:25 to about 1:70, most preferably about 1:41.6.

The amount of $^{99m}$Tc added may vary. When the diagnostic kit is designed for preparation of a radiolabeled analog to be injected into a single human patient, the amount of pertechnetate to be added to the following reaction mixture may be from about 50 to about 200 mCi, preferably from about 75 to about 100 mCi of the radionuclide. Greater amounts may interfere with the reaction and produce low yields, as well as generating an excessive amount of radioactivity for administration to a single patient. When about 75 to 100 mCi of $TcO_4^-$ are to be added, the stannous gluconate complex preferably is formed from about 3 to about 10 mg of sodium gluconate and about 0.075 to about 0.250 mg of stannous chloride dihydrate; preferably from about 4 to about 6 mg of sodium gluconate and about 0.075 to about 0.125 mg of stannous chloride dihydrate.

Using the reagents described above, sodium pertechnetate is combined with the reducing agent and complexing agent. When the sodium pertechnetate is added to stannous gluconate, the radionuclide is effectively reduced to a lower oxidation state and complexed with gluconate to form an exchange complex. The stannous gluconate and pertechnetate may be combined in various ways. In one embodiment of the invention, sterile water is added to a vial containing a stannous gluconate preparation in dry solid form. A portion of the resulting solution is combined with about 0.75 mL sodium pertechnetate (about 75 to 100 mCi). In another embodiment of the invention, sodium pertechnetate (about 1 mL) is added directly to a lyophilized preparation comprising stannous gluconate, gentisic acid as a stabilizer, and lactose as a filler compound. In either case, the reaction mixture is incubated at about 25° C. to about 50° C., preferably at about 25° C. to about 3° C. for a minimum of 10 minutes. Incubation for 10 minutes generally gives sufficient yields of the desired technetium exchange complex (e.g., technetium gluconate) while minimizing the formation of insoluble technetium dioxide, which may increase with increased incubation time.

A steroid receptor analog of the invention is added to an organic solvent which is effective in dissolving the analog and effective for the exchange reaction that follows. Suitable solvents should be nontoxic in mammals and inert toward the reactants in the reaction mixture. Organic solvents which may be used include, without limitation, acetonitrile, ethyl acetate, and methylethyl ketone. When the radiolabeled analog is to be injected into humans, however, suitable organic solvents include, but are not limited to, alcohols such as ethanol, butanol, tert-butyl alcohol and propanol, and polar aprotic solvents such as DMSO and dimethylformamide (DMF). The choice of solvent may vary according to the particular steroid receptor analog included in the kit. For example, when the steroid receptor analog includes a tetrafluorophenyl ester group, ethanol may react with the ester in a transesterification reaction, producing ethyl ester as a by-product. A preferred organic solvent is isopropyl alcohol. The concentration of the organic solvent in the following Tc-labeling exchange reaction mixture should be between about 10% and about 30%, preferably between about 15% and about 25%.

The solution comprising the steroid receptor analog in the organic solvent is then acidified to a pH of about 2.0 to about 5.0, preferably 2.8 to 3.3. At these acidic pH conditions, the formation of insoluble $TcO_2$ will be minimized. Also, in this pH range, any hemithioacetal or thioacetal sulfur-protecting groups present in the steroid receptor analog will be displaced by a metal-assisted acid cleavage during the technetium labeling exchange reaction to form the corresponding technetium chelate compound. Also, hydrolysis of ester groups on the steroid receptor analog is minimized under acidic conditions when compared to basic conditions. Suitable acids are added in amounts sufficient to displace the sulfur-protective groups, if present, in the presence of the metal radionuclide (i.e., in amounts sufficient to adjust the reaction mixture to the above-described pH values range). Suitable acids include, but are not limited to, phosphoric acid, sulfuric acid, nitric acid, glacial acetic acid, hydrochloric acid and combinations thereof. Also included are solutions including such acids and buffers (e.g., acetate and phosphate buffers). A solution including glacial acetic acid and 0.2 N HCl at a ratio of 2:14 is a typical acid solution in the present invention.

The acidified solution of steroid receptor analog is combined with the previously prepared technetium exchange complex solution, to form the corresponding radiolabeled analog. Typically, about 100 μg to about 150 μg, preferably about 135 μg of steroid receptor analog is combined with the Tc-gluconate complex prepared from the 75 to about 100 mCi of technetium as described above. The reaction mixture is heated to between about 50° C. and 100° C. for a time ranging from about 5 minutes to about 45 minutes. Typically, the desired radiolabeled analog may be produced by heating at about 75° C. for about 15±2 minutes. Heating the reaction mixture accelerates the exchange reaction to form the chelate between the steroid receptor analog and the radionuclide. Upon completion of the reaction, the mixture is transferred immediately to a 0° C. ice bath for a minimum of 2 minutes to stop the reaction quickly and at this temperature the radiopharmaceutical is stable. For practical purposes, the radiopharmaceutical can be stored at room temperature for several hours.

An aqueous solution including a buffer may then be added to the reaction mixture in order to reduce the concentration of the organic solvent(s) and to adjust the pH as desired. Suitable buffers include nontoxic buffers which are inert toward the reactants, such as, but not limited to, sodium phosphate buffer and sodium bicarbonate buffer, preferably at a concentration of about 1.0 M and a pH of about 10. Buffers such as TRIS must be used cautiously because the free amine groups of TRIS are reactive with ester groups that may be present as part of the steroid receptor analog. Sufficient buffer is added to reduce the organic solvent concentration to an amount ranging from about 10% to about 15%, preferably from about 7.5% to about 12.5% (on a weight basis, based on the entire weight of reaction product solution).

In accordance with another embodiment of the invention, a therapeutic kit includes the following reagents.

1. A reducing agent effective in reducing $ReO_4^-$, which is in the +7 oxidation level, to a lower oxidation state at a neutral to acidic pH so that a rhenium exchange complex can be formed. Many suitable reducing agents for this purpose are known in the art, including but not limited to stannous ion (e.g., in the form of stannous salts such as stannous chloride or stannous fluoride), metallic tin, formamidine sulfinic acid, ferric chloride, ferrous sulfate, ferrous ascorbate, and alkali salts of borohydride. Preferred reducing agents are stannous salts.

2. A complexing agent with which the reduced Re will form an exchange complex, thus protecting the Re from hydrolysis. In order to achieve efficient transfer or exchange of the Re from this complex to the steroid receptor analog, the complexing agent advantageously binds the radionuclide more weakly than the steroid receptor analog will. Complexing agents which may be used include, but are not limited to, methylene diphosphonate, glyceric acid, glycolic acid, mannitol, oxalic acid, malonic acid, succinic acid, bicine, N,N'-bis(2-hydroxyethyl)ethylene acid, succinic diamine, citric acid, ascorbic acid, gentisic acid, tartaric acid, and gluconic acid. A preferred complexing agent is citric acid, which may be used to form a Re-complexing agent complex (or "exchange agent" in these cases).

3. A steroid receptor analog of the invention as described above.

4. Additional reagents for use in the radiolabeling are optional components of the kits. Examples of such additional reagents include, without limitation, buffers, alcohols, acidifying solutions, and other such reagents as are more fully described herein. Such additional reagents are generally available in medical facilities and thus are optional components of the kit because they can be readily obtained by people using the kits. However, these reagents preferably are included in the kit to ensure that reagents of sufficient purity and sterility are used, since the resulting radiolabeled analogs may be administered to mammals, including humans, for medical purposes.

5. Optionally, a container of steroid receptor analog, which may be administered in non-radiolabeled form to a human or mammal, is included in the kit. This steroid receptor analog is reactive with essentially the same target sites as the radiolabeled analog and reduces binding of the radiolabeled analog to cross-reactive binding sites on non-target tissues. The two analogs may be the same, or the analog to be radiolabeled may, for example, be somewhat different from the analog which is to be administered in non-radiolabeled form. The latter steroid receptor analog is administered as an unlabeled specific blocker (prior to administration of the radiolabeled analog) in an amount effective in improving diagnostic imaging of the desired target sites (e.g., tumors as described above).

6. Optionally, the kit may also include a container of a steroid receptor analog which does not bind through specific mechanisms to sites within the human or mammal to which the radiolabeled analog is to be administered. This steroid receptor analog is administered as an "irrelevant" analog (prior to administration of the radiolabeled analog) in an amount effective in decreasing nonspecific uptake of certain radiolabeled analogs, as described above.

In one embodiment of the invention, a steroid receptor analog radiolabeled with either $^{188}$Re or $^{186}$Re may be prepared using such a kit, according to the following general procedure. The procedure is conducted under sterile conditions.

Perrhenate (the $ReO_4^-$ form of the 186Re or 188Re isotope) is reacted with a reducing agent and a complexing agent. For instance, citric acid (a complexing agent) may be combined with stannous chloride (a reducing agent) in a single container (in which a stannous citrate complex is believed to form) and the perrhenate may then be added thereto.

The amounts of stannous chloride and citric acid added should not be so large as to have adverse affects on the desired reactions. For example, an excessively large amount of free citric acid may lower the pH to a level which makes addition of large quantities of buffer necessary to raise the pH in subsequent steps, and the reaction mixtures would be undesirably dilute. An acceptable ratio of stannous chloride to citric acid (by weight) generally ranges from about 1:10 to about 1:500, preferably from about 1:20 to about 1:200, most preferably about 1:100.

One or more stabilizer compounds may be added to the stannous citrate complex. Many such stabilizer compounds are known. See, for example, U.S. Pat. Nos. 4,440,738 and 4,510,125. Advantageously, gentisic acid is added to the stannous citrate to stabilize (e.g., to prevent oxidation of) the stannous ion. The stabilizer is added to a solution including the stannous chloride reducing agent (and the complexing agent) in an amount effective to stabilize the stannous ion so that the shelf life (stability) of the stannous ion is increased. The solution may be lyophilized and provided in the kit as a lyophilized powder.

When the stannous citrate solution is to be lyophilized, a "filler compound" may be added to the solution to provide bulk or mass and to aid in the lyophilization process. Lactose is a suitable filler compound.

In one particular embodiment of the invention, an aqueous solution of stannous citrate may be prepared by combining about 75 mg citric acid with about 750 $\mu$g stannous chloride. About 250 $\mu$g gentisic acid may then be added. Typically, as the amount of gentisic acid decreases, the stabilizing effect was not as efficient, whereas when the amount of gentisic acid increases there is a negative affect on yields. About 100 mg lactose (a preferred amount) may then be added to the preparation, although about 20 mg is typically adequate. The final solution (about 2 mL volume) may then be lyophilized.

Perrhenate may then be added to the stannous citrate preparation. Perrhenate may be introduced into the preparation as an aqueous solution of the sodium salt (e.g., eluted from a rhenium generator) or as an aqueous solution of the tetrabutylammonium ion pair. Either way, perrhenate is incubated with a solution that includes a reducing agent and a complexing agent. The reaction mixture is incubated at a temperature ranging from about 25° C. to about 50° C., preferably at about 25° C. to 37° C., for a minimum of 10 minutes. Incubation for 10 minutes generally gives sufficient yields of the desired rhenium exchange complex (e.g., rhenium-citrate), while minimizing the formation of insoluble rhenium dioxide.

A steroid receptor analog of the invention, which may contain thioacetal or hemithioacetal sulfur-protecting groups, may then be dissolved in an organic solvent which is both effective in dissolving the steroid receptor analog and is suitable for the exchange reaction that follows. Suitable solvents should be non-toxic in mammals and inert toward the reactants in the reaction mixture. Organic solvents which may be used include, without limitation, acetonitrile, ethyl acetate, and methyl ethyl ketone. When the radiolabeled analog is to be injected into humans, however, suitable organic solvents include but are not limited to alcohols such as ethanol, butanol, tert-butyl alcohol, and propanol and polar aprotic solvents such as DMSO and dimethylformamide (DMF). The choice of solvent may vary according to the particular steroid receptor analog included in the kit. For example, when the steroid receptor analog includes a tetrafluorophenyl ester group, ethanol may react with the ester in a transesterification reaction, producing ethyl ester by-products which are undesirably lipophilic. A preferred organic solvent is isopropyl alcohol.

The solution which includes the steroid receptor analog in the organic solvent may be combined with the rhenium exchange complex solution prepared above, to form the corresponding rhenium-chelated steroid receptor analog. Typically, the reaction is advantageously conducted at a pH of from about 1.5 to about 5.0, preferably from about 1.7 to about 2.0. At these acidic pH conditions, the formation of insoluble $ReO_2$ will be minimized; and as explained above, hemithioacetal and thioacetal sulfur-protecting groups (if present) will be displaced by a metal-assisted acid cleavage during the rhenium labeling exchange reaction to form the corresponding rhenium chelate compound. Also, hydrolysis of ester groups on the steroid receptor analog is minimized under acidic conditions when compared to basic conditions. If adjustment of the pH of the reaction mixture is necessary, suitable acids may be added in amounts sufficient to displace the sulfur-protective groups in the presence of the metal radionuclide (i.e., in amounts sufficient to adjust the reaction mixture to the above-described pH values range). Suitable acids include, but are not limited to, phosphoric acid, sulfuric acid, nitric acid, glacial acetic acid, hydrochloric acid, and combinations thereof. Also included are solutions comprising such acids and buffers (e.g., acetate and phosphate buffers).

The amount of steroid receptor analog reacted with the Re-citrate intermediate may vary according to the reaction volume, which in turn varies according to the volume in which perrhenate was added in an earlier step (e.g., perrhenate may be added as an eluent from the generator or may first be concentrated). In one embodiment of the invention, the concentration of chelating compound in the reaction mixture (in which the chelate is formed) ranges from about 100 $\mu$g to about 200 $\mu$g of steroid receptor analog per mL of reaction mixture.

To accomplish chelation of the steroid receptor analog, the reaction mixture may be heated to a temperature between about 50° C. and 100° C. for a time of from about 5 to about 45 minutes. Typically, heating at about 75° C. for about 10 minutes is sufficient. Upon completion of the reaction, the mixture may be transferred immediately to a 0° C. ice bath for a minimum of 2 minutes in order to stop the reaction and is stable at 0° C. to 25° C. for several hours.

The following examples are provided for purposes of illustration, not limitation.

EXAMPLES

Example 1

Synthesis of $N_2S_2$ Chelating Agent 9

Synthesis of Diamine 6

Diamine 6 is prepared according to the scheme shown in FIG. 1A and the following description, which refers to compounds by their numbers as set forth in FIG. 1A.

To a solution of desoxyanisoin 1 (1.95 mmol) in EtOH (5 mL) is added hydroxylamine hydrochloride (7.20 mmol) followed by pyridine (0.5 mL). The mixture is heated to reflux for 1 hour then cooled and concentrated in vacuo. Water (5 mL) is added. The resulting suspension is stirred for 15 min and then filtered. The filter cake is washed with additional water (2×5 mL) then allowed to air dry. The collected white solid (oxime 2) is of sufficiently high purity to be used in subsequent steps without additional purification.

To a stirred suspension of LAH (2.24 mmol) in THF (2 mL) is added, dropwise, a solution of oxime 2 (0.56 mmol) in THF (2 mL). The mixture is allowed to stir under nitrogen at room temperature for 12 hours. The mixture is cooled in ice water and excess LAH is consumed by the careful, dropwise, addition of water. The resulting precipitate is removed by filtration through glass fiber filter paper and washed with ether (3×5 mL). The washings are combined with the original filtrate, dried over sodium sulfate and concentrated in vacuo. The resulting oil is then chromatographed on silica gel (eluting solvent:ethyl acetate/hexane) to give aziridine 3.

To a solution of aziridine 3 (1 mmol) in acetonitrile (5 mL) is added di-tert-butyl dicarbonate (1.1 mmol) followed by triethylamine (0.5 mL). The mixture is stirred at room temperature under nitrogen for 16 hours then concentrated in vacuo. The resulting oil is dissolved in ethyl acetate and washed with 1N aqueous HCl and brine. Drying over magnesium sulfate and concentration yields the N-BOC aziridine 4.

A mixture of N-BOC aziridine 4 (1 mmol) and tetrabutylammonium cyanide (1 mmol) in methylene chloride (5 mL) is heated to reflux for 12 hours. The reaction mixture is then cooled to room temperature concentrated and chromatographed ($SiO_2$, ethyl acetate/hexane) to give nitrile 5.

A solution of nitrile 5 (0.5 mmol) in THF (2 mL) is added dropwise to a solution of LAH (2 mmol) in THF (2 mL). The mixture is refluxed for 1 hour then cooled in ice water and excess LAH is consumed by the careful, dropwise, addition of water. The resulting precipitate is removed by filtration through glass fiber filter paper and washed with ether (3×5 mL). The washings are combined with the original filtrate, dried over sodium sulfate and concentrated in vacuo. The resulting oil is then dissolved in methylene chloride (10 mL) and 4N HCl in dioxane is added dropwise (10 mmol). After stirring for one hour the solution is concentrated in vacuo to give diamine 6 which is purified by chromatography ($SiO_2$, triethylamine/methanol/methylene chloride).

Synthesis of $N_2S_2$ Chelating Agent 9

Figure 1B:
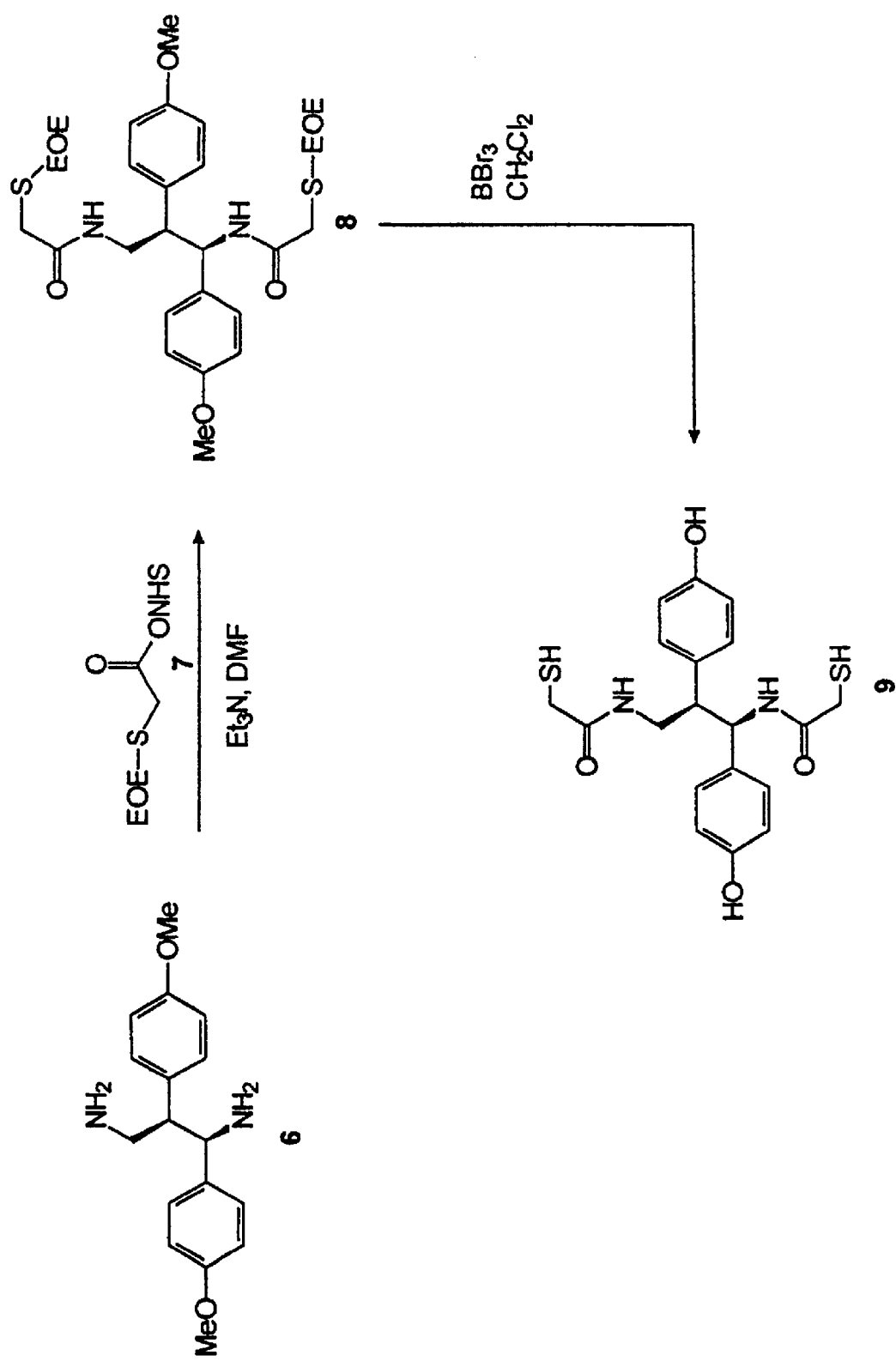
FIG. 1B illustrates a series of chemical reactions more fully described in Example 1, that may be used to convert the precursor of FIG. 1A into a steroid receptor analog of the invention having amide and thiol metal binding groups.

$N_2S_2$ chelating agent 9 is prepared according to the scheme shown in FIG. 1B, and the following description, which refers to compounds by their identifying numbers as set forth in FIG. 1B.

To a solution of diamine 6 (1.0 mmol) in anhydrous DMF (4 mL) containing triethylamine (6.0 mmol) is added N-hydroxysuccinimidyl S-(1-ethoxyethyl)mercaptoacetate 7 (Kasina, S. et al., *J. Nucl. Med.* 32(7):1445–1451, 1991) dissolved in anhydrous DMF (2 mL). The mixture is stirred for 2 hours, then filtered, and the filtrate concentrated in vacuo. The resulting oil is dissolved in ethyl acetate, washed with water and brine, then dried (sodium sulfate) and concentrated. The oil is chromatographed ($SiO_2$, ethyl acetate/hexanes) to give diamide 8.

Diamide 8 (1.0 mmol) is dissolved in methylene chloride (3 mL). The reaction flask is purged with nitrogen and cooled in a dry ice/isopropanol bath. Boron tribromide (2.2 mmol) is then added via syringe and the cold bath removed. After stirring for 30 min, the mixture is poured onto ice water, stirred for 30 min, saturated with salt and extracted with 3:1 methylene chloride:isopropanol. The extract is dried (sodium sulfate) and concentrated and the resulting oil purified by chromatography ($SiO_2$, methanol/methylene chloride) to give $N_2S_2$ chelating agent 9.

Example 2

Synthesis of $N_2S_2$ Chelating Agent 11

Figure 2:
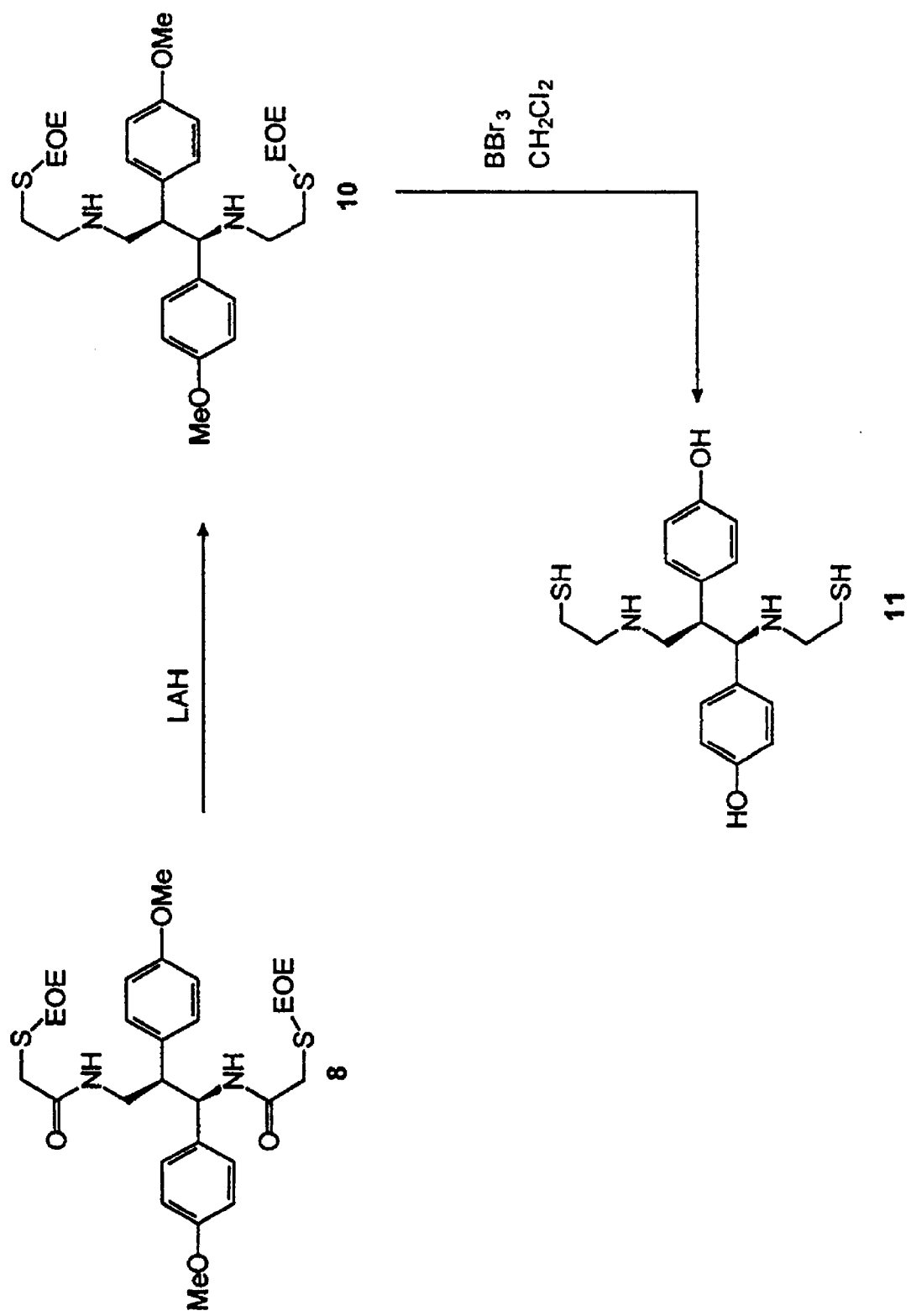
FIG. 2 illustrates a series of chemical reactions more fully described in Example 2 that may be used to convert the precursor of FIG. 1A into a steroid receptor analog of the invention having amine and thiol metal binding groups.

$N_2S_2$ chelating agent 11 is prepared from diamide 8 (prepared as described in Example 1) as shown in the scheme of FIG. 2 and the following description, which refers to compounds by their identifying numbers as set forth in FIG. 2.

To a solution of LAH (1.0 mmol) in THF (1 mL) is added, dropwise via syringe, a solution of diamide 8 (0.5 mmol) in THF (1 mL). The mixture is heated to reflux for 16 hours, then cooled to room temperature, and water cautiously added so as to produce a granular precipitate of lithium aluminate. The mixture is filtered and concentrated, and the resulting oil purified by chromatography ($SiO_2$, triethylamine/ethyl acetate/hexane) to give diamine 10.

Diamine 10 (0.5 mmol) is dissolved in methylene chloride (2 mL). The reaction flask is purged with nitrogen and cooled in a dry ice/isopropanol bath. Boron tribromide (1.1 mmol) is then added via syringe and the cold bath removed. After stirring for 30 min the mixture is poured onto ice water, stirred for 30 min, saturated with salt and extracted with 3:1 methylene chloride: isopropanol. The extract is dried (sodium sulfate) and concentrated and the resulting oil purified by chromatography ($SiO_2$, methanol/methylene chloride) to give $N_2S_2$ chelating agent 11.

Example 3

Synthesis of Bis (DOTA) Chelating Agent 19

Synthesis of Acid 17

Figure 3A:
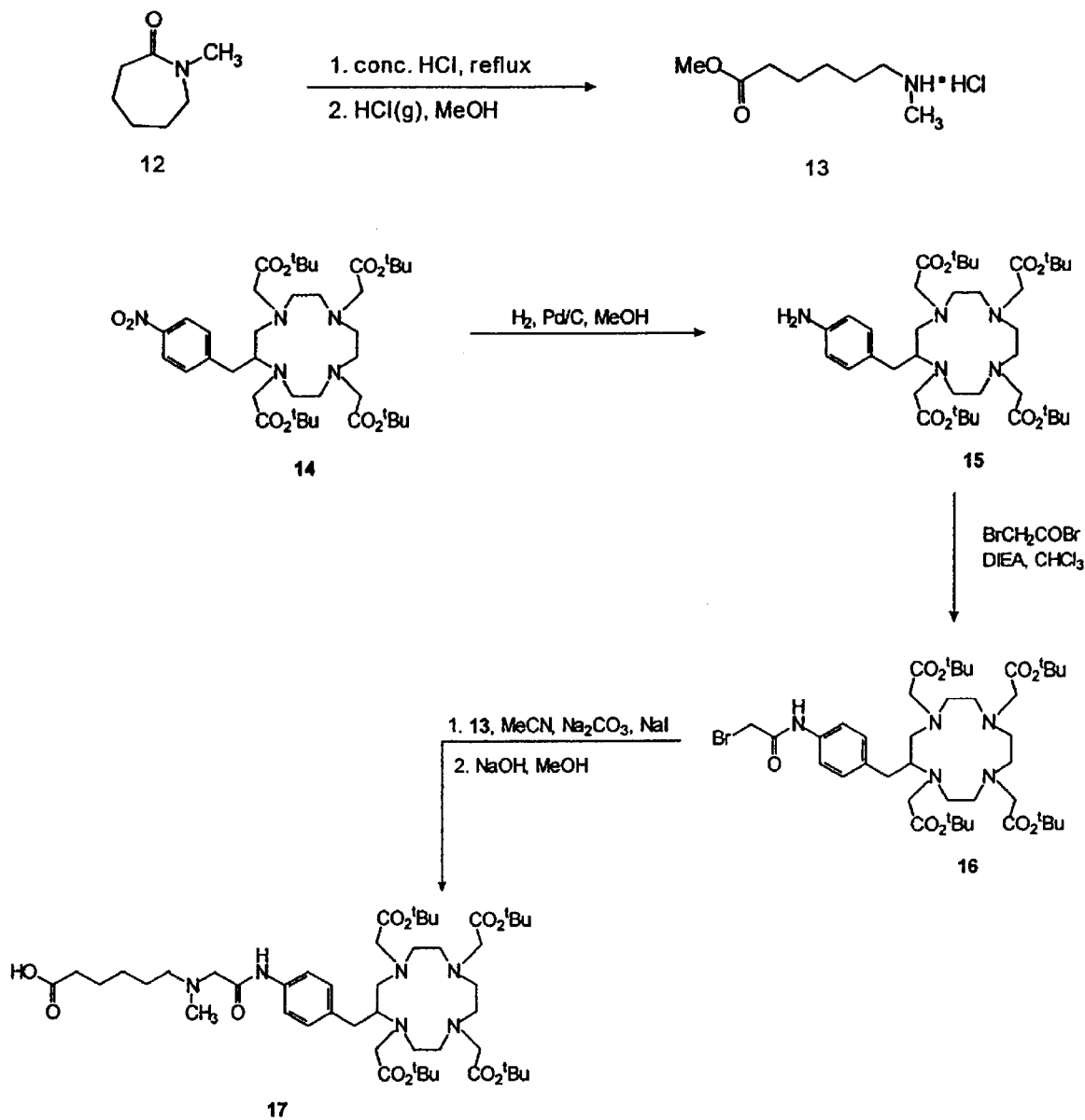
FIG. 3A illustrates a series of chemical reactions more fully described in Example 3 that may be used to convert N-methyl caprolactam to an $N_4$ metal binding arm that may be used to form a steroid receptor analog of the invention.

Acid 17 is prepared according to the scheme shown in FIG. 3A, and the following description, which refers to compounds by their identifying numbers as set forth in FIG. 3A.

A solution of N-methyl caprolactam 12 (158 mmol) in conc. HCl (250 mL) is heated to reflux for 5 days. The reaction mixture is cooled to room temperature and concentrated to give a brown oil.

The crude oil is dissolved in MeOH (300 mL) and HCl gas is bubbled through the solution for 4 min (the total HCl uptake is approx. 24 g). The mixture is allowed to stir at room temperature overnight then concentrated. 20% methylene chloride/diethyl ether (150 mL) is added and the solids are scraped from the walls of the flask with a spatula. The mixture is stirred for 30 min, then filtered, and the filter cake washed with 10% methylene chloride/diethyl ether (2×50 mL). Drying (high vac.) to constant weight yields methyl 6-methylaminohexanoate hydrochloride 13 as a white solid in high purity.

p-Nitrobenzyl-DOTA t-butyl ester 14 (1 mmol, prepared as described in Garrity M. L. et al., *Tetrahedron Lett.* 34(35):5531–4, 1993) is dissolved in MeOH (10 mL) and 10% Pd/C (20 mg) is added under nitrogen. The reaction vessel is purged with nitrogen then filled with hydrogen. The mixture is stirred at atmospheric pressure overnight. The catalyst is removed by filtration through glass microfiber paper (Whatman). Concentration gives p-aminobenzyl-DOTA t-butyl ester 15.

p-Aminobenzyl-DOTA t-butyl ester 15 (0.8 mmol) is dissolved in $CHCl_3$ (6 mL) and bromoacetyl bromide (1.0 mmol) is added followed by N,N-diisopropylethylamine (5 mmol). The progress of the reaction is monitored by TLC. When all starting material is consumed the reaction mixture is concentrated and the crude mixture purified by silica gel chromatography (methanol/methylene chloride) to give p-bromoacetamidobenzyl-DOTA t-butyl ester 16.

To a solution of bromoacetamidobenzyl-DOTA t-butyl ester 16 (0.5 mmol) in acetonitrile (5 mL) is added amine 13 (0.55 mmol) followed by sodium carbonate (3 mmol) and several small crystals of sodium iodide (approx. 3 mg). The mixture is heated to reflux for 6 hours then cooled to room temperature and filtered to remove insolubles. The solids are rinsed with additional acetonitrile (5 mL) and the combined organic solution is concentrated in vacuo. Water (10 mL) is added and the solution extracted with methylene chloride (3×5 mL). The combined organic extracts are dried (magnesium sulfate) and concentrated.

The resulting oil is dissolved in MeOH (10 mL) and 1N aqueous NaOH (10 mL) is added. The solution is stirred at room temperature for 12 hours then concentrated and the residue redissolved in water (10 mL), The aqueous solution is washed with ether (2×5 mL) then acidified by the addition of 1N aqueous HCl (approx. 10 mL) and extracted with ethyl acetate (3×10 mL). The combined organic extracts are dried (sodium sulfate) and concentrated. The resulting oil is purified by chromatography ($SiO_2$, methanol/methylene chloride) to give acid 17.

Synthesis of bis(DOTA) Chelating Agent 19

Figure 3B:
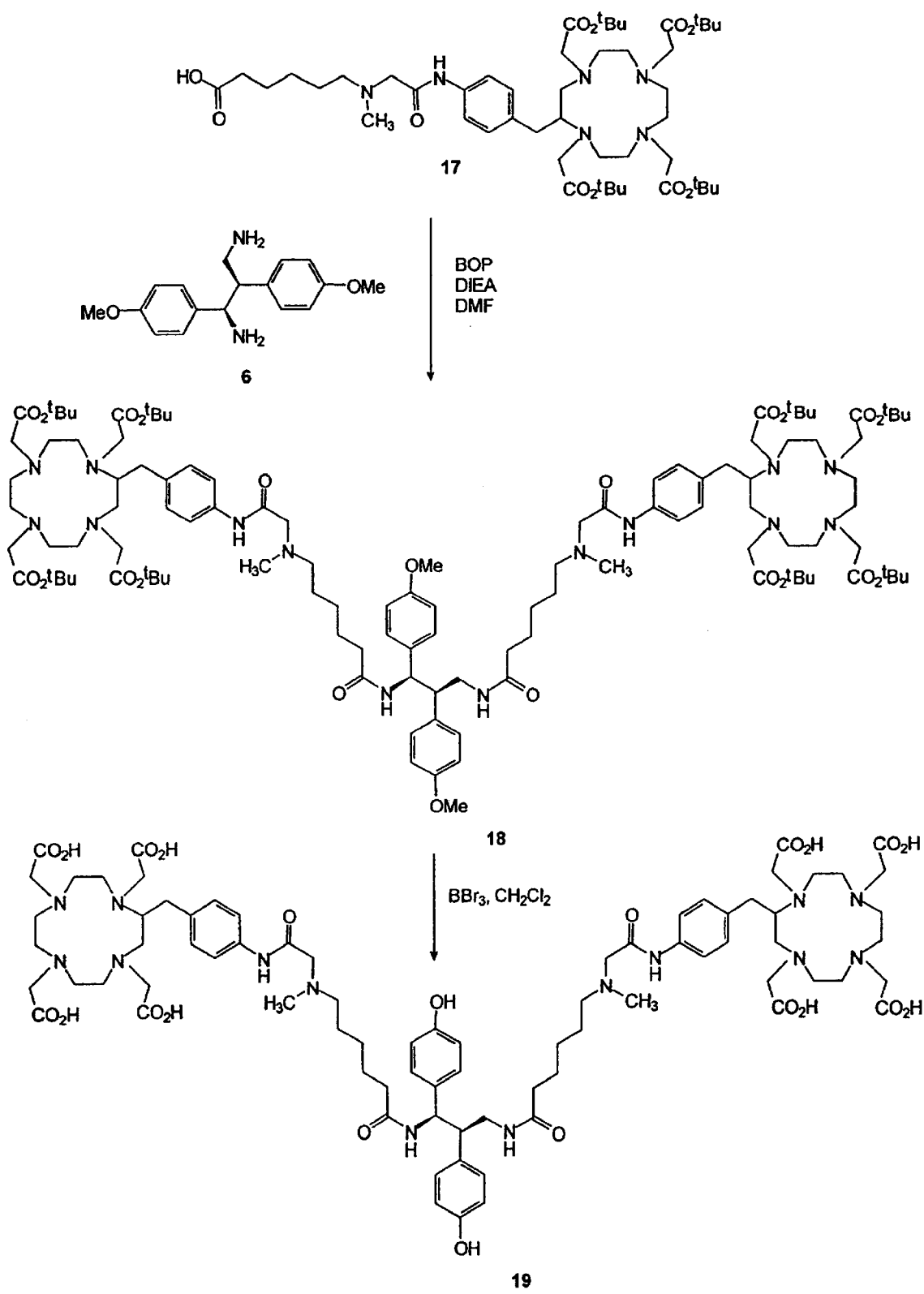
FIG. 3B illustrates a series of chemical reactions more fully described in Example 3 that may be used to join the metal binding arms illustrated in FIG. 3A to the precursor of FIG. 1A so as to provide a steroid receptor analog of the invention having two $N_4$ binding arms.

Chelating agent 19 is prepared according to the scheme shown in FIG. 3B, and the following description, which refers to compounds by their identifying numbers as set forth in FIG. 3B.

To a solution of acid 17 (1.1 mmol) in DMF (8 mL) is added BOP (1.1 mmol) followed by DIEA (1 mL) and a solution of diamine 6 (0.5 mmol, prepared as in Example 1) in DMF (3 mL). The mixture is allowed to stir at room temperature for 12 hours then concentrated. The residue is dissolved in ethyl acetate (30 mL) and washed with 1N aqueous HCl (2×15 mL), water (15 mL) and saturated aqueous sodium bicarbonate solution (2×15 mL). The organic solution is then dried and concentrated and the resulting oil chromatographed ($SiO_2$, methanol/methylene chloride) to give bis(DOTA) compound 18.

Bis(DOTA) compound 18 (0.3 mmol) is dissolved in methylene chloride (2 mL). The reaction flask is purged with nitrogen and cooled in a dry ice/isopropanol bath. Boron tribromide (0.7 mmol) is then added via syringe and the cold bath removed. After stirring for 30 min the mixture is poured onto ice water, stirred for 30 min, saturated with salt and extracted with 3:1 methylene chloride:isopropanol. The extract is dried (sodium sulfate) and concentrated and the resulting oil purified by chromatography ($SiO_2$, methanol/methylene chloride) to give bis(DOTA) chelating agent 19.

Example 4

Synthesis of Bis($N_2S_2$) Chelating Agent 22

Figure 4:
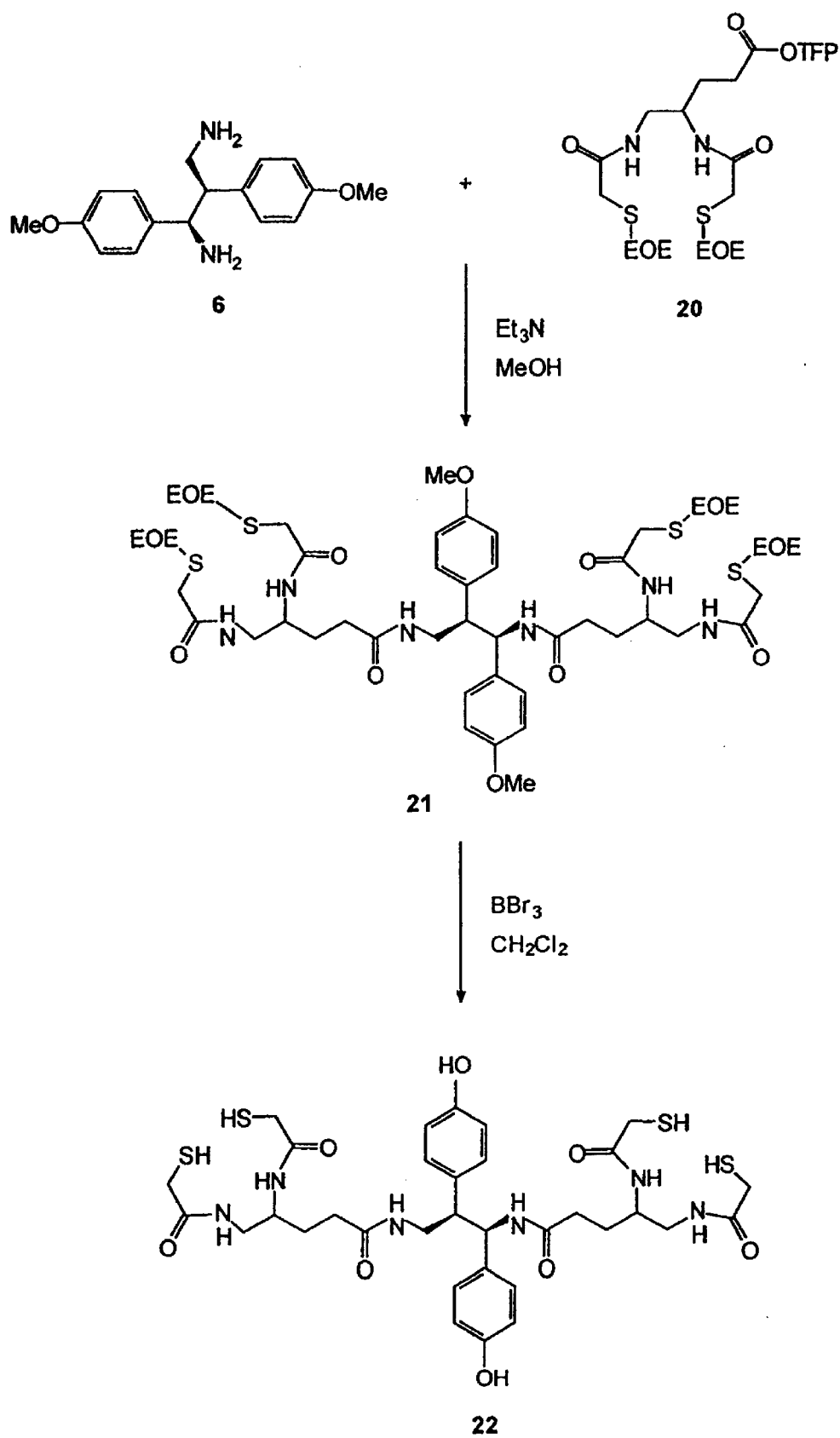
FIG. 4 illustrates a series of chemical reactions more fully described in Example 4 that may be used to prepare a steroid analog receptor of the invention having two $N_2S_2$ binding arms, where the N atoms are part of amide groups.

Bis $N_2S_2$ chelating agent 22 is prepared according to the scheme shown in FIG. 4, and the following description, which refers to compounds by their identifying numbers as set forth in FIG. 4.

To a solution of diamine 6 (1.0 mmol, prepared as in Example 1) and 2,3,5,6-tetrafluorophenyl 4,5-bis(S-1-ethoxyethyl mercaptoacetamido)pentanoate 20 (2.2 mmol, Kasina, S.; et al *J. Nucl. Med.* 32(7):1445–1451 1991) in MeOH (10 mL) is added triethylamine (1.0 mL). The mixture is stirred for one hr then concentrated in vacuo and the resulting oil chromatographed ($SiO_2$, ethyl acetate/hexane) to give hexaamide 21.

Hexaamide 21 (0.6 mmol) is dissolved in methylene chloride (5 mL). The mixture is purged with nitrogen and cooled in a dry ice/isopropanol bath. Boron tribromide (1.4 mmol) is then added via syringe and the cold bath removed. After stirring for 30 min the mixture is poured onto ice water, stirred for 30 min, saturated with salt and extracted with 3:1 methylene chloride:isopropanol. The extract is dried (sodium sulfate) and concentrated. The resulting oil is purified by chromatography ($SiO_2$, methanol/methylene chloride) to give bis ($N_2S_2$) chelating agent 22.

Example 5

Synthesis of Bis($N_2S_2$) Chelating Agent 24

Figure 5:
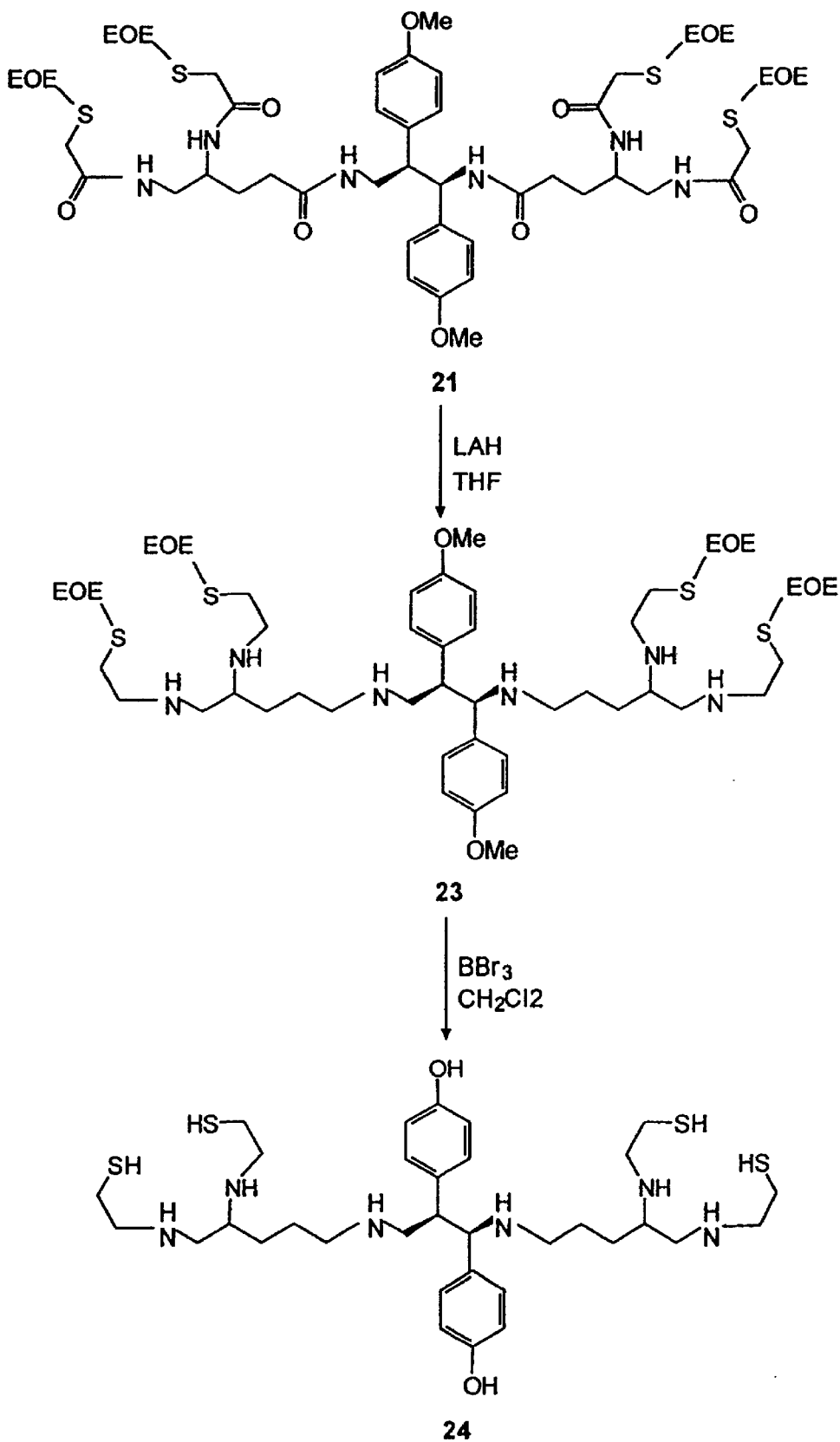
FIG. 5 illustrates a series of chemical reactions more fully described in Example 5 that may be used to convert an intermediate shown in FIG. 4 into a steroid analog receptor of the invention having two $N_2S_2$ binding arms, where the N atoms are part of amine groups.

Bis $N_2S_2$ chelating agent 24 is prepared according to the scheme shown in FIG. 5, and the following description, which refers to compounds by their identifying numbers as set forth in FIG. 5.

To a solution of LAH (3.0 mmol) in THF (3 mL) is added, dropwise via syringe, a solution of hexaamide 21 (0.5 mmol, prepared as in Example 4) in THF (1 mL). The mixture is heated to reflux for 16 hrs then cooled to room temperature and water cautiously added so as to produce a granular precipitate of lithium aluminate. The mixture is filtered and concentrated and the resulting oil purified by chromatography ($SiO_2$, triethylamine/methanol/methylene chloride) to give hexaamine 23.

Hexaamine 23 (0.4 mmol) is dissolved in methylene chloride (4 mL). The mixture is purged with nitrogen and cooled in a dry ice/isopropanol bath. Boron tribromide (1.0 mmol) is then added via syringe and the cold bath removed. After stirring for 30 min the mixture is poured onto ice water, stirred for 30 min, saturated with salt and extracted with 3:1 methylene chloride:isopropanol. The extract is dried (sodium sulfate) and concentrated and the resulting oil purified by chromatography ($SiO_2$, methanol/methylene chloride) to give bis($N_2S_2$) chelating agent 24.

Example 6

Synthesis of $N_2S_2$ Chelating Agent 33

Figure 6:
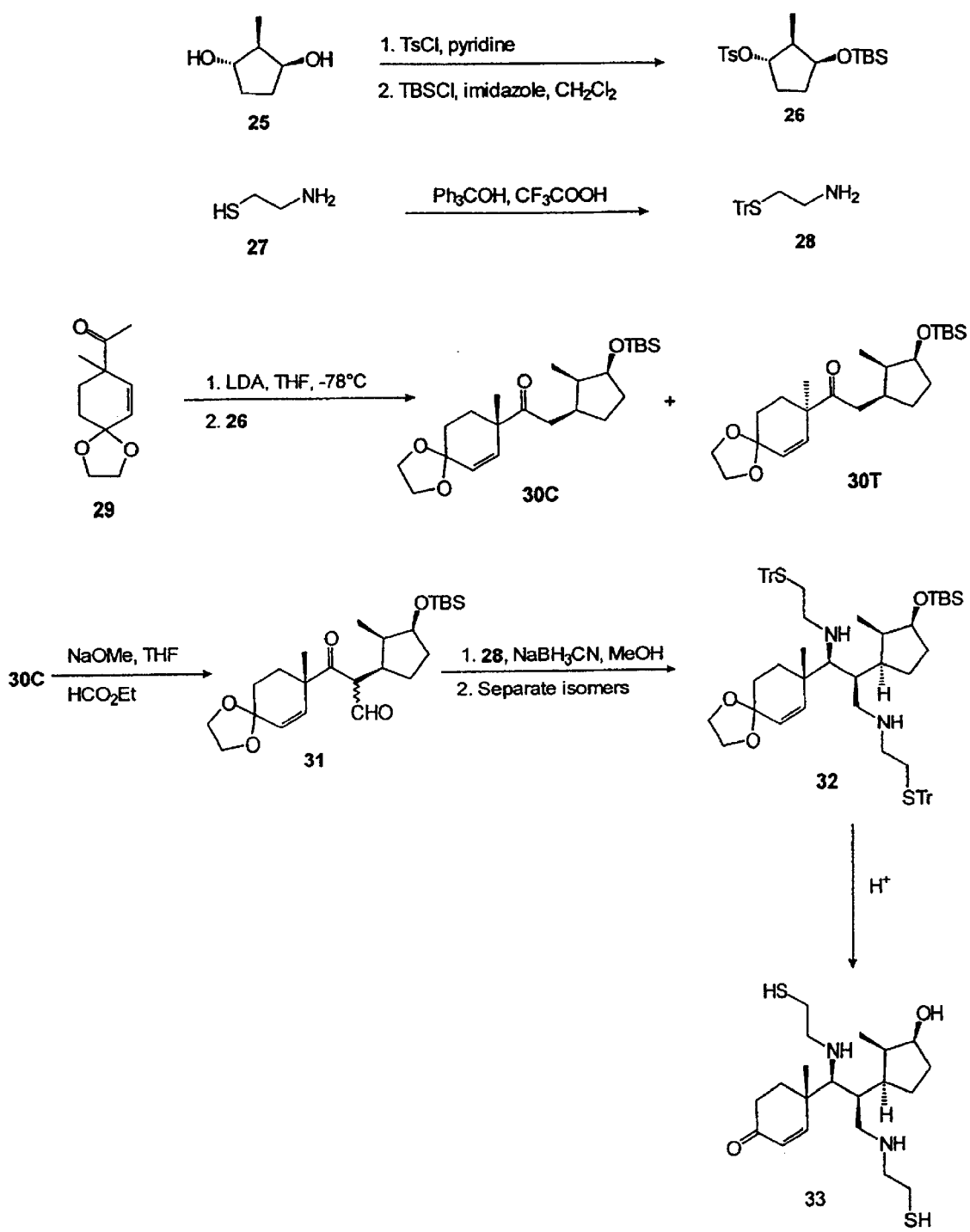
FIG. 6 illustrates a series of chemical reactions more fully described in Example 6 that may be employed to prepare an $N_2S_2$ steroid receptor analog of the invention having affinity to androgen receptors.

$N_2S_2$ chelating agent 33 is prepared according to the scheme shown in FIG. 6, and the following description, which refers to compounds by their identifying numbers as set forth in FIG. 6.

To an ice cooled solution of TsCl (2.0 mmol) in anhydrous pyridine (10 mL) is added a solution of 2-methyl-1,3-pentane diol 25 (2.0 mmol, prepared according to D'Haenens, L. et al *Bull. Soc. Chim. Belg.* 95(4):273–81 1986) in anhydrous pyridine (10 mL). After 30 min the solution is poured into 200 mL water and extracted with ethyl acetate (2×100 mL). The combined organic extracts are washed with water and saturated sodium chloride solution then dried (magnesium sulfate) and concentrated. This material is dissolved in DMF (4 mL) and added, via syringe, to an ice cooled, stirred solution of TBDMSCl (2.5 mmol), DMAP (approx. 3 mg) and imidazole (2.5 mmol) in DMF (4 mL). The mixture is allowed to slowly warm to room temperature After 12 hrs the mixture is poured into water (50 mL) and extracted with hexanes (4×30 mL). The combined organic extracts are dried (magnesium sulfate), concentrated in vacuo, and then chromatographed ($SiO_2$, ethyl acetate/hexane) to give tosylate 26.

Triphenylmethanol (44 mmol) is added to a stirred solution of 2-aminoethanethiol hydrochloride (44 mmol) in trifluoroacetic acid (40 mL). After stirring for 30 min the solution is concentrated in vacuo and triturated with diethyl ether (200 mL) to give amine 28 as a white solid in a high state of purity.

A solution of ketone 29 (2.0 mmol, prepared according to Waring, A. J. et al *J. Chem. Soc. Perkin Trans I*, (3):631–9 1985) in anhydrous THF (5 mL+1 mL rinse) is added, dropwise, via syringe, to a solution of LDA (2.2 mmol) in THF (5 mL) under nitrogen at −78° C. After stirring for 30 min a solution of tosylate 26 (2.0 mmol) in THF (3 mL) is added dropwise via syringe. The solution is allowed to gradually warm to room temperature and stirred for 12 hours, then cooled in ice and quenched with saturated aqueous ammonium chloride (2 mL). The mixture is poured into water then extracted with ethyl acetate. The combined organic extracts are washed with saturated aqueous sodium bicarbonate solution, dried (magnesium sulfate) and concentrated in vacuo. The resulting crude oil is then chromatographed to give the desired cis isomer 30C.

A solution of ketone 30C (1.0 mmol) is dissolved in anhydrous THF (2 mL) and this solution is added dropwise to an ice cooled solution of sodium methoxide (1.1 mmol) in THF (3 mmol). Ethyl formate (2.0 mmol) is then added and the ice bath allowed to slowly melt. After stirring for 12 hours the reaction mixture is quenched with saturated aqueous ammonium chloride solution (2 mL). Water is added (10 mL) and the mixture extracted with ethyl acetate (3×8 mL). The combined organic extracts are washed with saturated aqueous sodium bicarbonate solution then dried and concentrated to give ketoaldehyde 31 as a mixture of isomers.

To a solution of ketoaldehyde 31 (0.5 mmol) and amine 28 (0.5 mmol) in anhydrous MeOH (5 mL) is added sodium cyanoborohydride (1.0 mmol). The resulting solution is stirred under nitrogen at room temperature for 16 hours then concentrated. Ethyl acetate (10 mL) and 40% aqueous potassium carbonate (15 mL) are added. The aqueous phase is further extracted with ethyl acetate (2×7 mL) and the combined organics dried (sodium sulfite) and concentrated in vacuo. The desired isomer 32 is isolated by preparative HPLC (Dynamax 60A, C-18 reversed phase column, Rainin Instrument Co. Inc.).

A solution of 32 (0.5 mmol) in glacial acetic acid (12 mL) is treated with 1N aqueous HCl solution (4 mL). The solution is heated to reflux for 1 hr then cooled to room temperature and concentrated. The crude material is chromatographed ($SiO_2$, MeOH/methylene chloride) to give the desired $N_2S_2$ chelating agent 33.

Example 7

Synthesis of Bis(DOTA) Chelating Agent 35

Figure 7:
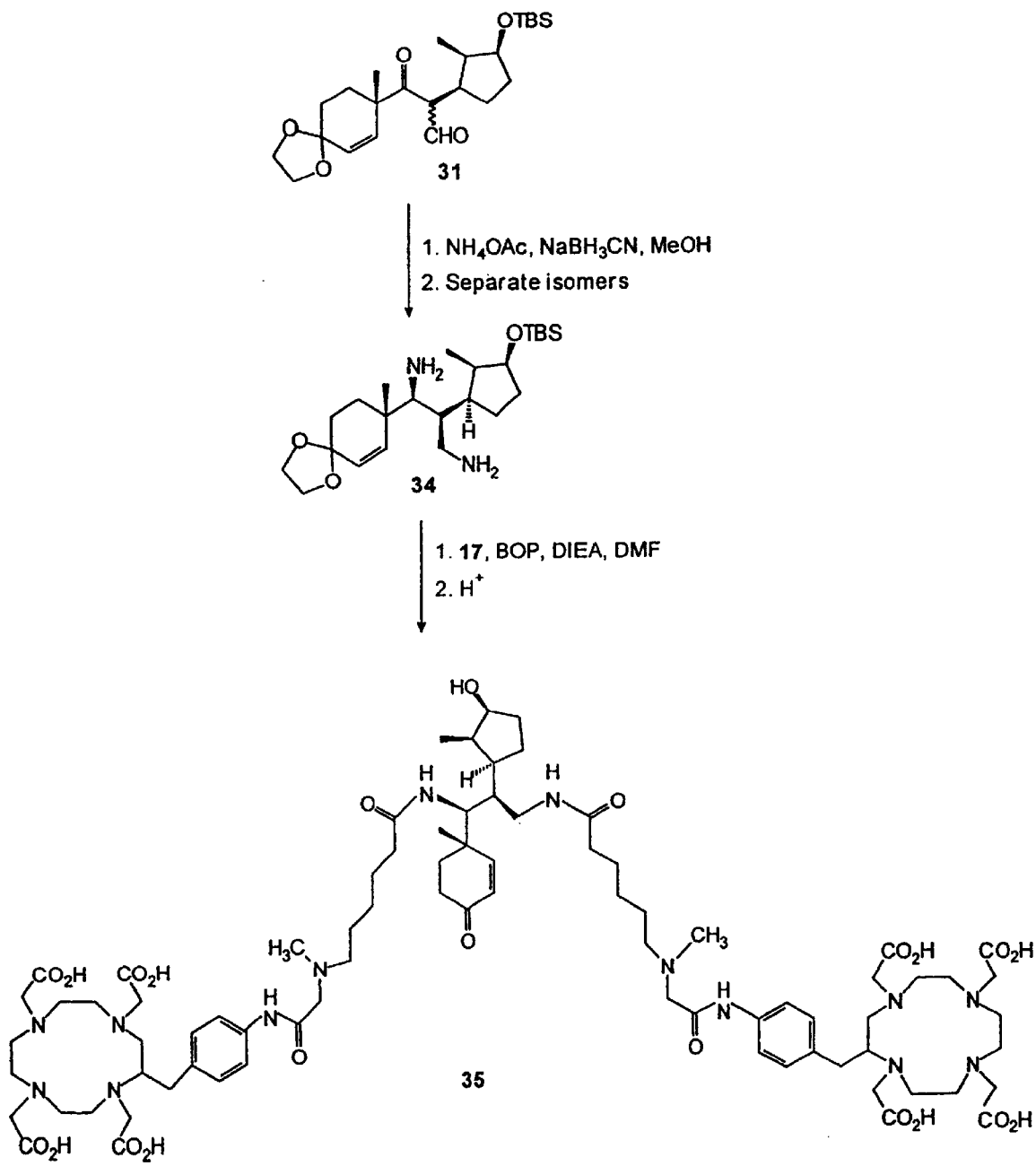
FIG. 7 illustrates a series of chemical reactions more fully described in Example 7 that may be employed to prepare an androgen receptor analog of the invention having two $N_4$ binding arms.

Bis(DOTA) chelating agent 35 is prepared according to the scheme shown in FIG. 7, and the following description, which refers to compounds by their identifying numbers as set forth in FIG. 7.

To a solution of ketoaldehyde 31 (0.5 mmol, prepared as in Example 6) and ammonium acetate (7.5 mmol) in anhydrous MeOH (5 mL) is added sodium cyanoborohydride (1.0 mmol). The resulting suspension is stirred under nitrogen at room temperature for 16 hrs, then filtered and concentrated. Ethyl acetate (10 mL) and 40% aqueous potassium carbonate (15 mL) are added. The aqueous phase is further extracted with ethyl acetate (2×7 mL) and the combined organic extracts are dried (sodium sulfate) and concentrated in vacuo. The desired isomer 34 is isolated by preparative HPLC (Dynamax 60A, C-18 reversed phase column, Rainin Instrument Co. Inc.).

To a solution of acid 17 (1.1 mmol, prepared as in Example 3) in DMF (8 mL) is added BOP (1.1 mmol) followed by DIEA (1 mL) and a solution of diamine 34 (0.5 mmol) in DMF (3 mL). The mixture is allowed to stir at room temperature for 12 hours then concentrated. The residue is dissolved in ethyl acetate (30 mL) and washed with water (15 mL) and saturated aqueous sodium bicarbonate solution (2×15 mL). The organic solution is then dried and concentrated.

The resulting oil is dissolved in glacial acetic acid (12 mL) and the solution then cooled in ice. 1N aqueous HCl solution (4 mL) is added gradually and the solution is allowed to slowly warm to room temperature. After 2 hrs the mixture is concentrated and the resulting oil is chromatographed ($SiO_2$, MeOH/methylene chloride) to give bis (DOTA) chelating agent 35.

Example 8

Synthesis of Bis($N_2S_2$) Chelating Agent 37

Figure 8:
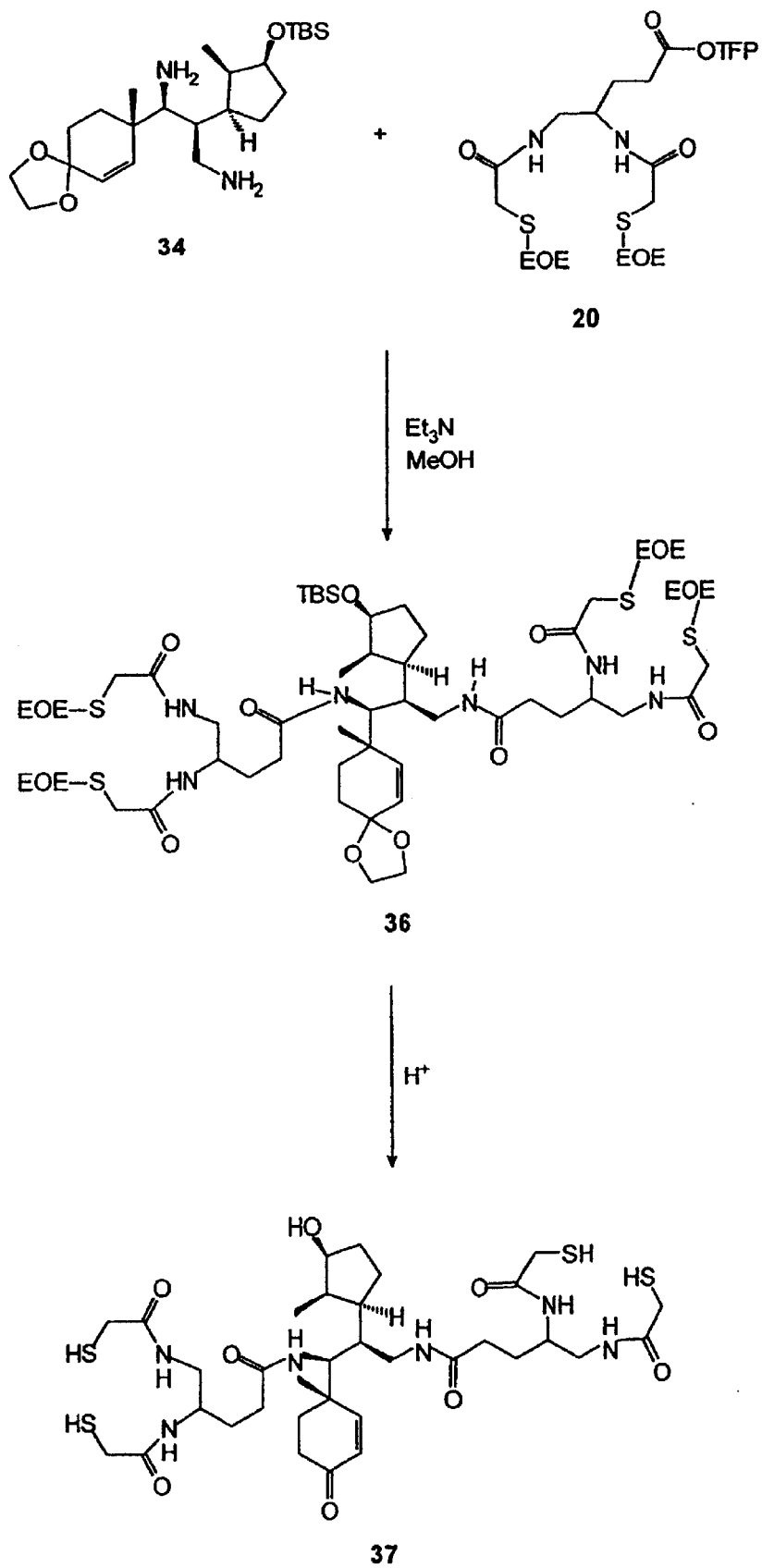
FIG. 8 illustrates a series of chemical reactions more fully described in Example 8 that may be employed to prepare an androgen receptor analog of the invention having two $N_2S_2$ binding arms, where the N atoms are part of amide groups.

Bis $N_2S_2$ chelating agent 37 is prepared according to the scheme shown in FIG. 8, and the following description, which refers to compounds by their identifying numbers as set forth in FIG. 8.

To a solution of diamine 34 (1.0 mmol, prepared as in Example 7) and 2,3,5,6-tetrafluorophenyl 4,5-bis(S-1-ethoxyethyl mercaptoacetamido)pentanoate 20 (2.2 mmol, Kasina, S. et al *J. NucL Med.* 32(7):1445–1451 1991) in MeOH (10 mL) is added triethylamine (1.0 mL). The mixture is stirred for one hr then concentrated in vacuo and the resulting oil chromatographed ($SiO_2$, ethyl acetate/hexane) to give hexaamide 36.

Hexaamide 36 is dissolved in glacial acetic acid (12 mL) and the solution then cooled in ice. 1N aqueous HCl solution (4 mL) is added gradually and the solution is allowed to slowly warm to room temperature. After 2 hours the mixture is concentrated and the resulting oil is chromatographed ($SiO_2$, MeOH/methylene chloride) to give bis($N_2S_2$) chelating agent 37.

Example 9

Synthesis of Bis($N_2S_2$) Chelating Agent 38

Figure 9:
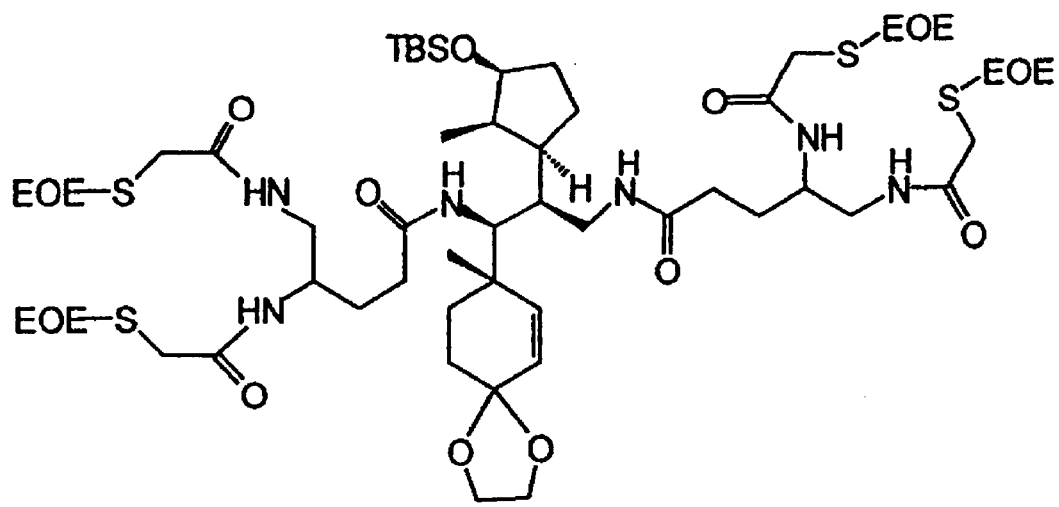
FIG. 9 illustrates a series of chemical reactions more fully described in Example 9 that may be employed to prepare an androgen receptor analog of the invention having two $N_2S_2$ binding arms, where the N atoms are part of amine groups.
Figure 9:
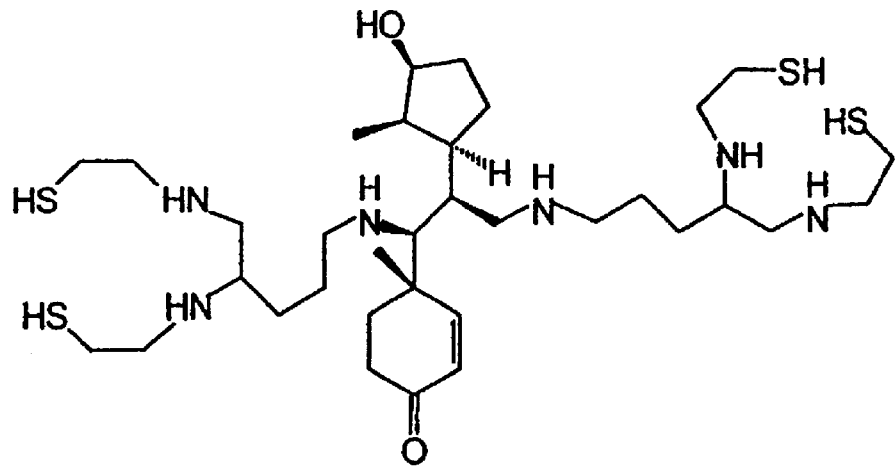

Bis $N_2S_2$ chelating agent 39 is prepared according to the scheme shown in FIG. 9, and the following description, which refers to compounds by their identifying numbers as set forth in FIG. 9.

To a solution of LAH (3.0 mmol) in THF (3 mL) is added, dropwise via syringe, a solution of hexaamide 36 (0.5 mmol, prepared as in Example 8) in THF (1 mL). The mixture is heated to reflux for 16 hrs then cooled to room temperature and water cautiously added so as to produce a granular precipitate of lithium aluminate. The mixture is filtered and concentrated. The resulting oil is dissolved in glacial acetic acid (12 mL) and the solution then cooled in ice. 1N aqueous HCl solution (4 mL) is added gradually and the solution is allowed to slowly warm to room temperature. After 2 hrs the mixture is concentrated and the resulting oil is chromatographed ($SiO_2$, MeOH/methylene chloride) to give bis ($N_2S_2$) chelating agent 38.

Example 10

Preparation of $^{99m}$Tc-8

Preparation of Lyophilized Compound 8

The $N_2S_2$ compound 8 (see Example 1) prelyophilized reagent is formulated as a 1 mL aqueous solution containing 0.1–1.0 mg of compound 8, 2.5–5.0 mg of sodium gluconate, 0.1 mg of stannous chloride, 0.1 mg of gentisic acid, 40 mg of lactose filler, and 25%–50% v/v tert-butyl alcohol. During preparation, compound 8 is dissolved in an $H_2O$/tert-butyl alcohol solution and added to an aqueous concentrate (1.5×) of the remaining ingredients adjusted to pH 1.8 with sulfuric acid. The solution is vialed in grade A borosilicate 10 mL vials fitted with 25 mm diameter gray butyl rubber lyophilization stoppers and frozen at −40° C. within 30 minutes of preparation. Lyophilization proceeded at 50–100 m torr vacuum with maintenance of product below a collapse temperature of −25° C. for 23 hr for primary drying. Secondary drying proceeded upon 0.3° C./min ramping in like manner to 25° C. and holding for 20 hr. Afterwards, the vials are backfilled with nitrogen or argon to 6 in of Hg and stoppered. Final moisture content is ≦0.4% as assessed by Karl Fischer assay.

Preparation of $^{99m}$TC-8

To prepare $^{99m}$Tc-8, 1.0 mL of [$^{99m}$Tc] sodium pertechnetate in saline (50 mCi) is added to the lyophilized compound 8 reagent. The vial is shaken to dissolve the contents and then vented to the air using 0.2 μm sterile filter. Following addition of 0.25–0.5 mL of 2-propanol, the reaction vial is mixed and incubated at 25° C.–100° C. for 10–30 min, and then cooled on ice.

Figure 10:
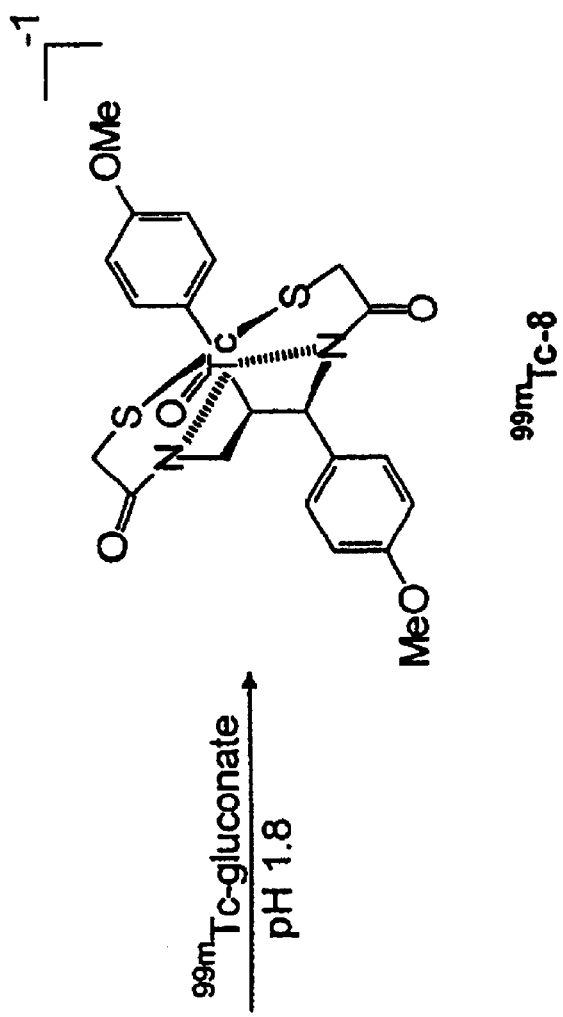
FIG. 10 illustrates the chemistry more fully described in Example 10 which may be used to form an estrogen receptor diagnostic agent of the invention from $^{99m}Tc$ and an estrogen receptor analog of the invention having four donor atoms forming an $N_2S_2$ binding core, where the N atoms are part of amide groups and the sulfur atoms are in protected form.
Figure 10:
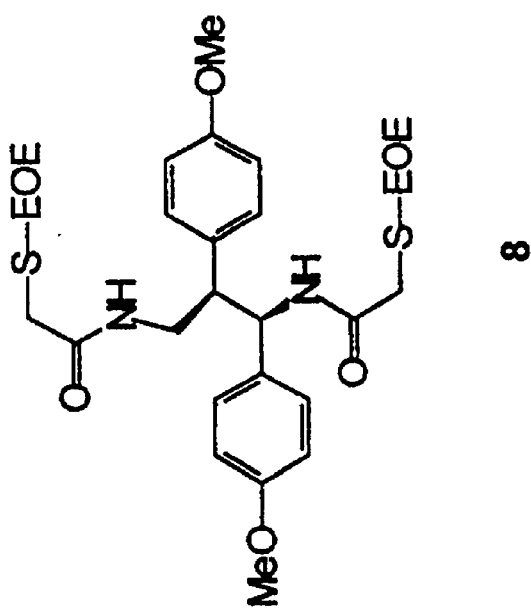

The chemistry of Example 10 is outlined in FIG. 10.

Example 11

Preparation of $^{99m}$TC-9

Preparation of Lyophilized Compound 9

The $N_2S_2$ ligand compound 9 (see Example 1) prelyophilized reagent is formulated as a 1 mL aqueous solution containing 0.1–1.0 mg of compound 9, 2.5–5.0 mg of sodium gluconate, 0.1 mg of stannous chloride, 0.1 mg of gentisic acid, 40 mg of lactose filler, and 25%–50% v/v tert-butyl alcohol. During preparation, compound 9 is dissolved in an $H_2O$/tert-butyl alcohol solution and added to an aqueous concentrate (1.5×) of the remaining ingredients adjusted to pH 6.0–6.5 with hydrochloric acid or sulfuric acid. The solution is vialed in grade A borosilicate 10 mL vials fitted with 5 mm diameter gray butyl rubber lyophilization stoppers and frozen at −40° C. within 30 min of preparation. Lyophilization proceeded at 50–100 m torr vacuum with maintenance of product below a collapse temperature of −25° C. for 24 h for primary drying. Secondary drying proceeded upon 0.3° C./min ramping to −12° C., holding for 16 h, followed by ramping in like manner to 25° C. and holding for 20 h. Afterwards, the vials are backfilled with nitrogen or argon to 6 in of Hg and stoppered. Final moisture content is ≦0.4% as assessed by Karl Fischer assay.

Preparation of $^{99M}$Tc-9

To prepare $^{99m}$Tc-compound 9, 1.0 mL of [$^{99m}$Tc] pertechnetate in saline (100 mCi) is added to the lyophilized compound 9 reagent. The vial is shaken to dissolve contents and then vented to the air using a sterile 0.2 μm filter fitted with a needle. Following addition of 0.25–0.50 mL of 2-propanol, the reaction vial is mixed, incubated at 25° C.–100° C. for 10–30 min, and then cooled on ice.

Figure 11:
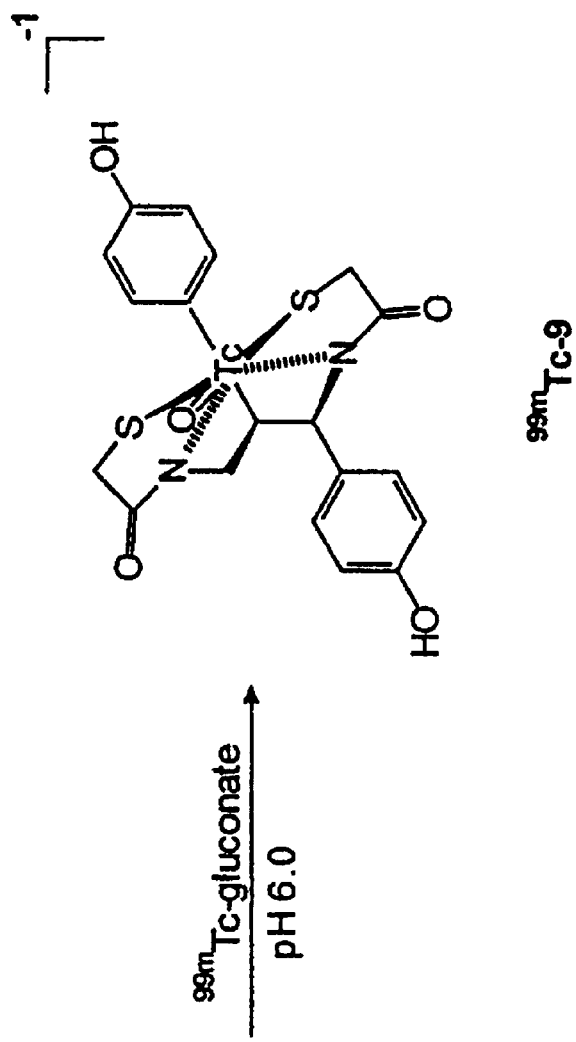
FIG. 11 illustrates the chemistry more fully described in Example 11 which may be used to form an estrogen receptor diagnostic agent of the invention from $^{99m}Tc$ and an estrogen receptor analog of the invention having four donor atoms forming an $N_2S_2$ binding core, where the N atoms are part of amide groups and the sulfur atoms are in the form of thiols.
Figure 11:
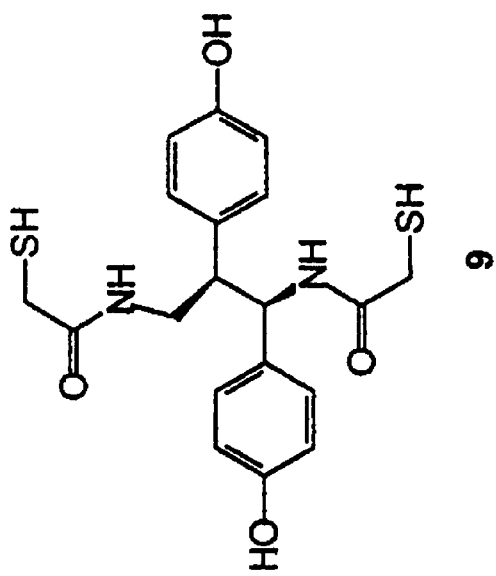

The chemistry of Example 11 is outlined in FIG. 11.

Example 12

Preparation of $^{99m}$TC-10

Preparation of Lyophilized Compound 10

$N_2S_2$-compound 10 (see Example 2) prelyophilized reagent is formulated as a 1 mL aqueous solution containing 0.1–1.0 mg of compound 10, 2.5–5.0 mg of sodium gluconate, 0.1 mg of stannous chloride, 0.1 mg of gentisic acid, 40 mg of lactose filler, and 25%–50% v/v tert-butyl alcohol. During preparation, compound 10 is dissolved in an $H_2O$/tert-butyl alcohol solution and added to an aqueous concentrate (1.5×) of the remaining ingredients adjusted to pH 5.0–7.5 with hydrochloric acid or sulfuric acid. The solution is vialed in grade A borosilicate 10 mL vials fitted with 25 mm diameter gray butyl rubber lyophilization stoppers and frozen at −40° C. within 30 minutes of preparation. Lyophilization proceeded at 50–100 m torr vacuum with maintenance of product below a collapse temperature of −25° C. for 24 h for primary drying. Secondary drying proceeded upon 0.3° C./min ramping to −12° C., holding for 16 h, followed by ramping in like manner to 25° C. and holding for 20 h. Afterwards, the vials are backfilled with nitrogen or argon to 6 in of Hg and stoppered. Final moisture content is ≦0.4% as assessed by Karl Fischer assay.

Preparation of $^{99M}$TC-10

To prepare $^{99m}$Tc-compound 10, 1.0 mL of $^{99m}$Tc-pertechnetate in saline (50 mCi) is added to the lyophilized compound 10 reagent. The vial is shaken to dissolve contents and then vented to the air using a sterile 0.2 μm filter fitted with a needle. Following addition of 0.25–0.5 mL of 2-propanol, the reaction vial is mixed, incubated at 25° C.–100° C. for 10–30 min, and then cooled on ice.

Figure 12:
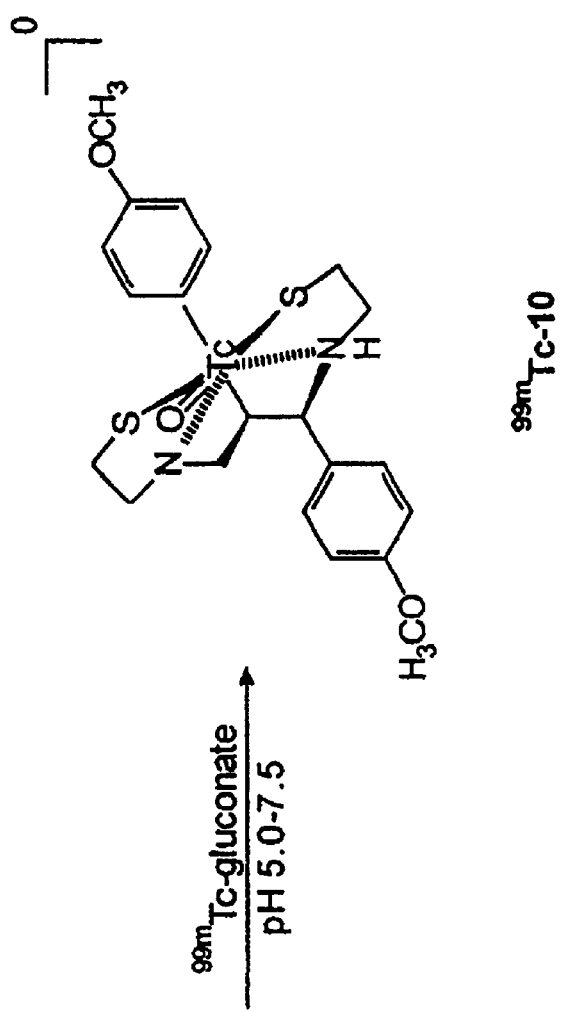
FIG. 12 illustrates the chemistry more fully described in Example 12 which may be used to form an estrogen receptor diagnostic agent of the invention from $^{99m}Tc$ and an estrogen receptor analog of the invention having four donor atoms forming an $N_2S_2$ binding core, where the N atoms are part of amine groups and the sulfur atoms are in protected form.
Figure 12:
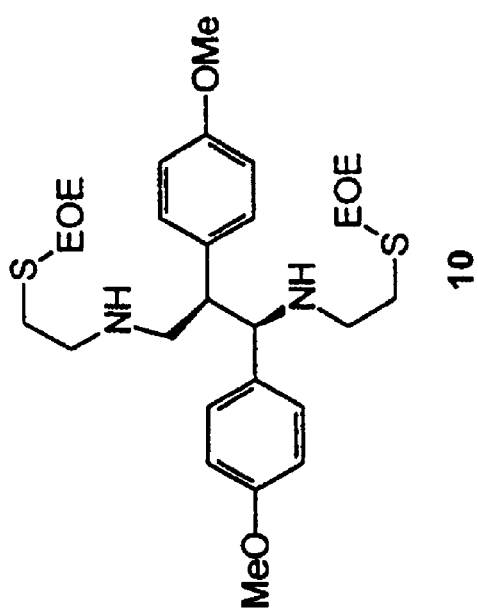

The chemistry of Example 12 is outlined in FIG. 12.

Example 13

Preparation of $^{99m}$TC-11

Preparation of Lyophilized Compound 11

Diamino disulfur ($N_2S_2$) compound 11 (see Example 2) prelyophilized reagent is formulated as a 1.0 mL aqueous solution containing 0.1–1.0 mg of compound 11, 2.5–5.0 mg of sodium gluconate, 0.1 mg of stannous chloride, 0.1 mg of gentisic acid, 40 mg of lactose filler, and 25%–50% v/v tert-butyl alcohol. During preparation, compound 11 is dissolved in an $H_2O$/tert-butyl alcohol solution and added to an aqueous concentrate (1.5×) of the remaining ingredients adjusted to pH 5.0–7.5 with hydrochloric acid or sulfuric acid. The solution is vialed in grade A borosilicate 10 mL vials fitted with 25 mm diameter gray butyl rubber lyophilization stoppers and frozen at −40° C. within 30 minutes of preparation. Lyophilization proceeded at 40–100 m torr vacuum with maintenance of product below a collapse temperature of −25° C. for 24 h for primary drying. Secondary drying proceeded upon 0.3° C./min ramping to −12° C., holding for 16 h, followed by ramping in like manner to 25° C. and holding for 20 h. Afterwards, the vials are backfilled with nitrogen or argon to 6 in of Hg and stoppered. Final moisture content is ≦0.4% as assessed by Karl Fischer assay.

Preparation of $^{99M}$TC-11

To prepare $^{99m}$Tc-compound 11, 1.0 mL of $^{99m}$Tc-pertechnetate in saline (50 mCi) is added to the lyophilized compound 11 reagent. The vial is shaken to dissolve contents and then vented to the air using a sterile 0.2 μm filter fitted with a needle. Following addition of 0.25–0.5 mL of 2-propanol, the reaction vial is mixed, incubated at 25° C.–100° C. for 10–30 min, and then cooled on ice.

Figure 13:
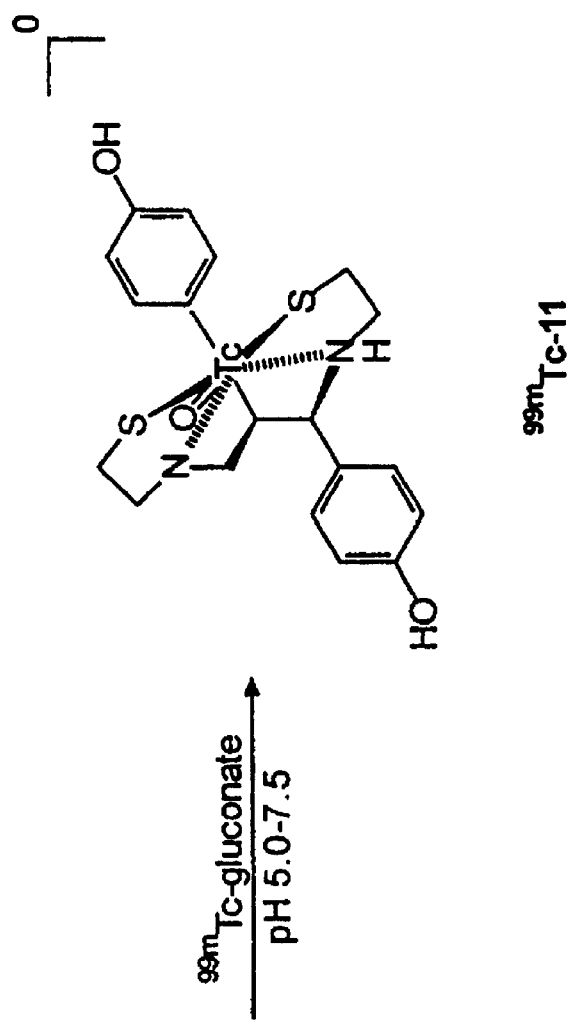
FIG. 13 illustrates the chemistry more fully described in Example 13 which may be used to form an estrogen receptor diagnostic agent of the invention from $^{99m}Tc$ and an estrogen receptor analog of the invention having two $N_1S_1$ binding arms, where the N atoms are part of amide groups and the sulfur atoms are in the form of thiols.
Figure 13:
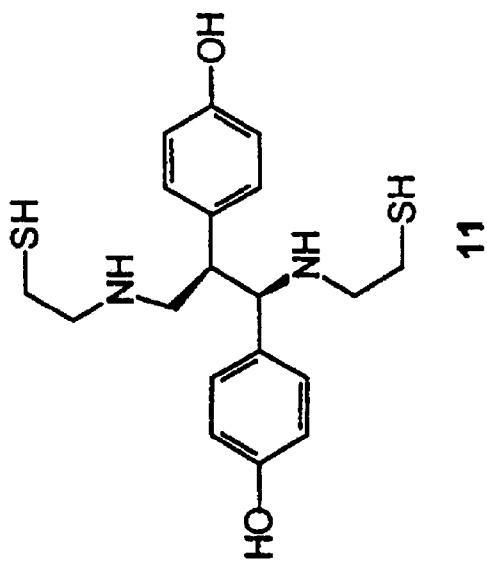

The chemistry of Example 13 is outlined in FIG. 13.

Example 14

Preparation of $^{90}$Y-19

To carrier-free 0.6 mCi Y-90 $Cl_3$ (10 μL, 50 mM HCl, NEN DuPont), 0.18 mg of compound 19 (see Example 3) in 450 μL of 2.0 M NH$_4$OAc, pH 5.0, is added and the reaction mixture is allowed to proceed for 30 minutes at 80° C. The percent of $^{90}$Y-radiolabeling, as monitored by a gradient HPLC system equipped with a radiometric detector, is greater than 99%.

Figure 14:
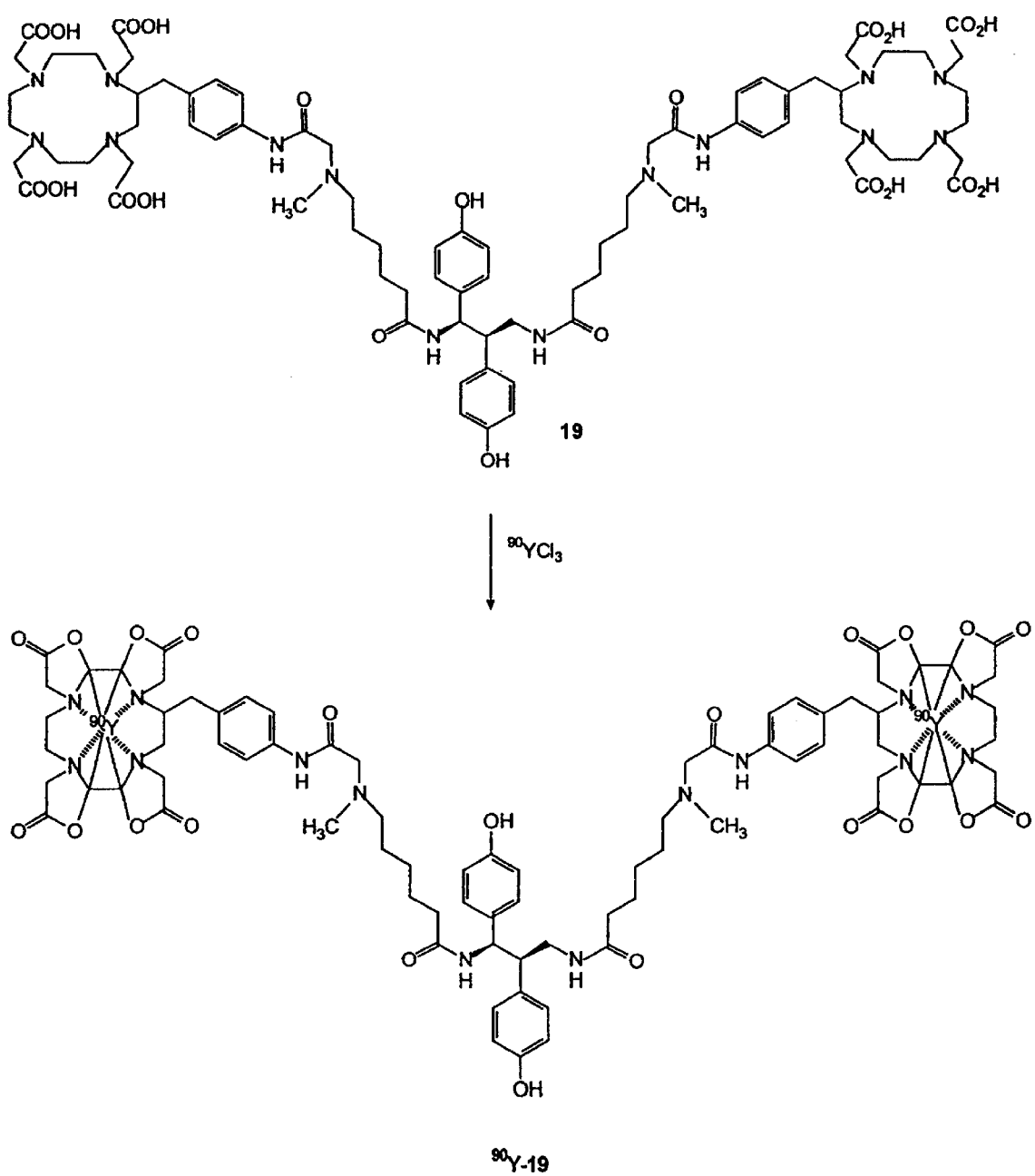
FIG. 14 illustrates the chemistry more fully described in Example 14 which may be used to form an estrogen receptor therapeutic agent of the invention from $^{90}Y$ and an estrogen receptor analog of the invention having two $N_4$ binding arms.

The chemistry of Example 14 is outlined in FIG. 14.

Example 15

Preparation of $^{99m}$Tc-22

Stannous tartrate kits are prepared in an evacuator vial under nitrogen to contain 0.5 mL of disodium tartrate (10 mg/mL) and 0.1 mL stannous chloride (1.0 mg/mL. in ethanol). The pH of the solution is kept between 5 and 7.5 preferably 6.5. To this stannous tartrate solution is added 1.0 mL of sodium pertechnetate at a specific concentration of 35–50 mCi/mL in saline. The reaction mixture is allowed to stand at room temperature. In another evacuated vial, 200 μL of sodium phosphate (0.5 M, pH about 10.0) and 1.0 mL of compound 22 solution (1.0 mg/mL, see Example 4) are added successively. Then Tc-99m-Tartrate (50 mCi) is added, and the vial is incubated at 25° C.–100° C. for 10–30 min. The percent formation of radiolabeled compound 22 is determined by ITLC and HPLC using a radiometric detection system.

Figure 15:
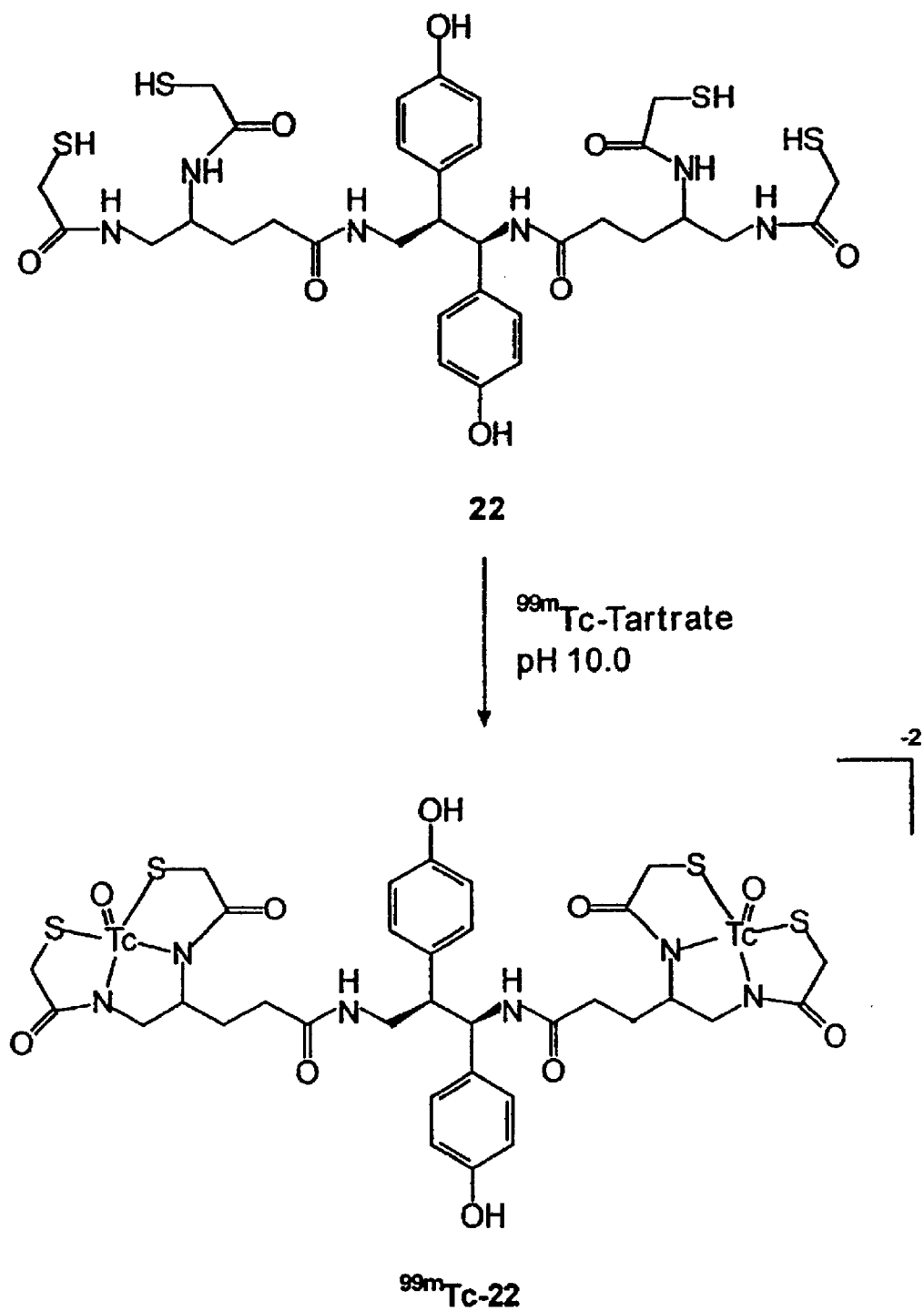
FIG. 15 illustrates the chemistry more fully described in Example 15 which may be used to form an estrogen receptor diagnostic agent of the invention from $^{99m}Tc$ and an estrogen receptor analog of the invention having two $N_2S_2$ binding arms, where the N atoms are part of amide groups and the sulfur atoms are in the form of thiols.

The chemistry of Example 15 is outlined in FIG. 15.

Example 16

Preparation of $^{99m}$TC-24

Stannous tartrate kits are prepared in an evacuator vial under nitrogen to contain 0.5 mL of disodium tartrate (10 mg/mL) and 0.1 mL stannous chloride (1.0 mg/mL in ethanol). The pH of the solution is kept between 5 and 7.5 preferably 6.5. To this stannous tartrate solution is added 1.0 mL of sodium pertechnetate at a specific concentration of 35–50 mCi/mL in saline. The reaction mixture is allowed to stand at room temperature. In another evacuated vial, 200 μL of sodium phosphate (0.5 M, pH about 8.5) and 1.0 mL of compound 24 (1.0 mg/mL, see Example 5) are added successively. Then Tc-99m-Tartrate (50 mCi) is added, and the vial is incubated at 25° C.–100° C. for 10–30 min. The percent formation of radiolabeled compound 24 is determined by ITLC and HPLC using a radiometric detection system.

Figure 16:
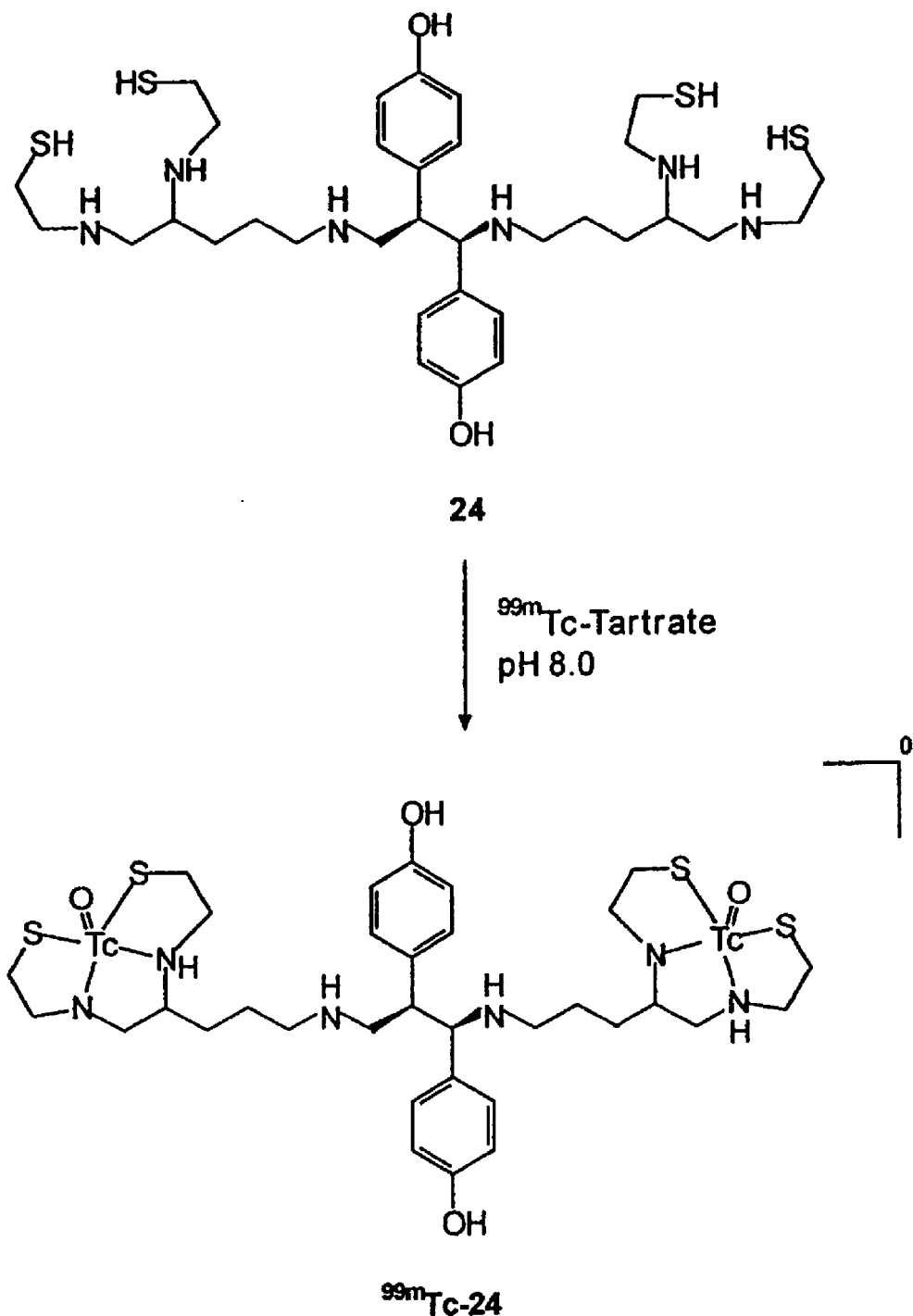
FIG. 16 illustrates the chemistry more fully described in Example 16 which may be used to form an estrogen receptor diagnostic agent of the invention from $^{99m}Tc$ and an estrogen receptor analog of the invention having two $N_2S_2$ binding arms, where the N atoms are part of amine groups and the sulfur atoms are in the form of thiols.

The chemistry of Example 16 is outlined in FIG. 16.

Example 17

Preparation of $^{99m}$TC-33

Stannous tartrate kits are prepared in an evacuator vial under nitrogen to contain 0.5 mL of disodium tartrate (10 mg/mL) and 0.1 mL stannous chloride (1.0 mg/mL in ethanol). The pH of the solution is kept between 8–8.5. To this stannous tartrate solution is added 1.0 mL of sodium pertechnetate (Na$^{+99m}$TCO$_4^-$) at a specific concentration of 35–50 mCi/mL in saline. The reaction mixture is allowed to stand at room temperature. In another evacuated vial, 200 μL of sodium phosphate (0.5 M, pH 8.5) and 1.0 mL of compound 33 (1.0 mg/mL, see Example 6) are added successively. Then $^{99m}$Tc-tartrate (50 mCi) is added, and the vial is incubated at 25° C.–100° C. for 10–30 min. The percent formation of radiolabeled compound 33 is determined by ITLC and gradient HPLC using a radiometric detection system.

Figure 17:
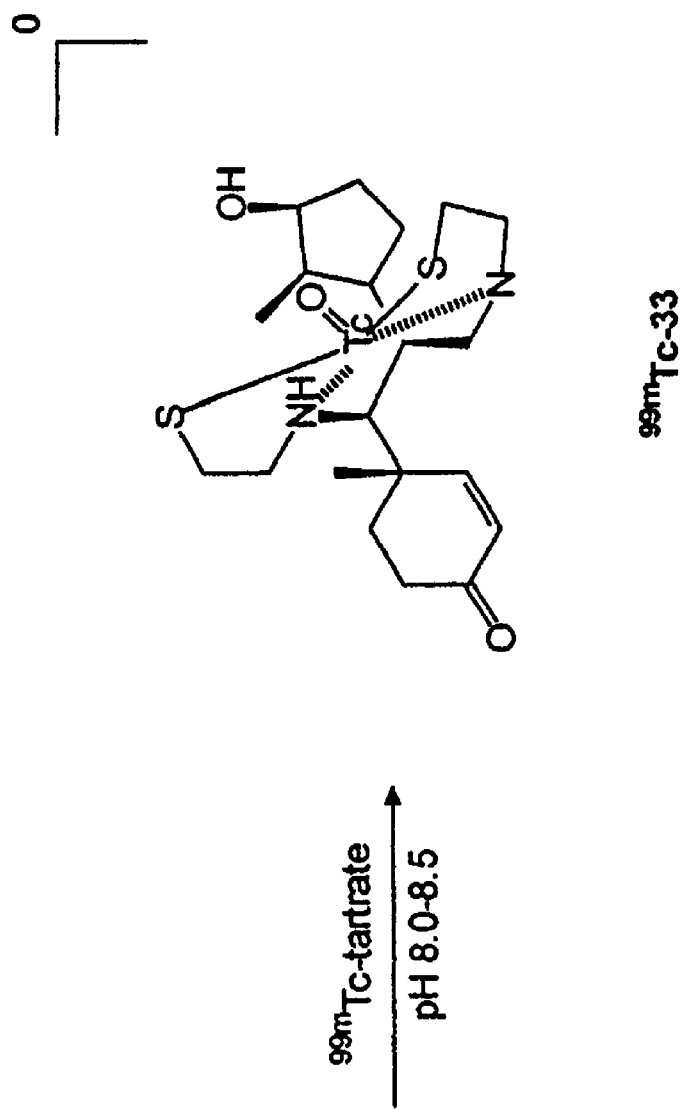
FIG. 17 illustrates the chemistry more fully described in Example 17 which may be used to form an androgen receptor diagnostic agent of the invention from $^{99m}Tc$ and an androgen receptor analog of the invention having four donor atoms forming an $N_2S_2$ binding core, where the N atoms are part of amine groups and the sulfur atoms are in the form of thiols.
Figure 17:
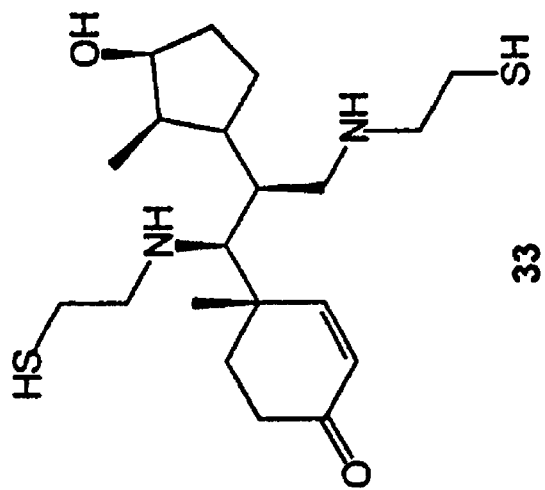

The chemistry of Example 17 is outlined in FIG. 17.

Example 18

Preparation of $^{90}$Y-35

To carrier-free 0.6 mCi Y-90 Cl3 (10 μL, 50 mM HCl, NEN DuPont), 0.18 mg of compound 35 (see Example 7) in 450 μL of 2.0 M NH$_4$OAc, pH 5.0, is added and the reaction mixture is allowed to proceed for 30 minutes at 80° C. The percent of $^{90}$Y radiolabeling monitored by a gradient HPLC system equipped with a radiometric detector is greater than 99%.

Figure 18:
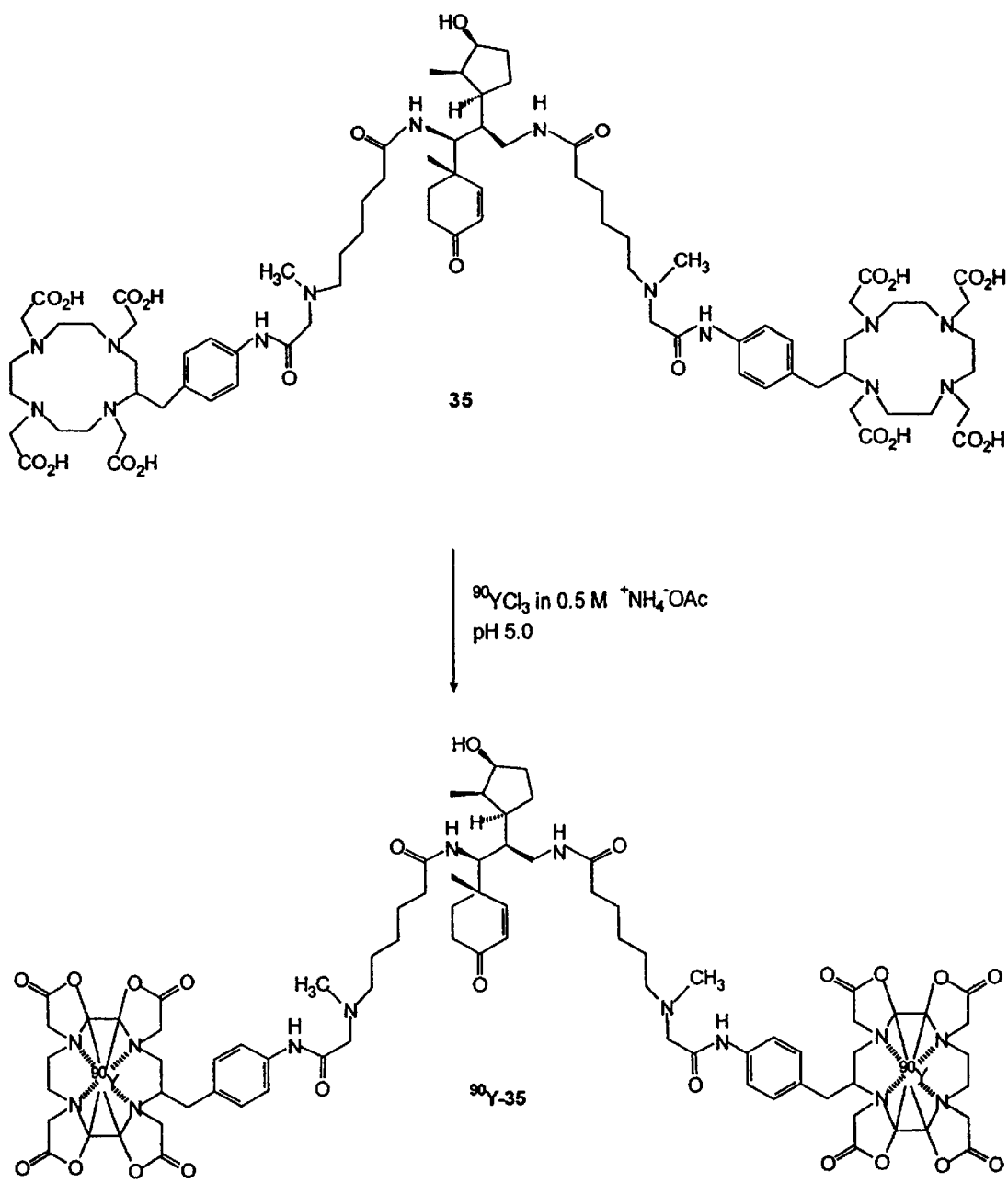
FIG. 18 illustrates the chemistry more fully described in Example 18 which may be used to form an androgen receptor therapeutic agent of the invention from $^{90}Y$ and an androgen receptor analog of the invention having two $N_4$ binding arms.

The chemistry of Example 18 is outlined in FIG. 18.

Example 19

Preparation of $^{99m}$Tc-37

Stannous tartrate kits are prepared in an evacuator vial under nitrogen to contain 0.5 mL of disodium tartrate (10 mg/mL), 0.1 mL of stannous chloride (1.0 mg/mL in ethanol), 0.1 mg of gentisic acid, 10–20 mg of lactose filler. The pH of the solution is kept between pH 5–7, preferably 6.0. To this stannous tartrate solution is added 1.0 mL of sodium pertechnetate at a specific concentration of 50 mCi/mL. The reaction mixture is allowed to stand at room temperature. In another evacuated vial, 200 μL of sodium phosphate (0.5 M, pH 8.0 or 10.0) and 1.0 mL of compound 37 (1.0 mg/mL, see Example 8) are added successively. Then $^{99m}$Tc-tartrate (50 mCi) is added, and the vial is incubated at 25° C.–100° C. for 10–30 minutes. The percent formation of $^{99m}$Tc-37 is determined by ITLC and isocratic HPLC system equipped with a radiometric detection.

Figure 19:
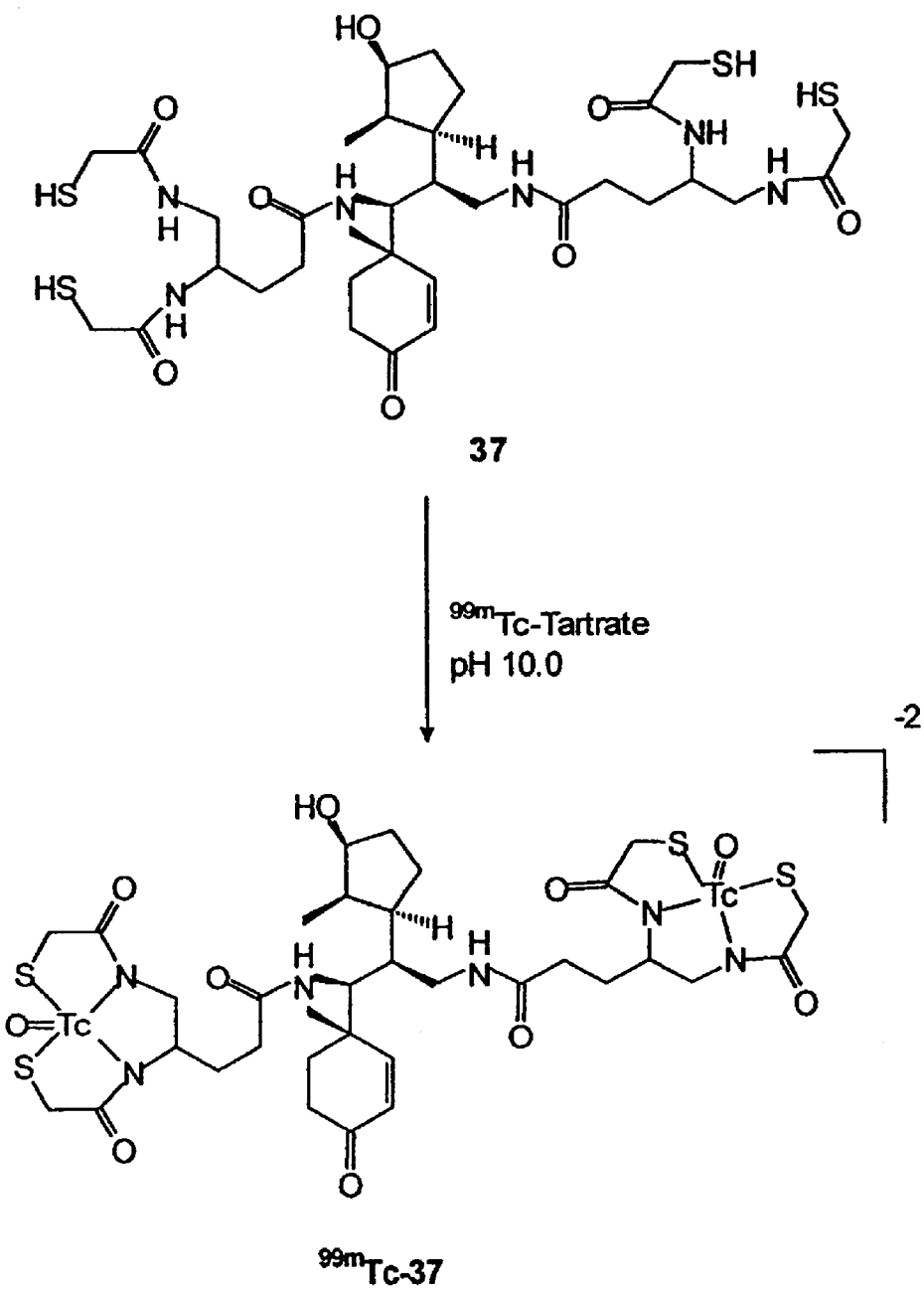
FIG. 19 illustrates the chemistry more fully described in Example 19 which may be used to form an androgen receptor diagnostic agent of the invention from $^{99m}Tc$ and an androgen receptor analog of the invention having two $N_2S_2$ binding arms, where the N atoms are part of amide groups and the sulfur atoms are in the form of thiols.

The chemistry of Example 19 is outlined in FIG. 19.

Example 20

Preparation of $^{99m}$Tc-38

Stannous tartrate kits are prepared in an evacuator vial under nitrogen to contain 0.5 mL of disodium tartrate (10 mg/mL), 0.1 mL of stannous chloride (1.0 mg/mL), 0.1 mg of gentisic acid, 10–20 mg of lactose filler. The pH of the solution is kept between 5.0–7.5, preferably 6.0. To this stannous tartrate solution is added 1.0 mL of sodium pertechnetate at a specific concentration of 50 mCi/mL. The reaction mixture is allowed to stand at room temperature. In another evacuated vial, 200 μL of sodium phosphate (0.5 M, pH 8.0 or 10.0) and 1.0 mL of compound 38 (1.0 mg/mL, see Example 9) are added successively. Then $^{99m}$Tc-tartrate (50 mCi) is added, and the vial is incubated at 25° C.–100° C. for 10–30 min. The percent formation of $^{99m}$Tc-38 is determined by ITLC and isocratic HPLC system equipped with a radiometric detector.

Figure 20:
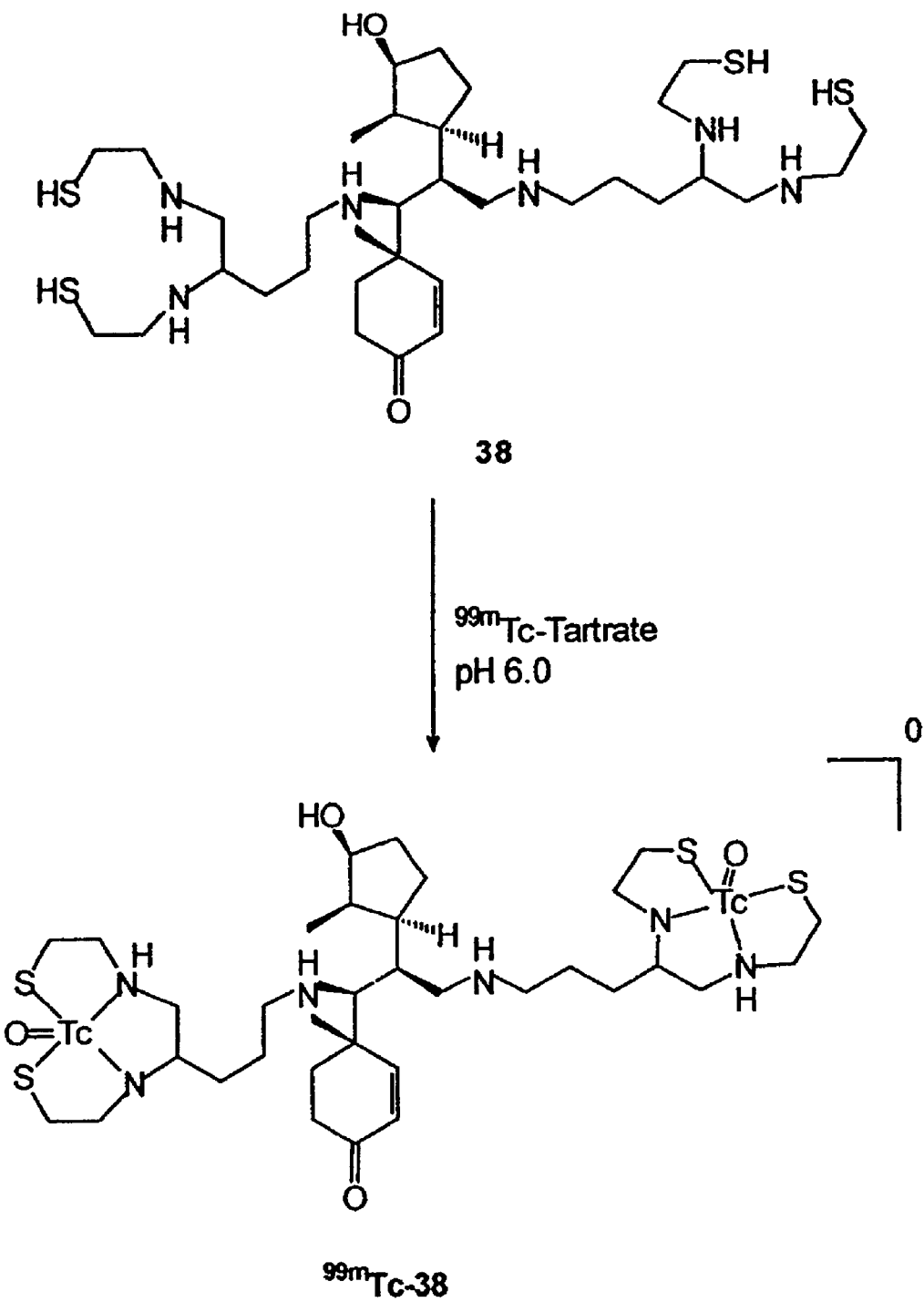
FIG. 20 illustrates the chemistry more fully described in Example 20 which may be used to form an androgen receptor diagnostic agent of the invention from $^{99m}Tc$ and an androgen receptor analog of the invention having two $N_2S_2$ binding arms, where the N atoms are part of amine groups and the sulfur atoms are in the form of thiols.

The chemistry of Example 20 is outlined in FIG. 20.

Example 21

Preparation of $^{186}$Re-9

Preparation of $^{186}$RE -citrate

A solution of 11.0 mg of citric acid 370 μg of gentisic acid and 460 μg of stannous chloride dihydrate in 100 μL H$_2$O is adjusted to a final pH of 2. To this solution, 500 μL of $^{186}$ReO$_4$(1–50 mCi) is added and incubated for 1–2 minutes.

Preparation of $^{186}$RE-9

Immediately after preparation of the $^{186}$Re-citrate, the steroid receptor analog 9 (0.1 to 1.0 mg in 600 μL isopropanol) is added. The reaction mixture is incubated at 90° C.–100° C. for 15–30 min and then is brought to room temperature by rapid cooling in an ice bath.

The chemistry of Example 21 is outlined in FIG. 21.

Example 22

Preparation of $^{186}$Re-11

Preparation of $^{186}$RE-citrate

A solution of 11.0 mg of citric acid 370 μg of gentisic acid and 460 μg of stannous chloride dihydrate in 100 μL H$_2$O is adjusted to a final pH of 2. To this solution, 500 μL of $^{186}$ReO$_4$ (1–50 mCi) is added and incubated for 1–2 minutes.

Preparation of $^{186}$RE-11

In an evacuated vial, 200 μL of sodium phosphate (0.5 M, pH 8.0) and 1.0 mL of the steroid receptor analog 11 (0.5–1.0 mg/mL) are added successively. Then $^{186}$Re-citrate (50 mCi) is added, and the vial is incubated at 25° C.–100° C. for 10–30 min. The percent formation of radiolabeled analog is determined by ITLC and a gradient HPLC system using a radiometric detector.

The chemistry of Example 22 is outlined in FIG. 22.

Example 23

Preparation of $^{188}$Re-23

Preparation of $^{188}$RE-citrate

Sodium perrhenate (3 mL, 15 mCi, produced from a W-188/Re-188 research scale generator) is added to a vial containing lyophilized mixture comprising citric acid, 75 mg; stannous chloride, 0.75 mg; gentisic acid, 0.25 mg; and lactose, 100 mg. The vial is agitated gently to mix the contents, then incubated at room temperature for 10 minutes to form a $^{188}$Re-citrate intermediate exchange complex.

Preparation of $^{188}$RE-23

To a vial containing 0.50–1.0 mg of steroid receptor analog comprising a hemithioacetate(ethoxyethyl)sulfur protecting group (compound 23, see Example 5), 0.5 mL of isopropyl alcohol is added and the vial is agitated for 2 min for complete dissolution of the ligand. Next, 0.3 mL of this solution is transferred to the vial containing the $^{188}$Re-citrate complex prepared above. After gentle mixing, the vial is incubated at 95–100° C. for 15–30 min. Then, immediately transferred to a ice bath for two minutes. The yields of $^{188}$Re-analog ranged between 90%–95% as measured by reverse phase $_{18}$ HPLC analysis.

Figure 23:
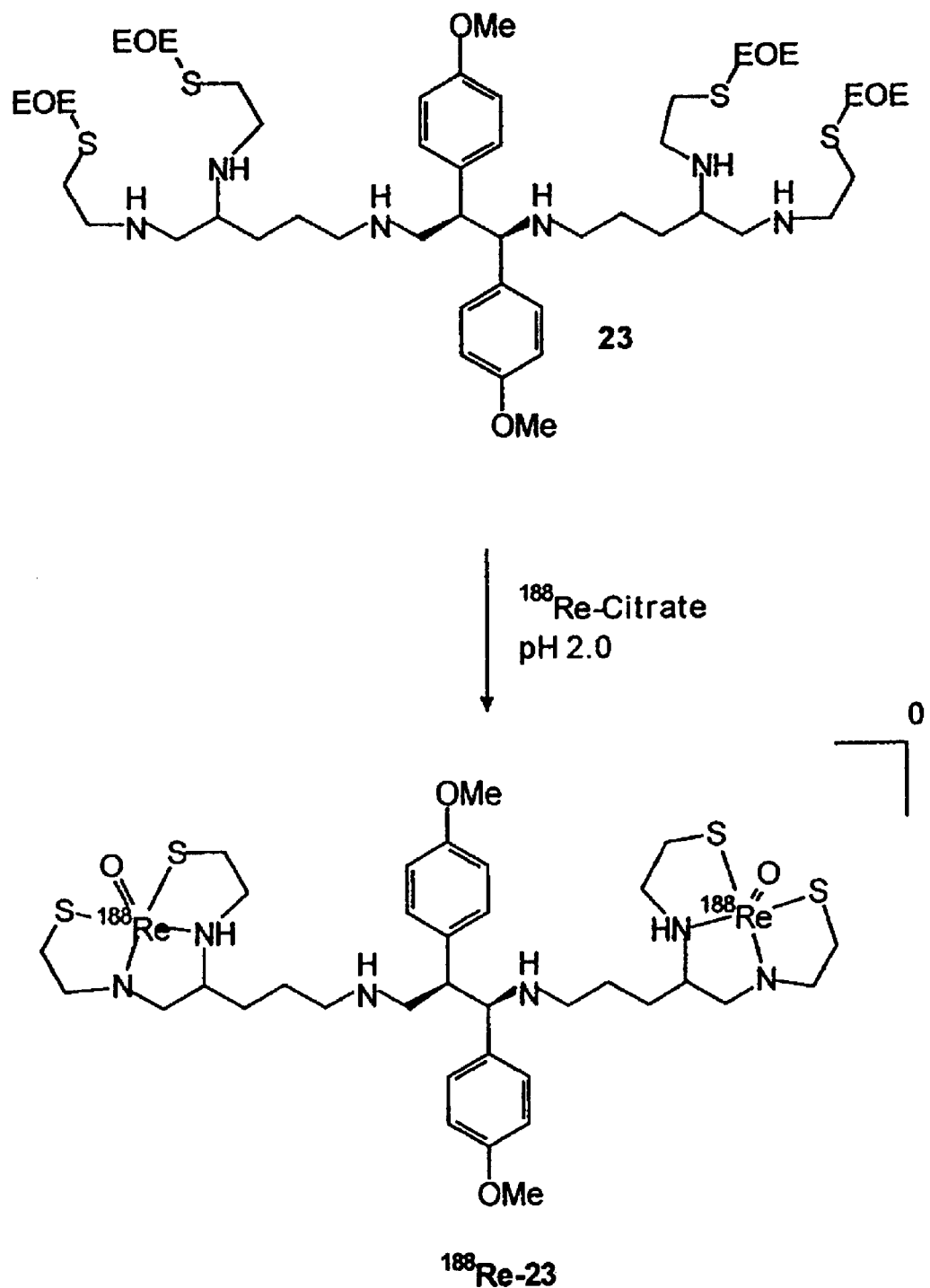
FIG. 23 illustrates the chemistry more fully described in Example 23 which may be used to form an estrogen receptor therapeutic agent of the invention from 188Re and an estrogen receptor analog of the invention having two $N_2S_2$ binding arms, where the N atoms are part of amine groups and the sulfur atoms are in protected form.

The chemistry of Example 23 is outlined in FIG. 23.

Example 24

Preparation of $^{188}$Re-24

Preparation of $^{188}$RE-citrate

Sodium perrhenate (3 mL, 15 mCi, produced from a W-188/Re-188 research scale generator) is added to a vial containing lyophilized mixture comprising citric acid, 75 mg; stannous chloride, 0.75 mg; gentisic acid, 0.25 mg; and lactose, 100 mg. The vial is agitated gently to mix the contents, then incubated at room temperature for 10 minutes to form a $^{188}$Re-citrate intermediate exchange complex.

Preparation of $^{188}$RE-24

In an evacuated vial, 200–500 μL of sodium phosphate (0.5 M, pH 8.0) and 1.0 mL of steroid receptor analog 24 (0.5–1.0 mg/mL, see Example 5) are added successively. Then $^{188}$Re-citrate (50 mCi) is added, and the vial is incubated at 25° C.–100° C. for 10–30 min. The percent formation of radiolabeled analog is determined by ITLC and a gradient HPLC system using a radiometric detector.

Figure 24:
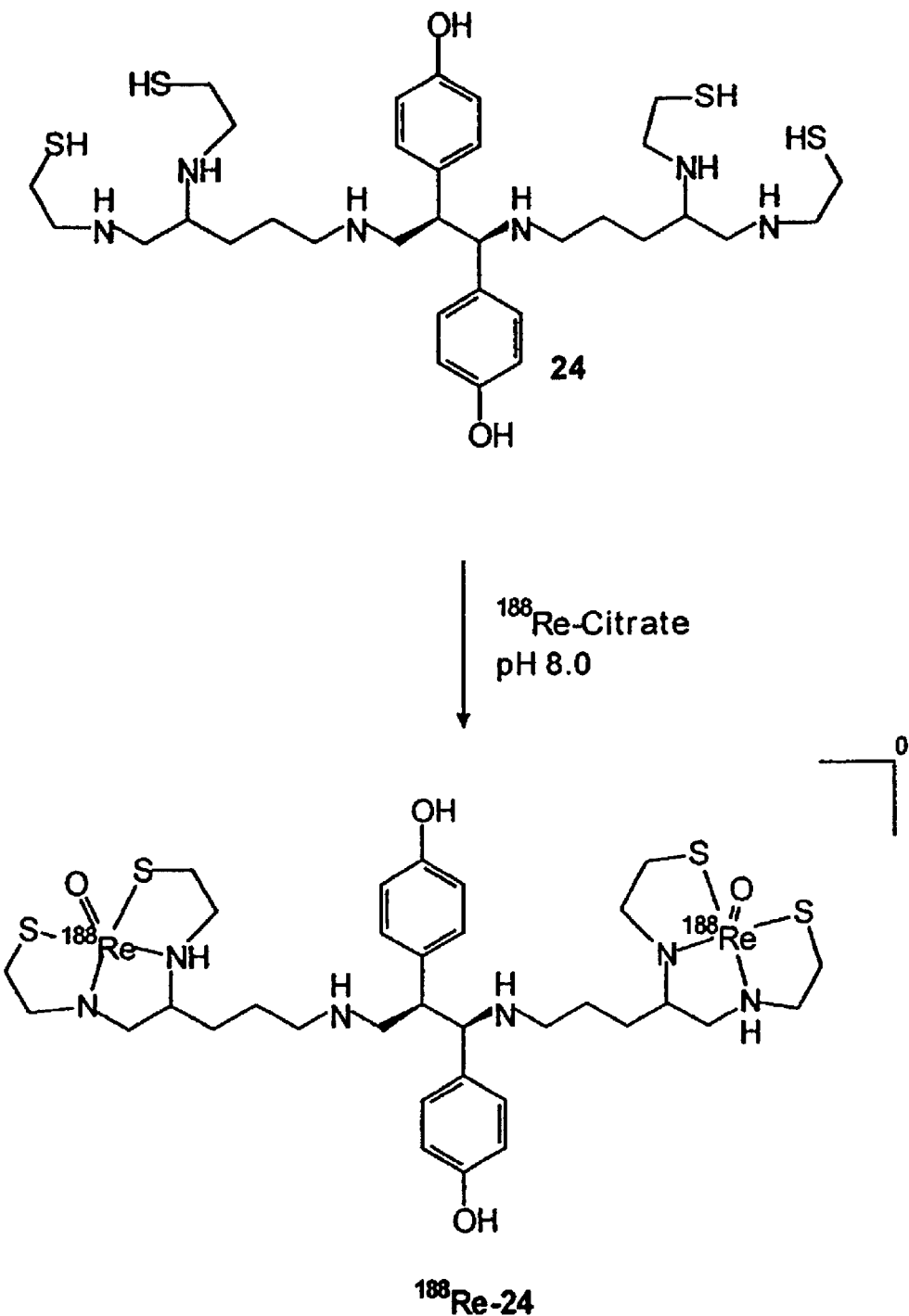
FIG. 24 illustrates the chemistry more fully described in Example 24 which may be used to form an estrogen receptor therapeutic agent of the invention from $^{188}Re$ and an estrogen receptor analog of the invention having two $N_2S_2$ binding arms, where the N atoms are part of amine groups and the sulfur atoms are in the form of thiols.

The chemistry of Example 24 is outlined in FIG. 24.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the formula (I)

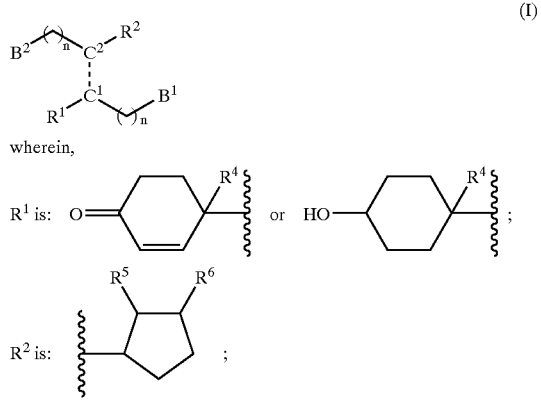

wherein, $R^1$ is, $R^2$ is:

$R^4$ is selected from H, —OH, halide and C$_1$–C$_3$alkyl;
$R^5$ is selected from H, —OH, halide and C$_1$–C$_3$alkyl;
$R^6$ is selected from H, —OH, —SH, halide, C$_1$–C$_3$alkyl, C(=O)CH$_3$, thio and oxo;
$C^1$ and $C^2$ are joined together by a single bond, where $C^1$ and $C^2$ are independently substituted with H, halogen, or C$_1$–C$_3$alkyl;

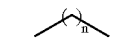

represents a number "n" of methylene (CH$_2$) or fluoromethylene (CFH or CF$_2$) groups, where n is independently selected at each occurrence from 0, 1 and 2;

$B^1$ and $B^2$ each has a structure independently selected from

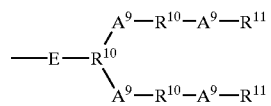

$R^{10}$ at each occurrence is independently selected from

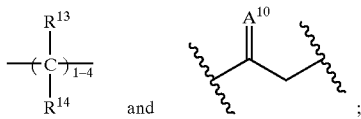

$R^{11}$ at each occurrence is independently selected from H and protecting groups for the $A^9$ moiety, where $A^9$ and $R^{11}$ may together form —N(CH$_2$—COOH)$_2$;

$R^{12}$ is selected from hydrogen and pro-drug substituents selected from the group consisting of C$_1$–C$_3$alkyl, —C(=O)(H, C$_1$–C$_3$alkyl or Ar); —C(=O)—(C$_1$–C$_3$alkylene)-N(independently H or C$_1$–C$_3$alkyl)$_2$, —C(=O)O—(H, C$_1$–C$_3$alkyl or Ar), —C(=O)CH(NH$_2$)(H, C$_1$–C$_3$alkyl or Ar), —(C$_1$–C$_3$alkylene)-C(=O)O—(H, C$_1$–C$_3$alkyl or Ar), —(C$_1$–C$_3$alkylene)-OC(=O)—(H, C$_1$–C$_3$alkyl or Ar), —(C$_1$–C$_3$alkylene)-N(independently H or C$_1$–C$_3$alkyl)$_2$, —(C$_1$–C$_3$alkylene)-NHC(=O)—Ar, —(C$_1$–C$_3$alkylene)-CN, —(C$_1$–C$_3$alkylene)-NO$_2$, and

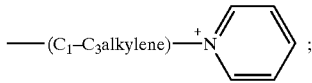

$R^{13}$ and $R^{14}$ are independently selected from H, $R^{15}$, CN, NO, NO$_2$, —C(OC$_1$–C$_3$alkyl)=NH, —N=C=O, —N=C=S, and —C(=O)OR$^{15}$ such that when $R^{10}$ is bonded to E then $R^{13}$ is a direct bond to E;

$R^{15}$ is C$_1$–C$_6$hydrocarbyl;

$A^9$ is an electron-donating moiety independently selected at each occurrence from O, S, C(=O)NH and N($R^{12}$);

$A^{10}$ is independently selected from O and S; and

E is an extender arm having a structure which provides a stable chain of 2–60 atoms selected from carbon, oxygen, nitrogen and sulfur.

2. A composition comprising a compound of claim 1 in admixture with a pharmaceutically acceptable carrier.

3. A compound of claim 1 in chelation with a metal species, where the metal species is a radionuclide.

4. A composition comprising a compound of claim 3 in admixture with a pharmaceutically acceptable carrier or diluent.

5. A method of binding a steroid analog to a steroid receptor for a therapeutic or diagnostic purpose comprising administering to a subject in need thereof a therapeutically or diagnostically effective amount of a compound of claim 3 or a composition of claim 4.

6. The method of claim 5 for a therapeutic purpose, wherein the metal species comprises $^{186}$Re/$^{188}$Re or $^{90}$Y.

7. The method of claim 5 for a diagnostic purpose, wherein the metal species comprises $^{111}$In or $^{99m}$Tc.

8. A method of imaging a steroid receptor comprising administering to a subject in need thereof a diagnostically effective amount of a compound of claim 3 or a composition of claim 4.

9. The method of claim 8 wherein the metal species comprises $^{111}$In or $^{99m}$Tc.

10. A method of killing a cell having a steroid receptor comprising administering to a subject in need thereof, in an amount effective to kill a cell, a compound of claim 3 or a composition of claim 4.

11. The method of claim 10 wherein the metal species comprises $^{186}$Re/$^{188}$Re or $^{90}$Y.

* * * * *